US012760067B2

(12) United States Patent
Alenfall et al.

(10) Patent No.: US 12,760,067 B2
(45) Date of Patent: Oct. 13, 2026

(54) PEPTIDES FOR USE IN SKIN AND HAIR PIGMENTATION

(71) Applicants: Follicum AB, Lund (SE); University of Bradford, Bradford (GB)

(72) Inventors: Jan Alenfall, Lomma (SE); Maria Ekblad, Södra Sandby (SE); Suman Singh, Jharkhand (IN); Desmond J. Tobin, Dublin (IE)

(73) Assignees: Follicum AB, Lund (SE); University of Bradford, Bradford (GB)

( * ) Notice: Subject to any disclaimer, the term of this patent is extended or adjusted under 35 U.S.C. 154(b) by 681 days.

(21) Appl. No.: 18/250,448

(22) PCT Filed: Oct. 28, 2021

(86) PCT No.: PCT/EP2021/080032

§ 371 (c)(1),
(2) Date: Apr. 25, 2023

(87) PCT Pub. No.: WO2022/090413

PCT Pub. Date: May 5, 2022

(65) Prior Publication Data

US 2024/0228536 A1 Jul. 11, 2024

(30) Foreign Application Priority Data

Oct. 28, 2020 (EP) .................................... 20204350

(51) Int. Cl.

| | |
|---|---|
| ***C07K 5/103*** | (2006.01) |
| ***A61K 8/60*** | (2006.01) |
| ***A61K 8/64*** | (2006.01) |
| ***A61K 8/92*** | (2006.01) |
| ***A61P 17/00*** | (2006.01) |
| ***A61Q 5/10*** | (2006.01) |
| ***A61Q 19/04*** | (2006.01) |

(52) U.S. Cl.

CPC ................ *C07K 5/101* (2013.01); *A61K 8/60* (2013.01); *A61K 8/64* (2013.01); *A61K 8/92* (2013.01); *A61P 17/00* (2018.01); *A61Q 5/10* (2013.01); *A61Q 19/04* (2013.01)

(58) Field of Classification Search

None

See application file for complete search history.

(56) References Cited

U.S. PATENT DOCUMENTS

| | | | | |
|---|---|---|---|---|
| 2007/0265431 | A1 | 11/2007 | Cunningham et al. | |
| 2010/0152119 | A1* | 6/2010 | Dal Farra .............. | A61Q 19/04 514/8.4 |
| 2011/0318380 | A1* | 12/2011 | Brix ..................... | C07K 14/705 424/193.1 |
| 2016/0132631 | A1* | 5/2016 | Bremel ................ | A61K 39/098 703/2 |
| 2020/0069786 | A1 | 3/2020 | Molnár et al. | |

FOREIGN PATENT DOCUMENTS

| | | | |
|---|---|---|---|
| EP | 2955194 | A1 | 12/2015 |
| WO | WO2013/077681 | A1 | 5/2013 |
| WO | WO2014/200910 | A2 | 12/2014 |

OTHER PUBLICATIONS

UNIPROT:P15927, accessed on Nov. 13, 2025 at https://www.uniprot.org/uniprotkb/P15927/entry (Year: 2025).*

Singh et al., Bone morphogenetic proteins differentially regulate pigmentation in human skin cells, Journal of Cell Science, 125(18): 4306-4319, May 28, 2012.

* cited by examiner

*Primary Examiner* — Christina Bradley

(74) *Attorney, Agent, or Firm* — Weston R. Gould; DINSMORE & SHOHL LLP

(57) ABSTRACT

The present invention relates to peptides and use of said peptides in skin and hair pigmentation. Further, the present invention relates to a composition comprising said peptides for topical delivery.

20 Claims, 29 Drawing Sheets

Specification includes a Sequence Listing.

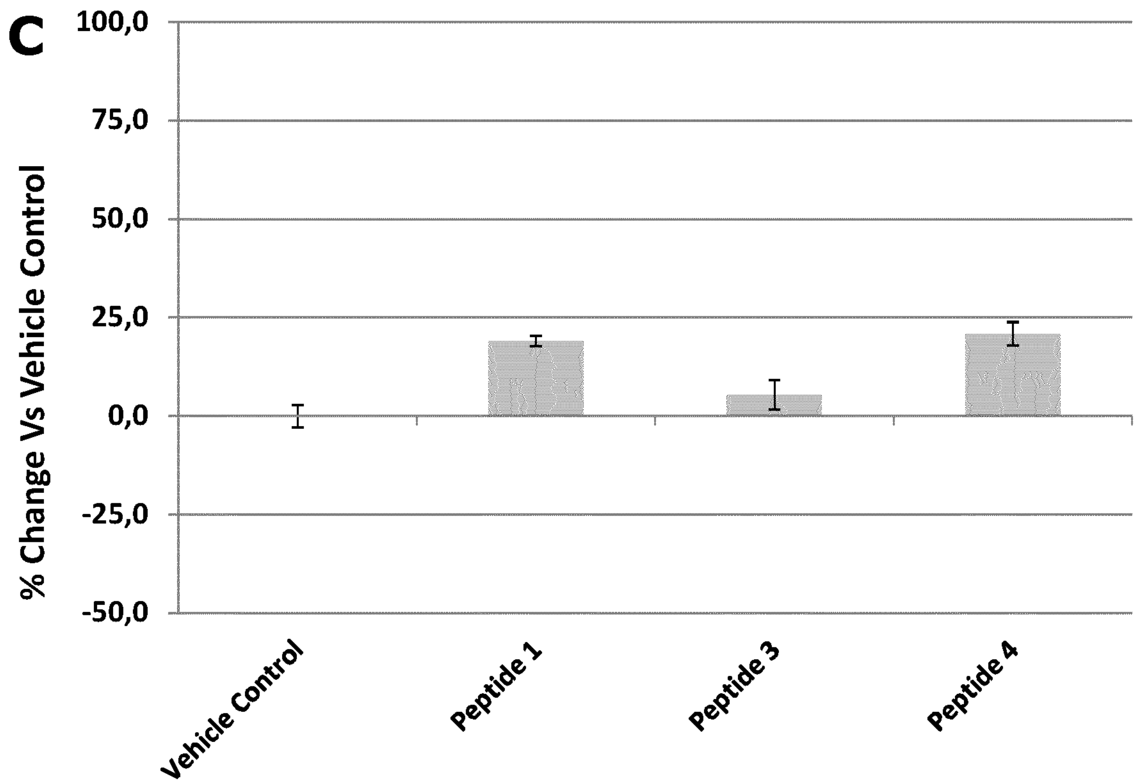
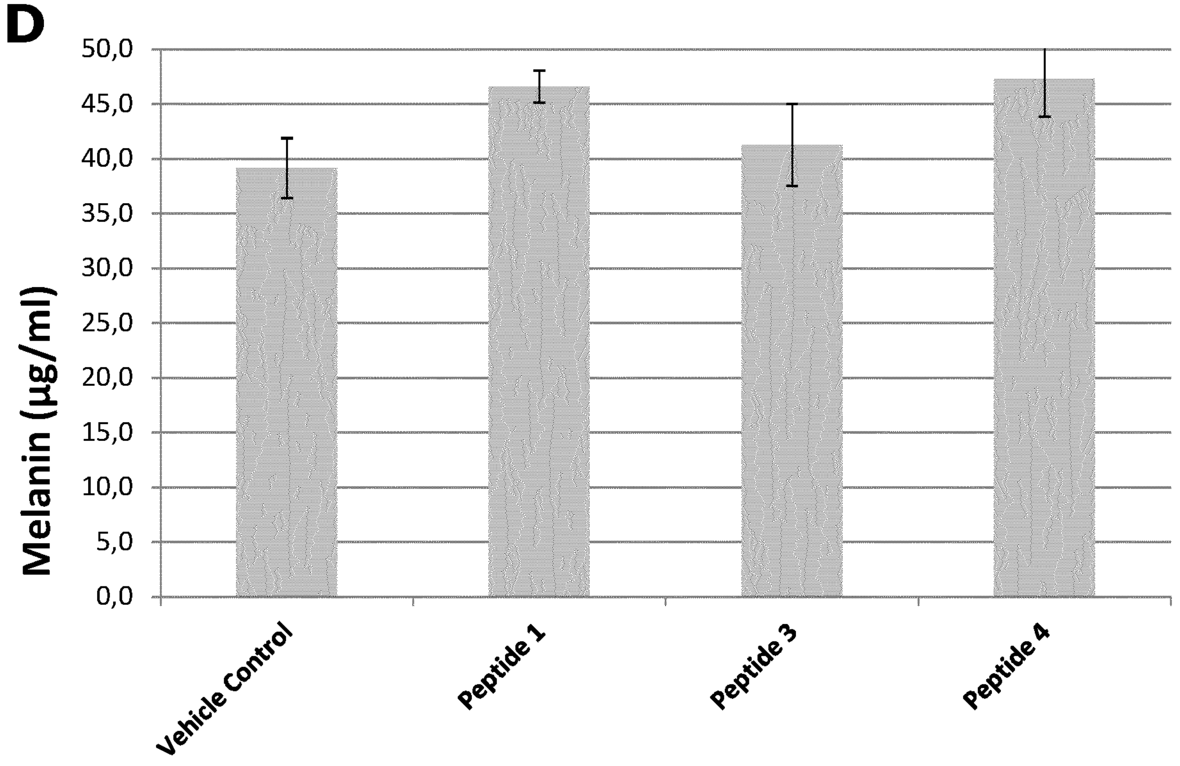
Figure 2, cont.

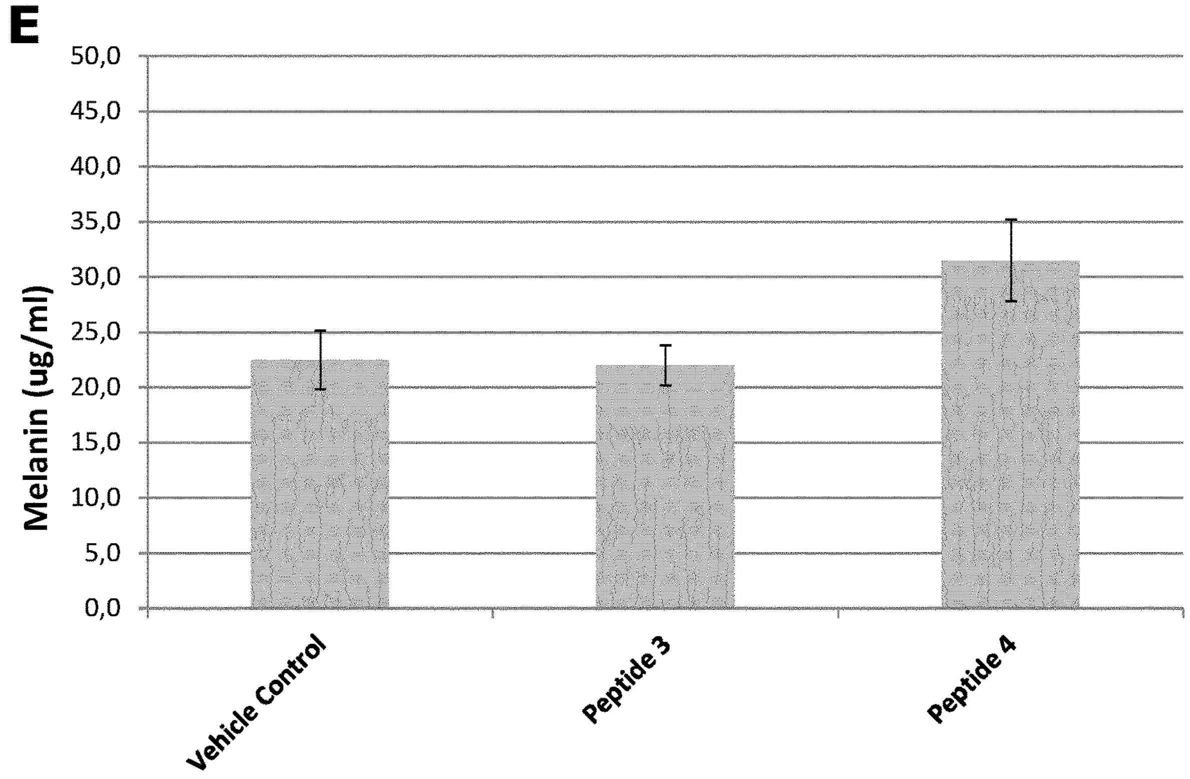
Figure 2, cont.

A

B
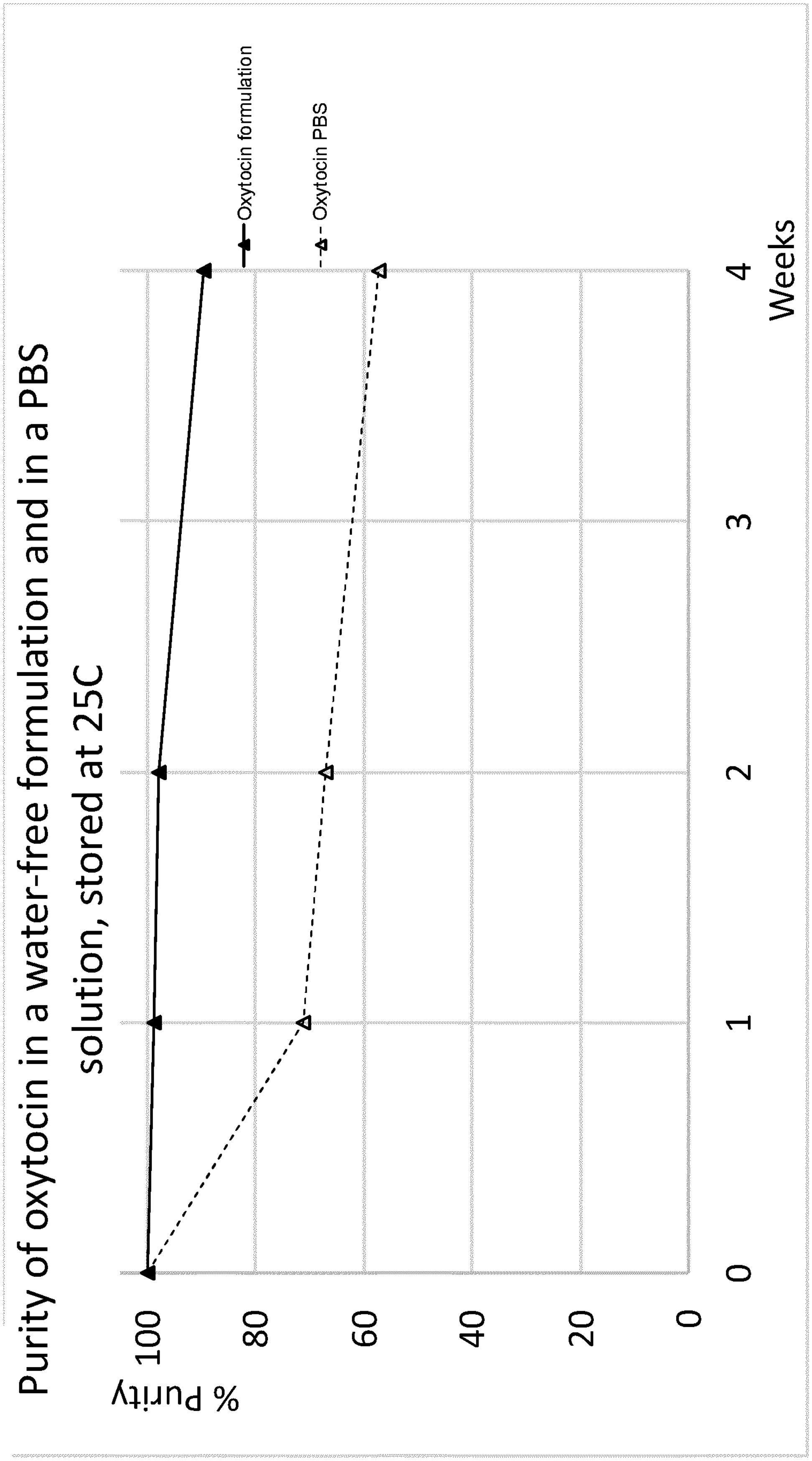
Figure 9, cont.

C
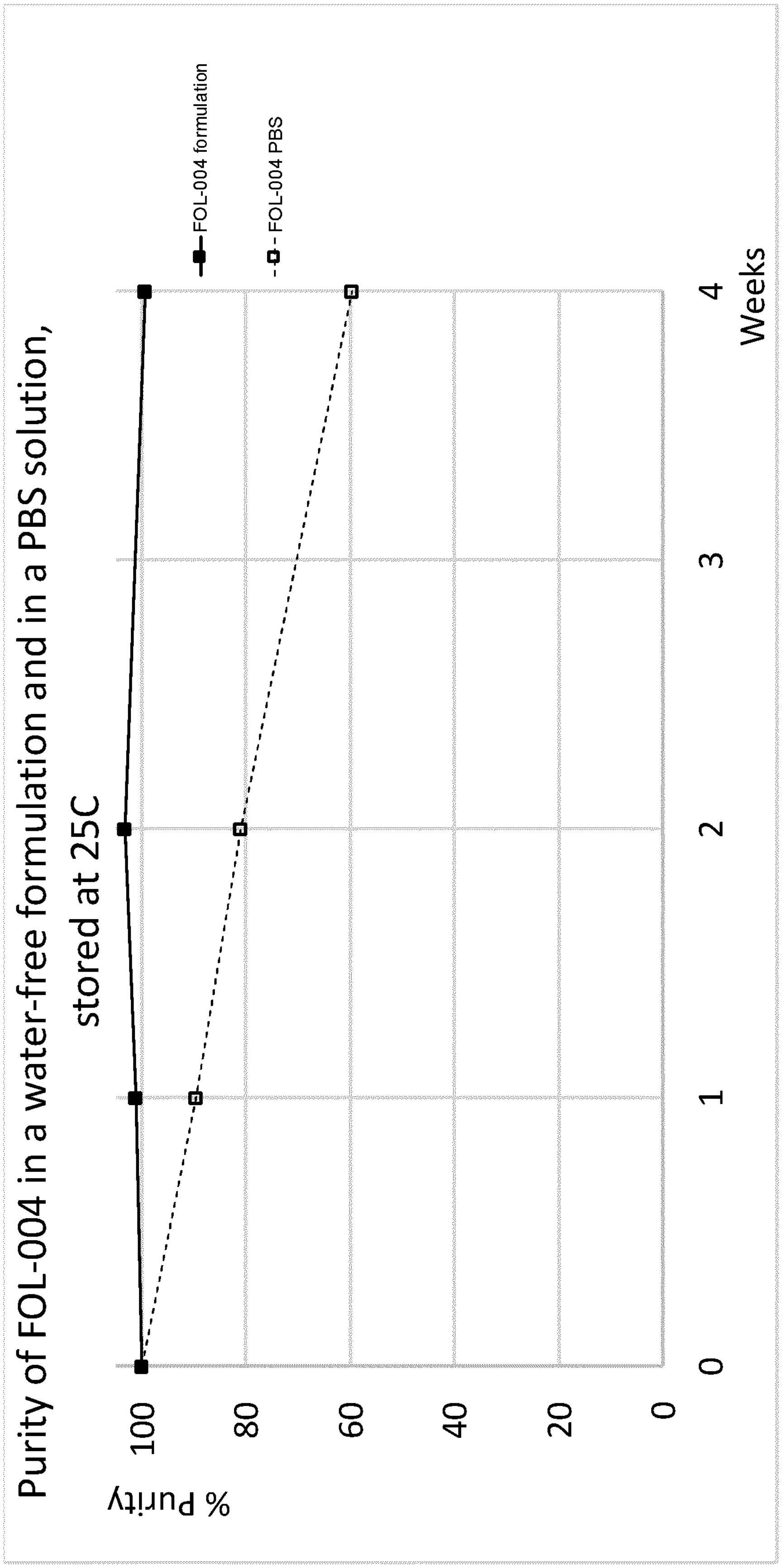
Figure 9, cont.

A

B

A

B

C

SEQUENCE LISTING

<160> NUMBER OF SEQ ID NOS: 196

<210> SEQ ID NO 1
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: peptide
<220> FEATURE:
<221> NAME/KEY: MISC_FEATURE
<222> LOCATION: (3)..(3)
<223> OTHER INFORMATION: X is H or A

<400> SEQUENCE: 1

Asn Ala Xaa Met
1

<210> SEQ ID NO 2
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: Peptide 1

<400> SEQUENCE: 2

Asn Ala His Met
1

<210> SEQ ID NO 3
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: Peptide 3

<400> SEQUENCE: 3

Ala Ala His Met
1

<210> SEQ ID NO 4
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: Peptide 4

<400> SEQUENCE: 4

Asn Ala Ala Met
1

<210> SEQ ID NO 5
<211> LENGTH: 15
<212> TYPE: PRT
<213> ORGANISM: Artificial

<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 5

Lys Pro Leu Ala Glu Ile Asp Ser Ile Glu Leu Ser Tyr Gly Ile
1 5 10 15

<210> SEQ ID NO 6
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: FOL-005, peptide

<400> SEQUENCE: 6

Val Asp Thr Tyr Asp Gly Asp Ile Ser Val Val Tyr Gly Leu Arg
1 5 10 15

<210> SEQ ID NO 7
<211> LENGTH: 15
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (1)..(15)
<223> OTHER INFORMATION: peptide

<400> SEQUENCE: 7

Val Asp Thr Tyr Asp Gly Asp Ile Ser Val Val Tyr Gly Leu Ser
1 5 10 15

<210> SEQ ID NO 8
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: Oxytocin, peptide

<400> SEQUENCE: 8

Cys Tyr Ile Gln Asn Cys Pro Leu Gly
1 5

<210> SEQ ID NO 9
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: FOL-004, peptide

<400> SEQUENCE: 9

Val Asp Val Pro Asn Gly Asp Ile Ser Leu Ala Tyr Gly Leu Arg
1 5 10 15

<210> SEQ ID NO 10
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: FOL-014, peptide

<400> SEQUENCE: 10

```
Lys Pro Leu Ala Glu Ile Asp Ser Ile Glu Leu Ser Tyr Gly Ile Lys
1               5                   10                  15
```

<210> SEQ ID NO 11
<211> LENGTH: 25
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(25)
<223> OTHER INFORMATION: FOL-199, peptide

<400> SEQUENCE: 11

```
Gly Lys Tyr Gly Phe Tyr Thr His Val Phe Arg Leu Lys Lys Trp Ile
1               5                   10                  15

Gln Lys Val Ile Asp Gln Phe Gly Glu
            20                  25
```

<210> SEQ ID NO 12
<211> LENGTH: 37
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(37)
<223> OTHER INFORMATION: LL-37, peptide

<400> SEQUENCE: 12

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35
```

<210> SEQ ID NO 13
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa=Asn or Ala
<220> FEATURE:
<221> NAME/KEY: MISC_FEATURE
<222> LOCATION: (3)..(3)
<223> OTHER INFORMATION: Xaa=His or Ala

<400> SEQUENCE: 13

Xaa Ala Xaa Met
1

<210> SEQ ID NO 14
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa=Cys, Pro or Gly
<220> FEATURE:
<221> NAME/KEY: MISC_FEATURE
<222> LOCATION: (5)..(5)
<223> OTHER INFORMATION: Xaa=Glu or Gly
<220> FEATURE:
<221> NAME/KEY: MISC_FEATURE
<222> LOCATION: (6)..(6)
<223> OTHER INFORMATION: Xaa=Cys, Asp or Ile
<220> FEATURE:
<221> NAME/KEY: MISC_FEATURE
<222> LOCATION: (7)..(7)
<223> OTHER INFORMATION: Xaa=Asp, Ile, Ser or Gly
<220> FEATURE:
<221> NAME/KEY: MISC_FEATURE
<222> LOCATION: (8)..(8)
<223> OTHER INFORMATION: Xaa=Ser, Asp or Gly
<220> FEATURE:
<221> NAME/KEY: MISC_FEATURE
<222> LOCATION: (10)..(10)
<223> OTHER INFORMATION: Xaa=Glu or Gly
<220> FEATURE:
<221> NAME/KEY: MISC_FEATURE
<222> LOCATION: (12)..(12)
<223> OTHER INFORMATION: Xaa=Ser or Thr

<400> SEQUENCE: 14

Lys Xaa Leu Ala Xaa Xaa Xaa Xaa Ile Xaa Leu Xaa Tyr Gly Ile Lys
1 5 10 15

<210> SEQ ID NO 15
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa=Glu or Gly
<220> FEATURE:
<221> NAME/KEY: MISC_FEATURE
<222> LOCATION: (3)..(3)
<223> OTHER INFORMATION: Xaa=Ser or Thr

<400> SEQUENCE: 15

Xaa Leu Xaa Tyr Gly Ile Lys
1 5

<210> SEQ ID NO 16
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa=Glu or Asn
<220> FEATURE:
<221> NAME/KEY: MISC_FEATURE
<222> LOCATION: (13)..(13)

<223> OTHER INFORMATION: Xaa=Arg or Gly

<400> SEQUENCE: 16

Val Asp Val Pro Xaa Gly Asp Ile Ser Leu Ala Tyr Xaa Leu Arg
1 5 10 15

<210> SEQ ID NO 17
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Xaa=Asp or Gly
<220> FEATURE:
<221> NAME/KEY: MISC_FEATURE
<222> LOCATION: (8)..(8)
<223> OTHER INFORMATION: Xaa=Ile or Gly

<400> SEQUENCE: 17

Val Asp Thr Tyr Asp Gly Xaa Xaa Ser Val Val Tyr Gly Leu Arg
1 5 10 15

<210> SEQ ID NO 18
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa=Asp or Gly
<220> FEATURE:
<221> NAME/KEY: MISC_FEATURE
<222> LOCATION: (6)..(6)
<223> OTHER INFORMATION: Xaa=Asp or Gly
<220> FEATURE:
<221> NAME/KEY: MISC_FEATURE
<222> LOCATION: (7)..(7)
<223> OTHER INFORMATION: Xaa=Ile or Arg
<220> FEATURE:
<221> NAME/KEY: MISC_FEATURE
<222> LOCATION: (8)..(8)
<223> OTHER INFORMATION: Xaa=Gly or absent
<220> FEATURE:
<221> NAME/KEY: MISC_FEATURE
<222> LOCATION: (9)..(9)
<223> OTHER INFORMATION: Xaa=Asp or absent

<400> SEQUENCE: 18

Gly Asp Pro Asn Xaa Xaa Xaa Xaa Xaa Ser Val Val Tyr Gly Leu Arg
1 5 10 15

<210> SEQ ID NO 19
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa=Cys, Pro or Gly
<220> FEATURE:
<221> NAME/KEY: MISC_FEATURE
<222> LOCATION: (5)..(5)
<223> OTHER INFORMATION: Xaa=Glu or Gly
<220> FEATURE:
<221> NAME/KEY: MISC_FEATURE
<222> LOCATION: (6)..(6)

<223> OTHER INFORMATION: Xaa=Cys, Ile or absent
<220> FEATURE:
<221> NAME/KEY: MISC_FEATURE
<222> LOCATION: (7)..(7)
<223> OTHER INFORMATION: Xaa=Asp, Gly or absent
<220> FEATURE:
<221> NAME/KEY: MISC_FEATURE
<222> LOCATION: (8)..(8)
<223> OTHER INFORMATION: Xaa=Ser, Gly or absent
<220> FEATURE:
<221> NAME/KEY: MISC_FEATURE
<222> LOCATION: (10)..(10)
<223> OTHER INFORMATION: Xaa=Glu or Gly

<400> SEQUENCE: 19

Lys Xaa Leu Ala Xaa Xaa Xaa Xaa Ile Xaa Leu Ser Tyr Gly Ile Lys
1 5 10 15

<210> SEQ ID NO 20
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa=Cys, Pro or Gly
<220> FEATURE:
<221> NAME/KEY: MISC_FEATURE
<222> LOCATION: (5)..(5)
<223> OTHER INFORMATION: Xaa=Glu or Gly
<220> FEATURE:
<221> NAME/KEY: MISC_FEATURE
<222> LOCATION: (7)..(7)
<223> OTHER INFORMATION: Xaa=Glu or Gly

<400> SEQUENCE: 20

Lys Xaa Leu Ala Xaa Ile Xaa Leu Ser Tyr Gly Ile Lys
1 5 10

<210> SEQ ID NO 21
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa=Asp or Gly
<220> FEATURE:
<221> NAME/KEY: MISC_FEATURE
<222> LOCATION: (2)..(2)
<223> OTHER INFORMATION: Xaa=Ile or Gly
<220> FEATURE:
<221> NAME/KEY: MISC_FEATURE
<222> LOCATION: (4)..(4)
<223> OTHER INFORMATION: Xaa=Val or Leu
<220> FEATURE:
<221> NAME/KEY: MISC_FEATURE
<222> LOCATION: (5)..(5)
<223> OTHER INFORMATION: Xaa=Val or Ala

<400> SEQUENCE: 21

Xaa Xaa Ser Xaa Xaa Tyr Gly Leu Arg
1 5

<210> SEQ ID NO 22
<211> LENGTH: 15
<212> TYPE: PRT
<213> ORGANISM: Artificial
<220> FEATURE:

<223> OTHER INFORMATION: synthetic peptide
<220> FEATURE:
<221> NAME/KEY: MISC_FEATURE
<222> LOCATION: (3)..(3)
<223> OTHER INFORMATION: Xaa=Thr or Val
<220> FEATURE:
<221> NAME/KEY: MISC_FEATURE
<222> LOCATION: (4)..(4)
<223> OTHER INFORMATION: Xaa=Tyr or Pro
<220> FEATURE:
<221> NAME/KEY: MISC_FEATURE
<222> LOCATION: (5)..(5)
<223> OTHER INFORMATION: Xaa=Asp or Asn
<220> FEATURE:
<221> NAME/KEY: MISC_FEATURE
<222> LOCATION: (7)..(7)
<223> OTHER INFORMATION: Xaa=Asp or Gly
<220> FEATURE:
<221> NAME/KEY: MISC_FEATURE
<222> LOCATION: (8)..(8)
<223> OTHER INFORMATION: Xaa=Ile or Gly
<220> FEATURE:
<221> NAME/KEY: MISC_FEATURE
<222> LOCATION: (10)..(10)
<223> OTHER INFORMATION: Xaa=Val or Leu
<220> FEATURE:
<221> NAME/KEY: MISC_FEATURE
<222> LOCATION: (11)..(11)
<223> OTHER INFORMATION: Xaa=Val or Ala

<400> SEQUENCE: 22

Val Asp Xaa Xaa Xaa Gly Xaa Xaa Ser Xaa Xaa Tyr Gly Leu Arg
1               5                   10                  15

<210> SEQ ID NO 23
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 23

Gly Asp Pro Asn Asp Gly Arg Gly Asp Ser Val Val Tyr Gly Leu Arg
1               5                   10                  15

<210> SEQ ID NO 24
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 24

Val Asp Thr Tyr Asp Gly Gly Ile Ser Val Val Tyr Gly Leu Arg
1               5                   10                  15

<210> SEQ ID NO 25
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)

<223> OTHER INFORMATION: peptide

<400> SEQUENCE: 25

Val Asp Thr Tyr Asp Gly Asp Gly Ser Val Val Tyr Gly Leu Arg
1 5 10 15

<210> SEQ ID NO 26
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 26

Val Asp Val Pro Glu Gly Asp Ile Ser Leu Ala Tyr Gly Leu Arg
1 5 10 15

<210> SEQ ID NO 27
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 27

Leu Asp Gly Leu Val Arg Ala Tyr Asp Asn Ile Ser Pro Val Gly
1 5 10 15

<210> SEQ ID NO 28
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 28

Gly Asp Pro Asn Gly Asp Ile Ser Val Val Tyr Gly Leu Arg
1 5 10

<210> SEQ ID NO 29
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 29

Val Asp Val Pro Asn Gly Asp Ile Ser Leu Ala Tyr Arg Leu Arg
1 5 10 15

<210> SEQ ID NO 30
<211> LENGTH: 15
<212> TYPE: PRT

<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 30

Val Asp Val Pro Glu Gly Asp Ile Ser Leu Ala Tyr Arg Leu Arg
1               5                   10                  15

<210> SEQ ID NO 31
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa=beta D
<220> FEATURE:
<221> NAME/KEY: MISC_FEATURE
<222> LOCATION: (2)..(2)
<223> OTHER INFORMATION: Xaa=beta-D

<400> SEQUENCE: 31

Val Xaa Thr Tyr Asp Gly Asp Ile Ser Val Val Tyr Gly Leu Arg
1               5                   10                  15

<210> SEQ ID NO 32
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa=beta-D

<400> SEQUENCE: 32

Val Asp Thr Tyr Xaa Gly Asp Ile Ser Val Val Tyr Gly Leu Arg
1               5                   10                  15

<210> SEQ ID NO 33
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Xaa=beta-D

<400> SEQUENCE: 33

Val Asp Thr Tyr Asp Gly Xaa Ile Ser Val Val Tyr Gly Leu Arg
1               5                   10                  15

<210> SEQ ID NO 34
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 34

Lys Cys Leu Ala Glu Cys Asp Ser Ile Glu Leu Ser Tyr Gly Ile Lys
1 5 10 15

<210> SEQ ID NO 35
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 35

Cys Leu Ala Glu Ile Asp Ser Cys
1 5

<210> SEQ ID NO 36
<211> LENGTH: 18
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(18)
<223> OTHER INFORMATION: peptide

<400> SEQUENCE: 36

Cys Phe Lys Pro Leu Ala Glu Ile Asp Ser Ile Glu Cys Ser Tyr Gly
1 5 10 15

Ile Lys

<210> SEQ ID NO 37
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 37

Lys Pro Leu Ala Glu Asp Ile Ser Ile Glu Leu Ser Tyr Gly Ile Lys
1 5 10 15

<210> SEQ ID NO 38
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 38

Lys Pro Leu Ala Glu Ile Gly Asp Ile Glu Leu Ser Tyr Gly Ile Lys
1 5 10 15

<210> SEQ ID NO 39
<211> LENGTH: 15

<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 39

Lys Pro Leu Ala Glu Gly Asp Ile Glu Leu Ser Tyr Gly Ile Lys
1 5 10 15

<210> SEQ ID NO 40
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 40

Lys Pro Leu Ala Glu Ile Glu Leu Ser Tyr Gly Ile Lys
1 5 10

<210> SEQ ID NO 41
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 41

Lys Pro Leu Ala Glu Ile Asp Ser Ile Glu Leu Thr Tyr Gly Ile Lys
1 5 10 15

<210> SEQ ID NO 42
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 42

Lys Pro Leu Ala Glu Ile Asp Gly Ile Glu Leu Ser Tyr Gly Ile Lys
1 5 10 15

<210> SEQ ID NO 43
<211> LENGTH: 16
<212> TYPE: PRT
<213> ORGANISM: Artificial
<220> FEATURE:
<223> OTHER INFORMATION: synthetic peptide

<400> SEQUENCE: 43

Lys Pro Leu Ala Glu Ile Asp Gly Ile Glu Leu Thr Tyr Gly Ile Lys
1 5 10 15

<210> SEQ ID NO 44
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 44

Lys Pro Leu Ala Glu Ile Gly Ser Ile Glu Leu Ser Tyr Gly Ile Lys
1 5 10 15

<210> SEQ ID NO 45
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 45

Lys Gly Leu Ala Glu Ile Asp Ser Ile Glu Leu Ser Tyr Gly Ile Lys
1 5 10 15

<210> SEQ ID NO 46
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 46

Lys Pro Leu Ala Gly Ile Asp Ser Ile Gly Leu Ser Tyr Gly Ile Lys
1 5 10 15

<210> SEQ ID NO 47
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: peptide

<400> SEQUENCE: 47

Lys Cys Leu Ala Glu Ile Asp Ser Cys Glu Leu Ser Tyr Gly Ile Lys
1 5 10 15

<210> SEQ ID NO 48
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 48

Cys Phe Lys Pro Leu Ala Glu Ile Asp Ser Ile Glu Cys
1 5 10

<210> SEQ ID NO 49
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 49

Leu Ala Glu Ile Asp Ser Ile Glu Leu Ser Tyr Gly Ile Lys
1 5 10

<210> SEQ ID NO 50
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 50

Ala Glu Ile Asp Ser Ile Glu Leu Ser Tyr Gly Ile Lys
1 5 10

<210> SEQ ID NO 51
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 51

Glu Ile Asp Ser Ile Glu Leu Ser Tyr Gly Ile Lys
1 5 10

<210> SEQ ID NO 52
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 52

Ile Asp Ser Ile Glu Leu Ser Tyr Gly Ile Lys
1 5 10

<210> SEQ ID NO 53
<211> LENGTH: 10
<212> TYPE: PRT
<213> ORGANISM: Artificial
<220> FEATURE:

<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 53

Asp Ser Ile Glu Leu Ser Tyr Gly Ile Lys
1               5                   10

<210> SEQ ID NO 54
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 54

Ser Ile Glu Leu Ser Tyr Gly Ile Lys
1               5

<210> SEQ ID NO 55
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 55

Ile Glu Leu Ser Tyr Gly Ile Lys
1               5

<210> SEQ ID NO 56
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 56

Lys Pro Leu Ala Glu Ile Asp Ser Ile Glu Leu Ser Tyr Gly Ile
1               5                   10                  15

<210> SEQ ID NO 57
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 57

Lys Pro Leu Ala Glu Ile Asp Ser Ile Glu Leu Ser Tyr Gly
1               5                   10

<210> SEQ ID NO 58
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 58

Lys Pro Leu Ala Glu Ile Asp Ser Ile Glu Leu Ser Tyr
1               5                   10

<210> SEQ ID NO 59
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 59

Lys Pro Leu Ala Glu Ile Asp Ser Ile Glu Leu Ser
1               5                   10

<210> SEQ ID NO 60
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 60

Lys Pro Leu Ala Glu Ile Asp Ser Ile Glu Leu
1               5                   10

<210> SEQ ID NO 61
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 61

Lys Pro Leu Ala Glu Ile Asp Ser Ile Glu
1               5                   10

<210> SEQ ID NO 62
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 62

Val Asp Thr Tyr Asp Gly Asp Ile Ser Val Val Tyr Gly Leu Ser
1               5                   10                  15

<210> SEQ ID NO 63
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: FOL-025, peptide

<400> SEQUENCE: 63

Val Asp Thr Tyr Asp Gly Asp Ile Ser Val Val Tyr Gly Leu
1               5                   10

<210> SEQ ID NO 64
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 64

Asp Thr Tyr Asp Gly Asp Ile Ser Val Val Tyr Gly Leu Arg
1               5                   10

<210> SEQ ID NO 65
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 65

Thr Tyr Asp Gly Asp Ile Ser Val Val Tyr Gly Leu Arg Ser
1               5                   10

<210> SEQ ID NO 66
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: FOL-024, peptide

<400> SEQUENCE: 66

Val Asp Thr Tyr Asp Gly Asp Ile Ser Val Val Tyr Gly
1               5                   10

<210> SEQ ID NO 67
<211> LENGTH: 13
<212> TYPE: PRT
<213> ORGANISM: Artificial

<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 67

Asp Thr Tyr Asp Gly Asp Ile Ser Val Val Tyr Gly Leu
1 5 10

<210> SEQ ID NO 68
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 68

Thr Tyr Asp Gly Asp Ile Ser Val Val Tyr Gly Leu Arg
1 5 10

<210> SEQ ID NO 69
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 69

Tyr Asp Gly Asp Ile Ser Val Val Tyr Gly Leu Arg Ser
1 5 10

<210> SEQ ID NO 70
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 70

Val Asp Thr Tyr Asp Gly Asp Ile Ser Val Val Tyr
1 5 10

<210> SEQ ID NO 71
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 71

Asp Thr Tyr Asp Gly Asp Ile Ser Val Val Tyr Gly
1 5 10

<210> SEQ ID NO 72
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 72

Thr Tyr Asp Gly Asp Ile Ser Val Val Tyr Gly Leu
1               5                   10

<210> SEQ ID NO 73
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 73

Tyr Asp Gly Asp Ile Ser Val Val Tyr Gly Leu Arg
1               5                   10

<210> SEQ ID NO 74
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 74

Asp Gly Asp Ile Ser Val Val Tyr Gly Leu Arg Ser
1               5                   10

<210> SEQ ID NO 75
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 75

Val Asp Thr Tyr Asp Gly Asp Ile Ser Val Val
1               5                   10

<210> SEQ ID NO 76
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)

<223> OTHER INFORMATION: peptide

<400> SEQUENCE: 76

Asp Thr Tyr Asp Gly Asp Ile Ser Val Val Tyr
1 5 10

<210> SEQ ID NO 77
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 77

Thr Tyr Asp Gly Asp Ile Ser Val Val Tyr Gly
1 5 10

<210> SEQ ID NO 78
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 78

Tyr Asp Gly Asp Ile Ser Val Val Tyr Gly Leu
1 5 10

<210> SEQ ID NO 79
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 79

Asp Gly Asp Ile Ser Val Val Tyr Gly Leu Arg
1 5 10

<210> SEQ ID NO 80
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 80

Gly Asp Ile Ser Val Val Tyr Gly Leu Arg Ser
1 5 10

<210> SEQ ID NO 81
<211> LENGTH: 10
<212> TYPE: PRT

<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 81

Val Asp Thr Tyr Asp Gly Asp Ile Ser Val
1 5 10

<210> SEQ ID NO 82
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 82

Asp Thr Tyr Asp Gly Asp Ile Ser Val Val
1 5 10

<210> SEQ ID NO 83
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 83

Thr Tyr Asp Gly Asp Ile Ser Val Val Tyr
1 5 10

<210> SEQ ID NO 84
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 84

Tyr Asp Gly Asp Ile Ser Val Val Tyr Gly
1 5 10

<210> SEQ ID NO 85
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 85

Asp Gly Asp Ile Ser Val Val Tyr Gly Leu 1 5 10

<210> SEQ ID NO 86
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: FOL-009h, peptide

<400> SEQUENCE: 86

Gly Asp Ile Ser Val Val Tyr Gly Leu Arg
1 5 10

<210> SEQ ID NO 87
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 87

Asp Ile Ser Val Val Tyr Gly Leu Arg Ser
1 5 10

<210> SEQ ID NO 88
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: FOL-019h, peptide

<400> SEQUENCE: 88

Val Asp Thr Tyr Asp Gly Asp Ile Ser
1 5

<210> SEQ ID NO 89
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 89

Asp Thr Tyr Asp Gly Asp Ile Ser Val
1 5

<210> SEQ ID NO 90
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 90

Thr Tyr Asp Gly Asp Ile Ser Val Val
1               5

<210> SEQ ID NO 91
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 91

Tyr Asp Gly Asp Ile Ser Val Val Tyr
1               5

<210> SEQ ID NO 92
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 92

Asp Gly Asp Ile Ser Val Val Tyr Gly
1               5

<210> SEQ ID NO 93
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 93

Gly Asp Ile Ser Val Val Tyr Gly Leu
1               5

<210> SEQ ID NO 94
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 94

Asp Ile Ser Val Val Tyr Gly Leu Arg
1               5

<210> SEQ ID NO 95
<211> LENGTH: 9

<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 95

Ile Ser Val Val Tyr Gly Leu Arg Ser
1               5

<210> SEQ ID NO 96
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 96

Val Asp Thr Tyr Asp Gly Asp Ile
1               5

<210> SEQ ID NO 97
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 97

Asp Thr Tyr Asp Gly Asp Ile Ser
1               5

<210> SEQ ID NO 98
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 98

Thr Tyr Asp Gly Asp Ile Ser Val
1               5

<210> SEQ ID NO 99
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 99

Tyr Asp Gly Asp Ile Ser Val Val
1               5

<210> SEQ ID NO 100
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 100

Asp Gly Asp Ile Ser Val Val Tyr
1               5

<210> SEQ ID NO 101
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 101

Gly Asp Ile Ser Val Val Tyr Gly
1               5

<210> SEQ ID NO 102
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 102

Asp Ile Ser Val Val Tyr Gly Leu
1               5

<210> SEQ ID NO 103
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 103

Ile Ser Val Val Tyr Gly Leu Arg
1               5

<210> SEQ ID NO 104
<211> LENGTH: 7
<212> TYPE: PRT
<213> ORGANISM: Artificial
<220> FEATURE:
<223> OTHER INFORMATION: synthetic peptide
<220> FEATURE:

<221> NAME/KEY: MISC_FEATURE
<222> LOCATION: (1)..(7)
<223> OTHER INFORMATION: peptide

<400> SEQUENCE: 104

Val Asp Thr Tyr Asp Gly Asp
1 5

<210> SEQ ID NO 105
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 105

Asp Thr Tyr Asp Gly Asp Ile
1 5

<210> SEQ ID NO 106
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 106

Thr Tyr Asp Gly Asp Ile Ser
1 5

<210> SEQ ID NO 107
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 107

Tyr Asp Gly Asp Ile Ser Val
1 5

<210> SEQ ID NO 108
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 108

Asp Gly Asp Ile Ser Val Val
1 5

<210> SEQ ID NO 109

<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 109

Gly Asp Ile Ser Val Val Tyr
1               5

<210> SEQ ID NO 110
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 110

Asp Ile Ser Val Val Tyr Gly
1               5

<210> SEQ ID NO 111
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 111

Ile Ser Val Val Tyr Gly Leu
1               5

<210> SEQ ID NO 112
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 112

Asp Thr Tyr Asp Gly Asp
1               5

<210> SEQ ID NO 113
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 113

```
Thr Tyr Asp Gly Asp Ile
1               5


<210> SEQ ID NO 114
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 114

Tyr Asp Gly Asp Ile Ser
1               5


<210> SEQ ID NO 115
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 115

Asp Gly Asp Ile Ser Val
1               5


<210> SEQ ID NO 116
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 116

Gly Asp Ile Ser Val Val
1               5


<210> SEQ ID NO 117
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 117

Asp Ile Ser Val Val Tyr
1               5


<210> SEQ ID NO 118
<211> LENGTH: 6
<212> TYPE: PRT
<213> ORGANISM: Artificial
<220> FEATURE:
<223> OTHER INFORMATION: synthetic peptide
```

<220> FEATURE:
<221> NAME/KEY: MISC_FEATURE
<222> LOCATION: (1)..(6)
<223> OTHER INFORMATION: peptide

<400> SEQUENCE: 118

Ile Ser Val Val Tyr Gly
1               5

<210> SEQ ID NO 119
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 119

Thr Tyr Asp Gly Asp
1               5

<210> SEQ ID NO 120
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 120

Tyr Asp Gly Asp Ile
1               5

<210> SEQ ID NO 121
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 121

Asp Gly Asp Ile Ser
1               5

<210> SEQ ID NO 122
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 122

Gly Asp Ile Ser Val
1               5

<210> SEQ ID NO 123
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 123

Asp Ile Ser Val Val
1               5

<210> SEQ ID NO 124
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 124

Ile Ser Val Val Tyr
1               5

<210> SEQ ID NO 125
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 125

Ser Val Val Tyr Gly
1               5

<210> SEQ ID NO 126
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: FOL-002, peptide

<400> SEQUENCE: 126

Val Asp Thr Tyr Asp Gly Arg Gly Asp Ser Val Val Tyr Gly Leu Arg
1               5                   10                  15

<210> SEQ ID NO 127
<211> LENGTH: 15
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(15)
<223> OTHER INFORMATION: peptide

<400> SEQUENCE: 127

Asp Val Pro Asn Gly Asp Ile Ser Leu Ala Tyr Gly Leu Arg Ser
1 5 10 15

<210> SEQ ID NO 128
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: FOL-016, peptide

<400> SEQUENCE: 128

Val Asp Val Pro Asn Gly Asp Ile Ser Leu Ala Tyr Gly Leu
1 5 10

<210> SEQ ID NO 129
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: FOL-007, peptide

<400> SEQUENCE: 129

Asp Val Pro Asn Gly Asp Ile Ser Leu Ala Tyr Gly Leu Arg
1 5 10

<210> SEQ ID NO 130
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(14)
<223> OTHER INFORMATION: peptide

<400> SEQUENCE: 130

Val Pro Asn Gly Asp Ile Ser Leu Ala Tyr Gly Leu Arg Ser
1 5 10

<210> SEQ ID NO 131
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: FOL-017, peptide

<400> SEQUENCE: 131

Val Asp Val Pro Asn Gly Asp Ile Ser Leu Ala Tyr Gly
1 5 10

<210> SEQ ID NO 132
<211> LENGTH: 13
<212> TYPE: PRT
<213> ORGANISM: Artificial
<220> FEATURE:

<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 132

Asp Val Pro Asn Gly Asp Ile Ser Leu Ala Tyr Gly Leu
1 5 10

<210> SEQ ID NO 133
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 133

Val Pro Asn Gly Asp Ile Ser Leu Ala Tyr Gly Leu Arg
1 5 10

<210> SEQ ID NO 134
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(13)
<223> OTHER INFORMATION: peptide

<400> SEQUENCE: 134

Pro Asn Gly Asp Ile Ser Leu Ala Tyr Gly Leu Arg Ser
1 5 10

<210> SEQ ID NO 135
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 135

Val Asp Val Pro Asn Gly Asp Ile Ser Leu Ala Tyr
1 5 10

<210> SEQ ID NO 136
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 136

Asp Val Pro Asn Gly Asp Ile Ser Leu Ala Tyr Gly
1 5 10

<210> SEQ ID NO 137
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 137

Val Pro Asn Gly Asp Ile Ser Leu Ala Tyr Gly Leu
1               5                   10

<210> SEQ ID NO 138
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: FOL-008, peptide

<400> SEQUENCE: 138

Pro Asn Gly Asp Ile Ser Leu Ala Tyr Gly Leu Arg
1               5                   10

<210> SEQ ID NO 139
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(12)
<223> OTHER INFORMATION: peptide

<400> SEQUENCE: 139

Asn Gly Asp Ile Ser Leu Ala Tyr Gly Leu Arg Ser
1               5                   10

<210> SEQ ID NO 140
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: FOL-018, peptide

<400> SEQUENCE: 140

Val Asp Val Pro Asn Gly Asp Ile Ser Leu Ala
1               5                   10

<210> SEQ ID NO 141
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 141

Asp Val Pro Asn Gly Asp Ile Ser Leu Ala Tyr
1 5 10

<210> SEQ ID NO 142
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 142

Val Pro Asn Gly Asp Ile Ser Leu Ala Tyr Gly
1 5 10

<210> SEQ ID NO 143
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 143

Pro Asn Gly Asp Ile Ser Leu Ala Tyr Gly Leu
1 5 10

<210> SEQ ID NO 144
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 144

Asn Gly Asp Ile Ser Leu Ala Tyr Gly Leu Arg
1 5 10

<210> SEQ ID NO 145
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(11)
<223> OTHER INFORMATION: peptide

<400> SEQUENCE: 145

Gly Asp Ile Ser Leu Ala Tyr Gly Leu Arg Ser
1 5 10

<210> SEQ ID NO 146
<211> LENGTH: 10
<212> TYPE: PRT
<213> ORGANISM: Artificial

<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 146

Val Asp Val Pro Asn Gly Asp Ile Ser Leu
1 5 10

<210> SEQ ID NO 147
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 147

Asp Val Pro Asn Gly Asp Ile Ser Leu Ala
1 5 10

<210> SEQ ID NO 148
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 148

Val Pro Asn Gly Asp Ile Ser Leu Ala Tyr
1 5 10

<210> SEQ ID NO 149
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 149

Pro Asn Gly Asp Ile Ser Leu Ala Tyr Gly
1 5 10

<210> SEQ ID NO 150
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 150

Asn Gly Asp Ile Ser Leu Ala Tyr Gly Leu
1 5 10

<210> SEQ ID NO 151
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: FOL-009, peptide

<400> SEQUENCE: 151

Gly Asp Ile Ser Leu Ala Tyr Gly Leu Arg
1               5                   10

<210> SEQ ID NO 152
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(10)
<223> OTHER INFORMATION: peptide

<400> SEQUENCE: 152

Asp Ile Ser Leu Ala Tyr Gly Leu Arg Ser
1               5                   10

<210> SEQ ID NO 153
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: FOL-019, peptide

<400> SEQUENCE: 153

Val Asp Val Pro Asn Gly Asp Ile Ser
1               5

<210> SEQ ID NO 154
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 154

Asp Val Pro Asn Gly Asp Ile Ser Leu
1               5

<210> SEQ ID NO 155
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)

<223> OTHER INFORMATION: peptide

<400> SEQUENCE: 155

Val Pro Asn Gly Asp Ile Ser Leu Ala
1 5

<210> SEQ ID NO 156
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 156

Pro Asn Gly Asp Ile Ser Leu Ala Tyr
1 5

<210> SEQ ID NO 157
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 157

Asn Gly Asp Ile Ser Leu Ala Tyr Gly
1 5

<210> SEQ ID NO 158
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 158

Gly Asp Ile Ser Leu Ala Tyr Gly Leu
1 5

<210> SEQ ID NO 159
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 159

Asp Ile Ser Leu Ala Tyr Gly Leu Arg
1 5

<210> SEQ ID NO 160
<211> LENGTH: 9
<212> TYPE: PRT

<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(9)
<223> OTHER INFORMATION: peptide

<400> SEQUENCE: 160

Ile Ser Leu Ala Tyr Gly Leu Arg Ser
1               5

<210> SEQ ID NO 161
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 161

Val Asp Val Pro Asn Gly Asp Ile
1               5

<210> SEQ ID NO 162
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 162

Asp Val Pro Asn Gly Asp Ile Ser
1               5

<210> SEQ ID NO 163
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 163

Val Pro Asn Gly Asp Ile Ser Leu
1               5

<210> SEQ ID NO 164
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 164

Pro Asn Gly Asp Ile Ser Leu Ala 1 5

<210> SEQ ID NO 165
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 165

Asn Gly Asp Ile Ser Leu Ala Tyr
1 5

<210> SEQ ID NO 166
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 166

Gly Asp Ile Ser Leu Ala Tyr Gly
1 5

<210> SEQ ID NO 167
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 167

Asp Ile Ser Leu Ala Tyr Gly Leu
1 5

<210> SEQ ID NO 168
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(8)
<223> OTHER INFORMATION: peptide

<400> SEQUENCE: 168

Ile Ser Leu Ala Tyr Gly Leu Arg
1 5

<210> SEQ ID NO 169
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 169

Val Asp Val Pro Asn Gly Asp
1 5

<210> SEQ ID NO 170
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 170

Asp Val Pro Asn Gly Asp Ile
1 5

<210> SEQ ID NO 171
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 171

Val Pro Asn Gly Asp Ile Ser
1 5

<210> SEQ ID NO 172
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 172

Pro Asn Gly Asp Ile Ser Leu
1 5

<210> SEQ ID NO 173
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 173

Asn Gly Asp Ile Ser Leu Ala
1 5

<210> SEQ ID NO 174
<211> LENGTH: 7

<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 174

Gly Asp Ile Ser Leu Ala Tyr
1               5

<210> SEQ ID NO 175
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 175

Asp Ile Ser Leu Ala Tyr Gly
1               5

<210> SEQ ID NO 176
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(7)
<223> OTHER INFORMATION: peptide

<400> SEQUENCE: 176

Ile Ser Leu Ala Tyr Gly Leu
1               5

<210> SEQ ID NO 177
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 177

Asp Val Pro Asn Gly Asp
1               5

<210> SEQ ID NO 178
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 178

Val Pro Asn Gly Asp Ile
1 5

<210> SEQ ID NO 179
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 179

Pro Asn Gly Asp Ile Ser
1 5

<210> SEQ ID NO 180
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 180

Asn Gly Asp Ile Ser Leu
1 5

<210> SEQ ID NO 181
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 181

Gly Asp Ile Ser Leu Ala
1 5

<210> SEQ ID NO 182
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(6)
<223> OTHER INFORMATION: peptide

<400> SEQUENCE: 182

Asp Ile Ser Leu Ala Tyr
1 5

<210> SEQ ID NO 183
<211> LENGTH: 6
<212> TYPE: PRT
<213> ORGANISM: Artificial
<220> FEATURE:
<223> OTHER INFORMATION: synthetic peptide
<220> FEATURE:

<221> NAME/KEY: MISC_FEATURE
<222> LOCATION: (1)..(6)
<223> OTHER INFORMATION: peptide

<400> SEQUENCE: 183

Ile Ser Leu Ala Tyr Gly
1 5

<210> SEQ ID NO 184
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 184

Val Pro Asn Gly Asp
1 5

<210> SEQ ID NO 185
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 185

Pro Asn Gly Asp Ile
1 5

<210> SEQ ID NO 186
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 186

Asn Gly Asp Ile Ser
1 5

<210> SEQ ID NO 187
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 187

Gly Asp Ile Ser Leu
1 5

<210> SEQ ID NO 188

<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 188

Asp Ile Ser Leu Ala
1               5

<210> SEQ ID NO 189
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 189

Ile Ser Leu Ala Tyr
1               5

<210> SEQ ID NO 190
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: peptide

<400> SEQUENCE: 190

Ser Leu Ala Tyr Gly
1               5

<210> SEQ ID NO 191
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: FOL-001, peptide

<400> SEQUENCE: 191

Val Asp Val Pro Asn Gly Arg Gly Asp Ser Leu Ala Tyr Gly Leu Arg
1               5                   10                  15

<210> SEQ ID NO 192
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: FOL-003, peptide

<400> SEQUENCE: 192

Gly Asp Pro Asn Asp Gly Arg Gly Asp Ser Val Val Tyr Gly Leu Arg
1 5 10 15

<210> SEQ ID NO 193
<211> LENGTH: 16
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(16)
<223> OTHER INFORMATION: FOL-037, peptide

<400> SEQUENCE: 193

Lys Pro Leu Ala Glu Asp Ile Ser Ile Glu Leu Ser Tyr Gly Ile Lys
1 5 10 15

<210> SEQ ID NO 194
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa=Glu or Gly
<220> FEATURE:
<221> NAME/KEY: MISC_FEATURE
<222> LOCATION: (3)..(3)
<223> OTHER INFORMATION: Xaa=Ser or Thr

<400> SEQUENCE: 194

Xaa Leu Xaa Tyr Gly Ile Lys
1 5

<210> SEQ ID NO 195
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa=Asp or Gly
<220> FEATURE:
<221> NAME/KEY: MISC_FEATURE
<222> LOCATION: (2)..(2)
<223> OTHER INFORMATION: Xaa=Ile or Gly
<220> FEATURE:
<221> NAME/KEY: MISC_FEATURE
<222> LOCATION: (4)..(4)
<223> OTHER INFORMATION: Xaa=Val or Leu
<220> FEATURE:
<221> NAME/KEY: MISC_FEATURE
<222> LOCATION: (5)..(5)
<223> OTHER INFORMATION: Xaa=Val or Ala

<400> SEQUENCE: 195

Xaa Xaa Ser Xaa Xaa Tyr Gly Leu Arg
1 5

<210> SEQ ID NO 196
<211> LENGTH: 25
<212> TYPE: PRT
<213> ORGANISM: Artificial
<220> FEATURE:
<223> OTHER INFORMATION: synthetic peptide
<220> FEATURE:

-continued

```
<221> NAME/KEY: MISC_FEATURE
<222> LOCATION: (1)..(25)
<223> OTHER INFORMATION: FOL-199, peptide

<400> SEQUENCE: 196

Gly Lys Tyr Gly Phe Tyr Thr His Val Phe Arg Leu Lys Lys Trp Ile
1               5                   10                  15

Gln Lys Val Ile Asp Gln Phe Gly Glu
            20                  25
```

PEPTIDES FOR USE IN SKIN AND HAIR PIGMENTATION

CROSS REFERENCE TO RELATED APPLICATIONS

This application is a U.S. national stage under 35 U.S.C. § 371 of PCT/EP2021/080032 filed Oct. 28, 2021, which claims priority to European application number 20204350.1 filed Oct. 28, 2020, the contents of which are hereby incorporated by reference in its entirety.

TECHNICAL FIELD

The present invention relates to peptides and use of said peptides in skin and hair pigmentation. Further, the present invention relates to a composition comprising said peptides for topical delivery.

BACKGROUND

The development of technology for safely increasing skin pigmentation has great commercial potential, both for cosmetic and public health policy-related purposes, given the well-appreciated risks of unprotected UVR exposure. Tanning via UV beds continues at high levels, despite significant health issues due to the damaging effects of UVA. Also, the chemical skin-tanning agents (stains) can leave the skin looking unnaturally orange or streaky, and some of the chemicals in use may not be fully compatible (in terms of safety) with subsequent UV radiation (UVR) exposure. Another market relating to skin pigmentation is that of skin lightening products. This is usually used to lighten dark areas of the skin, such as birth marks or dark patches (melasma). However, there are safety concerns over the existing products and their ingredients.

Preferably, skin pigmentation is modified via the topical administration route to avoid systemic effects. However, drug molecules larger than 600 Da normally have difficulties in permeating the skin. For polypeptides and peptides, the problem is accentuated even if the molecular weight is below 600 Da, since amino acids in general are too polar to penetrate the stratum corneum in an appropriate way, which is why most peptide- or protein-based drug are administered by parenteral formulations, which is undesirable for many purposes including targeting of topical, e.g. dermal disorders and diseases.

The polarity of many peptides is thus also problematic when attempting administration to hair follicles, e.g. for treating disorders or diseases associated with the hair follicle.

For a peptide to be biologically active, and prepared for parenteral administration, it typically needs to be dissolved in an aqueous solution, which often results in severe stability problems with undesired properties like decreased shelf life and loss of biological activity as effects.

Thus, there is a need for new, safe alternatives to UVR-induced 'sun-tan', and especially for stable, topical formulations which can deliver the active ingredient.

SUMMARY

The present inventors have identified a novel way of modulating melanin levels in human melanocytes. This involves mimicking some of the activity of a natural peptide that the inventors have previously reported to be involved in melanogenesis and melanin transfer. Skin darkening (such as tanning, age spots (solar lentigo) or in hyper-pigmentation following hormonal stimulation or skin trauma) involves the activation of melanocytes (pigment-producing cells) in skin. This activation within melanocytes results in the synthesis of more melanin and more transfer of this melanin to surrounding skin cells (keratinocytes) in human epidermis. By modulating this process it may be possible to increase or decrease natural skin colour.

The present invention offers a new and safer method of altering skin pigmentation, both by decreasing or increasing skin pigmentation.

In one aspect, the present invention relates to use of a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues, for non-therapeutic increase of melanin pigmentation of skin and/or hair of a subject.

In one aspect, the present invention relates to a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues, for use in the treatment a disease or disorder associated with hypopigmentation, such as selected from the group consisting of vitiligo, albinism, idiopathic guttate hypomelanosis, leprosy, leucism, phenylketonuria, *Pityriasis alba*, Angelman syndrome, *Tinea versicolor*, and yaws.

In one aspect, the present invention relates to a cosmetic method of darkening of skin and/or hair color, the method comprising administering to a subject a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues.

In one aspect, the present invention relates to a peptide or peptide derivative consisting of the amino acid sequence Asn-Ala-His-Met (SEQ ID NO: 2).

In one aspect, the present invention relates to a composition comprising:

a. a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues,
b. a saccharide or modified saccharide; and
c. a lipid.

In one aspect, the present invention relates to a peptide or peptide derivative consisting of the amino acid sequence Ala-Ala-His-Met (SEQ ID NO: 3).

In one aspect, the present invention relates to a composition comprising:

a. a peptide or peptide derivative comprising or consisting of the amino acid sequence of Ala-Ala-His-Met (SEQ ID NO: 3), wherein the peptide or peptide derivative comprises no more than 8 amino acid residues,
b. a saccharide or modified saccharide; and
c. a lipid.

In one aspect, the present invention relates to ise of a peptide or peptide derivative comprising the amino acid sequence of Ala-Ala-His-Met (SEQ ID NO: 3), wherein the peptide or peptide derivative comprises no more than 8 amino acid residues, or of the composition comprising said peptide or peptide derivative as described herein for non-therapeutic decrease of melanin pigmentation of skin and/or hair of a subject.

In one aspect, the present invention relates to a peptide or peptide derivative comprising the amino acid sequence of Ala-Ala-His-Met (SEQ ID NO: 3), wherein the peptide or peptide derivative comprises no more than 8 amino acid residues, or the composition comprising said peptide or peptide derivative as described herein, for use in the treatment of a disease or condition associated with hyperpigmentation, such as postinflammatory hyperpigmentation, chloasma, freckles, café au lait spots, and melanin hyperpigmentation, such as lentigo.

In one aspect, the present invention relates to a cosmetic method of lightening of skin and/or hair color, the method comprising administering to a subject a peptide or peptide derivative comprising or consisting of the amino acid sequence of Ala-Ala-His-Met (SEQ ID NO: 3), wherein the peptide or peptide derivative comprises no more than 8 amino acid residues, or a composition comprising said peptide or peptide derivative as described herein.

In another aspect, the present invention provides a method of manufacturing a composition as described herein, said method comprising the following steps:

a) mixing the peptide or peptide derivative with a saccharide or modified saccharide;
b) freeze drying the mixture of a);
c) mixing b) with a lipid and a surfactant;
d) grinding the mixture of c); and
e) optionally mixing the mixture of d) with a lipid and a thickener.

The effect of peptides 1 (SEQ ID NO: 2), 3 (SEQ ID NO: 3) and 4 (SEQ ID NO: 4) was tested on human skin equivalent samples (Example 1). The pigmentation of the skin samples from two different donors, (A) and (B), was macroscopically assessed by capturing high resolution images using the Olympus microscope camera, and the images were then processed using Image J & Paintshop Photo Pro software. In order to assess the change in pigmentation, the percentage increase/decrease of pixel area (measured in pixel intensity units) in comparison to vehicle control samples was calculated and visualised with standard error in (C) the first donor (all treatments, n=3 per treatment, 10 mg/ml) (D) a second donor (peptides 3 and 4, n=5) and (E) a third donor (all treatments, n=5).

Figure 2:
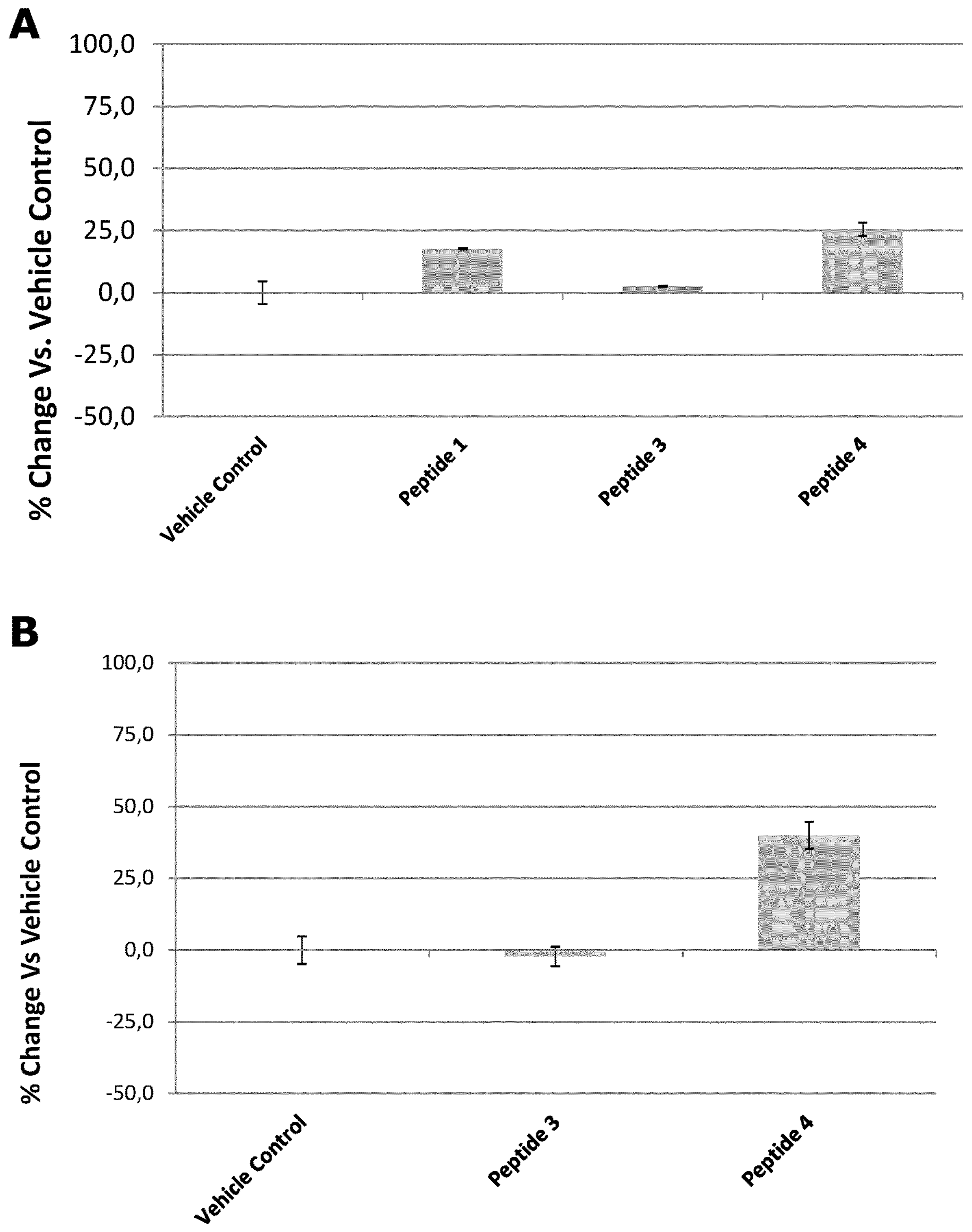

FIG. 2. Total melanin content assay

The total melanin content was determined in the skin equivalent samples (Example 3). Peptides 1 (SEQ ID NO: 2), 3 (SEQ ID NO: 3) and 4 (SEQ ID NO:4) were analysed following topical treatment of the SEs. In order to assess the change of total melanin content in the samples, the percentage increase/decrease of total melanin content of the SEs in comparison to vehicle control samples was calculated and visualised as mean+/−standard error (units=μg/ml melanin), for (A) the first donor (all treatments, 10 mg/ml, n=2 SEs per treatment) and B) the second donor (all treatments, 10 mg/ml, n=4 SEs per treatment) and (C) the third donor (all treatments, 10 mg/ml, n=7 SEs per treatment). The total melanin content of the skin equivalents were assessed at day 20 post treatment with the test peptides for two different donors and visualised with standard error in (D) (sample size n=7) and (E) sample size n=4).

FIG. 3. H&E and Warthin Starry Staining of Skin Equivalents Skin equivalent samples were stained with Warthin Starry and hematoxylin&eosin (H&E) in order to visualize and quantify the melanin distribution in the skin sections and to ensure that the histology of the skin equivalents was normal. Warthin Starry staining of skin equivalents, showing melanin distribution throughout layers of the epidermis in experiment 1 for the control vehicle, peptide 3 (SEQ ID NO: 3) and 4 (SEQ ID NO: 4) (A). Staining of skin equivalents in experiment 2 treated with peptide 1 (SEQ ID NO: 2) (B), peptide 4 (C), peptide 3 (D) and control vehicle (E).

Figure 4:
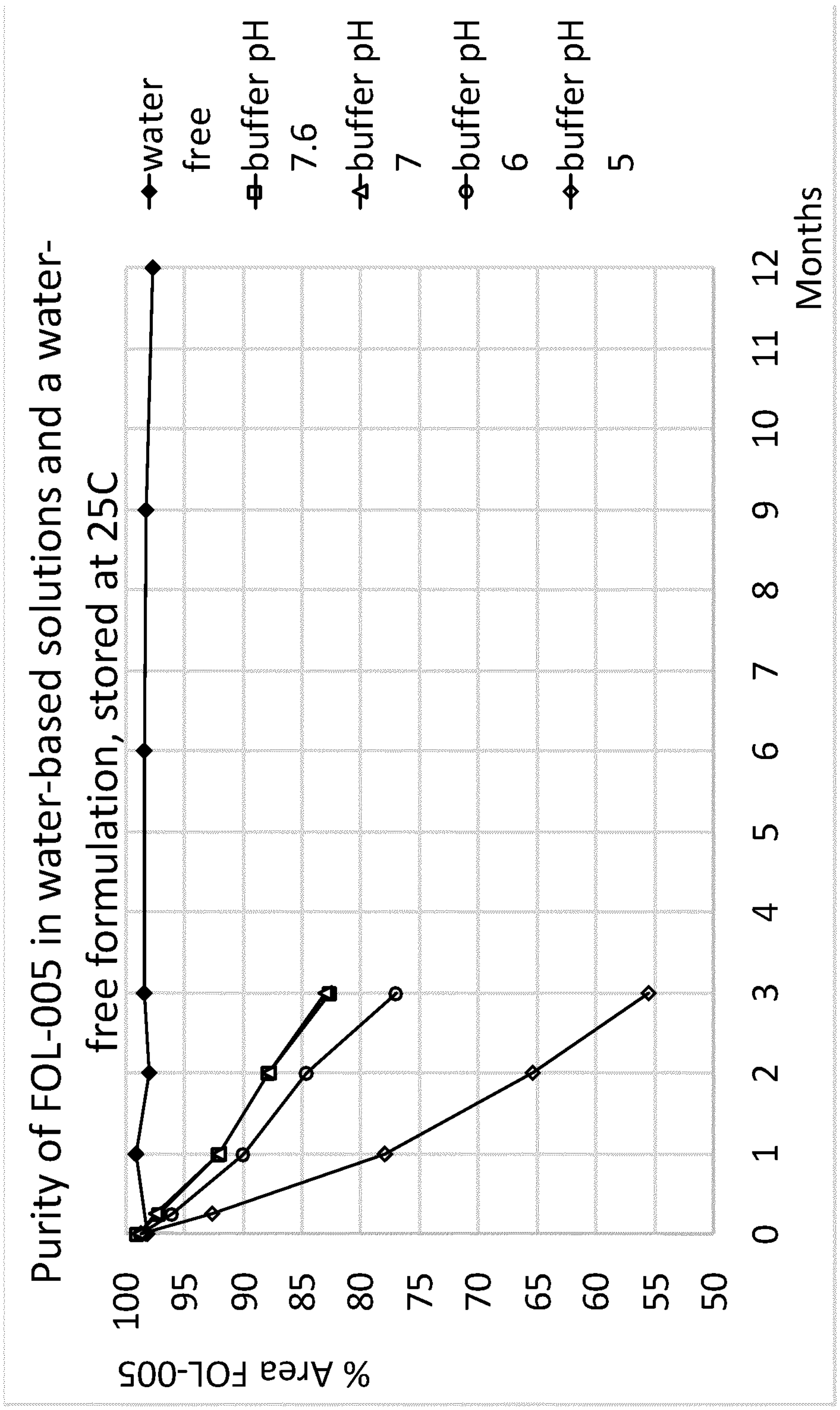

FIG. 4. Stability study—comparison of water-based solutions of FOL-005 and an essentially water free formulation FOL-005 lyophilized powder was dissolved in phosphate/citrate buffer of pHs 5, 6, 7 or 7.6. Samples of each formulation were analysed for purity using high-pressure liquid chromatography after up to 3 months of storage at 25° C. respectively. In addition, an essentially water-free formulation of FOL-005 was stored at 25° C. and samples were analysed for purity after up to 12 months of storage.

Figure 5:
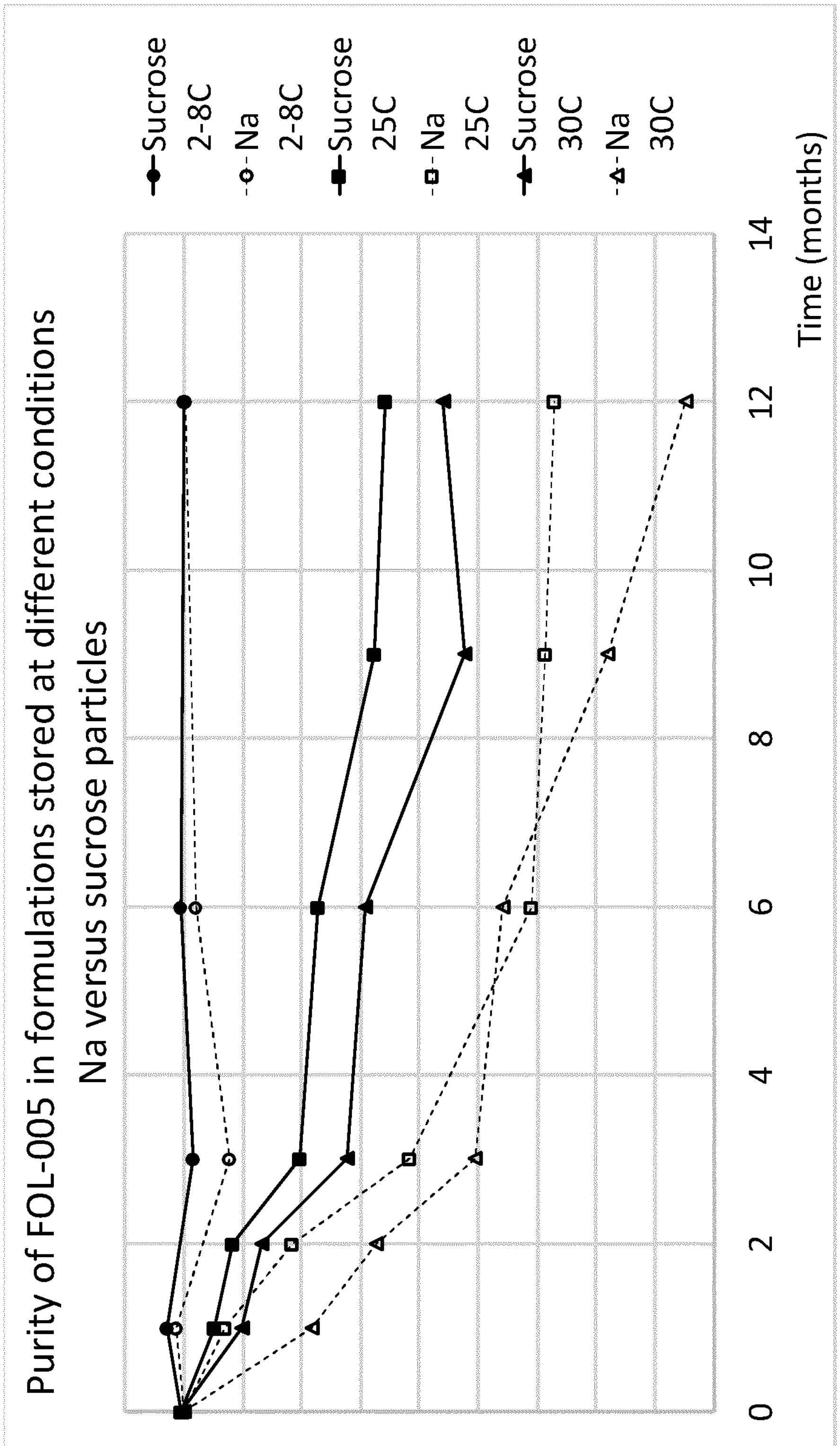

FIG. 5. Stability study—comparison of Na-FOL-005 and Na-FOL-005-Sucros

FOL-005/sucrose lyophilized powder was formulated to a suspension in dried or un-dried isopropyl myristate, paraffin oil/petrolatum, Sorbitan laurate and glyceryl behenate. Samples of each formulation were analysed for purity using high pressure liquid chromatography after up to 12 months of storage at 2-8, 25 and 30° C. respectively.

Figure 6:
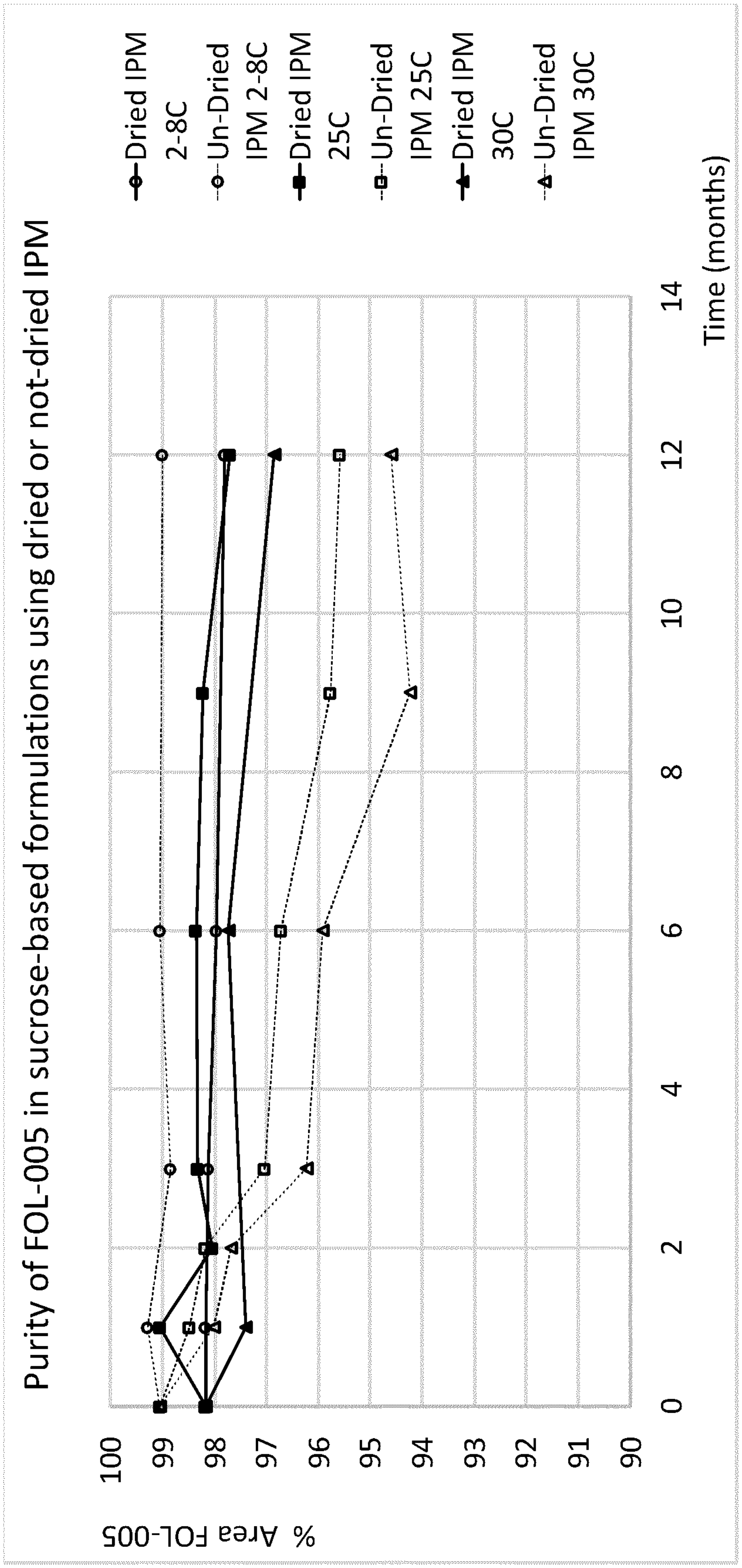

FIG. 6. Stability study—comparison of dried IPM and usual IPM

FOL-005/sucrose lyophilized powder was formulated to a suspension in dried or un-dried isopropyl myristate, paraffin oil/petrolatum, Sorbitan laurate and glyceryl behenate. Samples of each formulation were analysed for purity using high pressure liquid chromatography after up to 12 months of storage at 2-8, 25 and 30° C. respectively.

Figure 7:
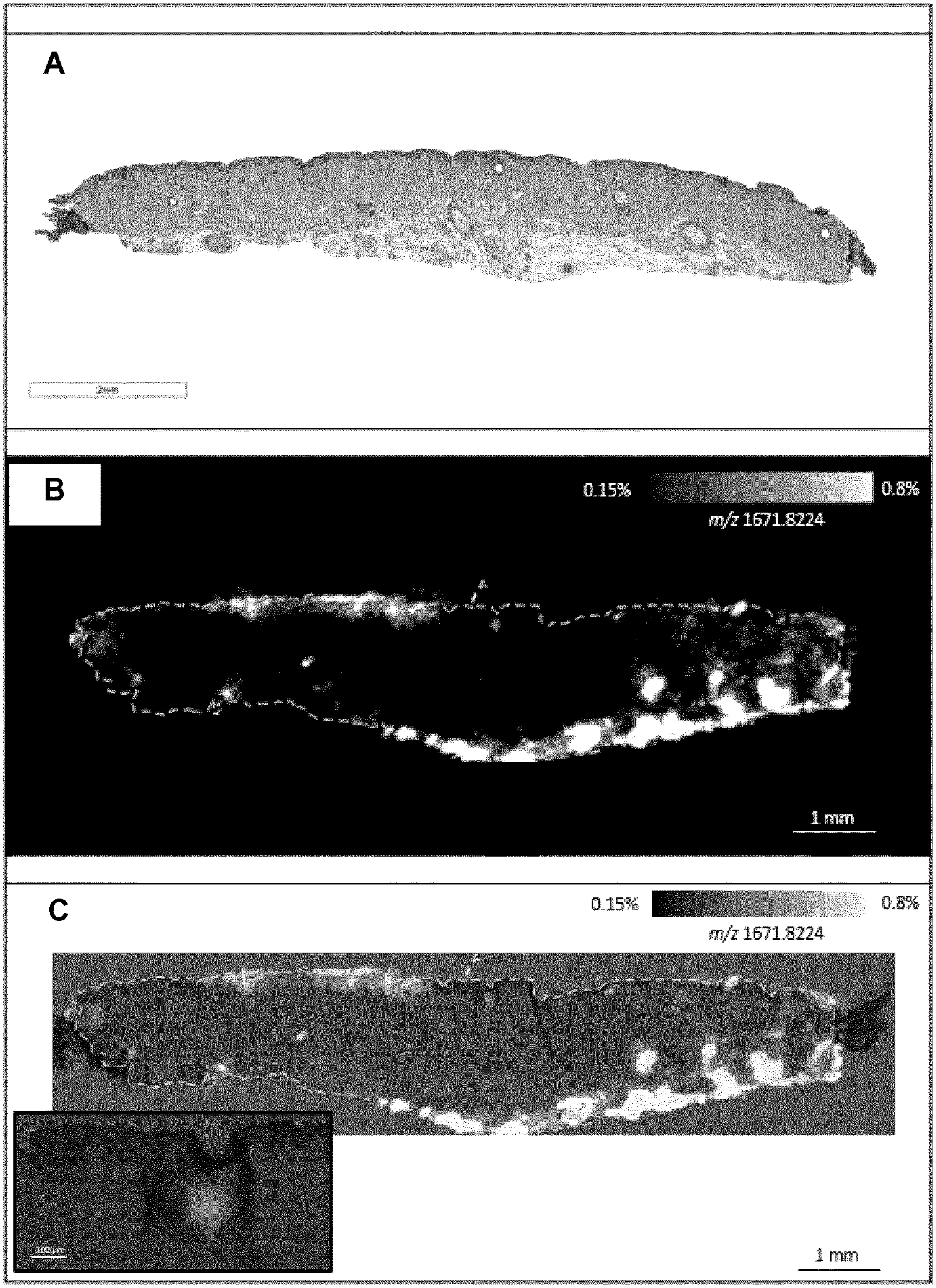

FIG. 7: Ex vivo study

FOL-005 distribution in pig inner ear skin section treated with FOL-005/sucrose formulation with isopropyl myristate, petrolatum, Sorbitan laurate and glyceryl behenate. The formulation was applied to the skin sample at 0 and 24 h. At 48 h the sample was frozen and subsequently sectioned and analysed using MALDI MSI. The concentration of FOL-005 is displayed in black-grey-white. White areas contain high concentration of FOL-005 and black areas contain low concentrations. A) H & E Staining (Adjacent Tissue Section), B) FOL-005 MSI Distribution in the treated tissue section, C) Overlay between the MSI Distribution and the H & E staining.

Figure 8:
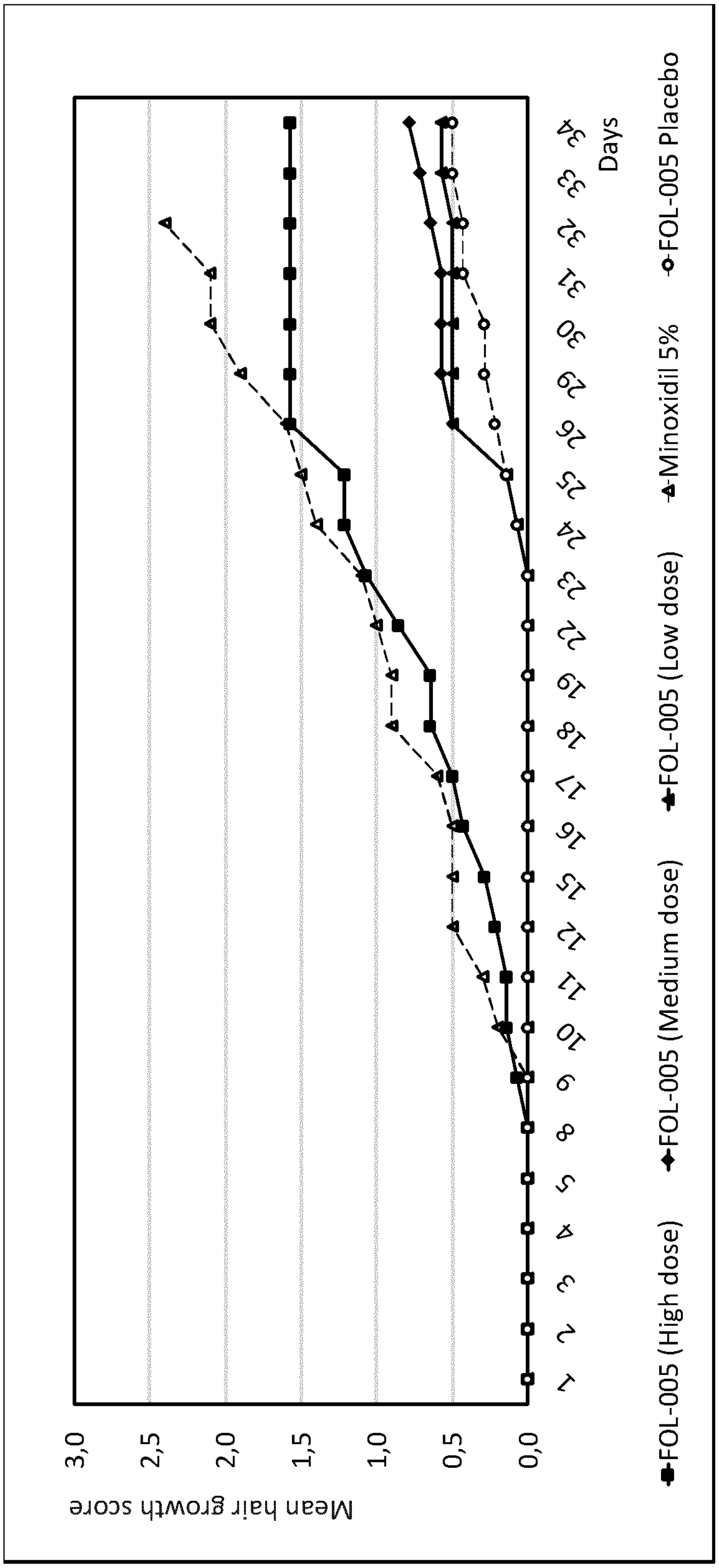

FIG. 8: In vivo efficacy study

C57Bl6 mice in stable telogen phase (age 6-9 weeks) were carefully clipped. Topical formulation of FOL-005 at three different strengths and placebo was applied at the clipped area once daily, 5 days per week until day 26. For comparison Minoxidil was administered to one group twice daily, 5 days per week until day 26. The hair growth was scored according to an established system, from 0 (no hair growth, pink skin) to 3 (dense, normal coat hair)

Figure 9:
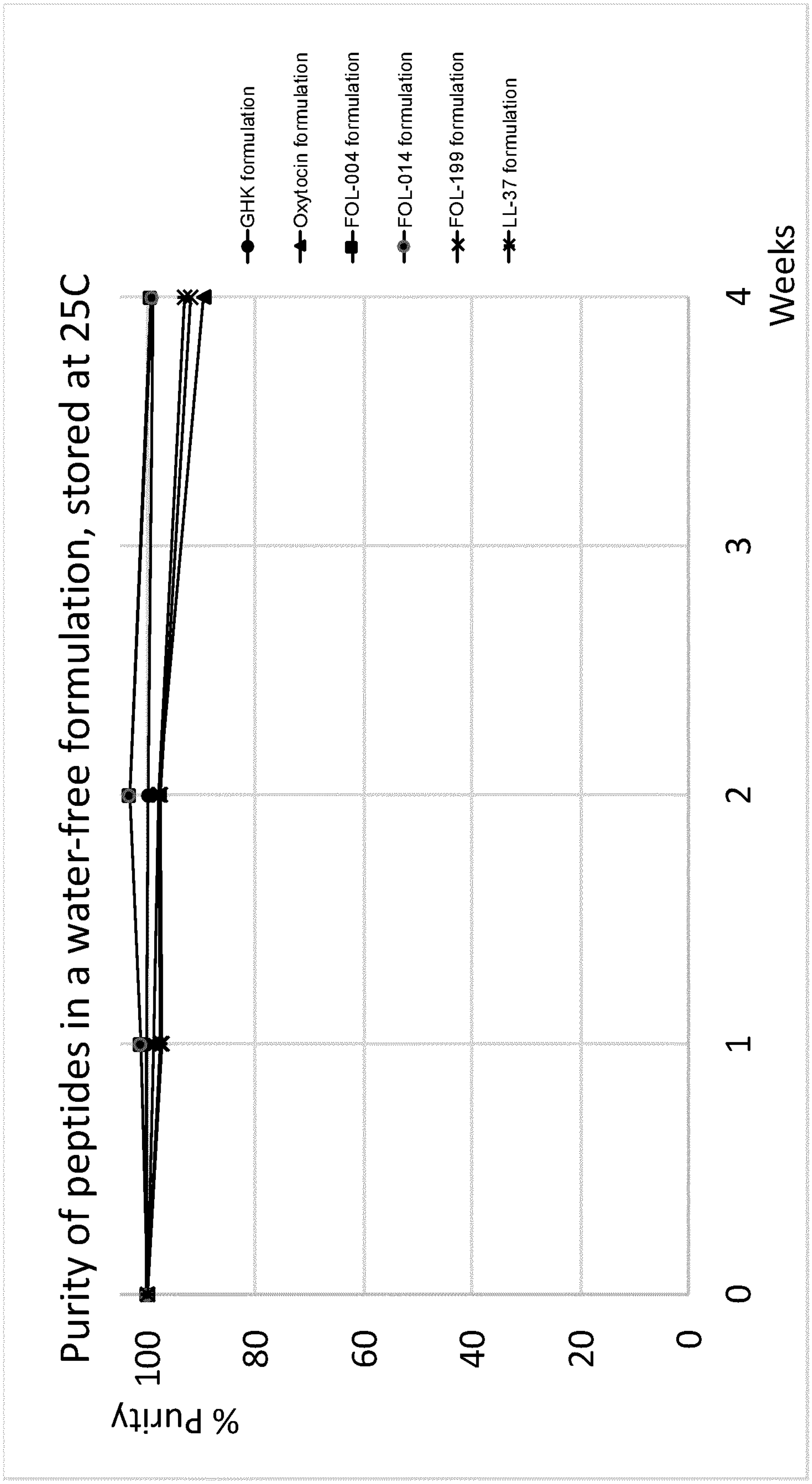

FIG. 9: Compositions comprising peptides

A) Stability of peptides in a water-free formulation (see Example 11). Water-free formulations of six peptides of different size and amino acid sequence were prepared. The concentration of the peptides was 0.2% and the following excipients and concentrations (w/w %) were used: Sucrose 0.4%, Span20 4%, Glyceryl behenate 3%, Isopropyl myristate 50% and petrolatum 42.4%. The formulations were stored at 20+/−5° C. and the peak purity was analysed using high pressure liquid chromatography at study start and after 1, 2 and 4 weeks of storage. B) Stability of oxytocin in a water-free formulation and in a PBS solution (see Example 11). A water-free formulation of oxytocin was prepared. The following excipients and concentrations (w/w %) were used: Oxytocin 0.2%, Sucrose 0.4%, Span20 4%, Glyceryl behenate 3%, Isopropyl myristate 50% and petrolatum 42.4%. In addition, a 0.2% solution of Oxytocin in PBS, pH 7.4 was prepared. The formulation and the solution were stored at 20+/−5° C. and the peak purity was analysed using high pressure liquid chromatography at study start and after 1, 2 and 4 weeks of storage. C) Stability of FOL-004 in a water-free formulation and in a PBS solution (see Example 11). A water-free formulation of FOL-004 was prepared. The following excipients and concentrations (w/w %) were used: FOL-004 0.2%, Sucrose 0.4%, Span20 4%, Glyceryl behenate 3%, Isopropyl myristate 50% and petrolatum 42.4%. In addition, a 0.2% solution of FOL-004 in PBS, pH 7.4 was prepared. The formulation and the solution were stored at 20+/−5° C. and the peak purity was analysed using high pressure liquid chromatography at study start and after 1, 2 and 4 weeks of storage.

Figure 10:
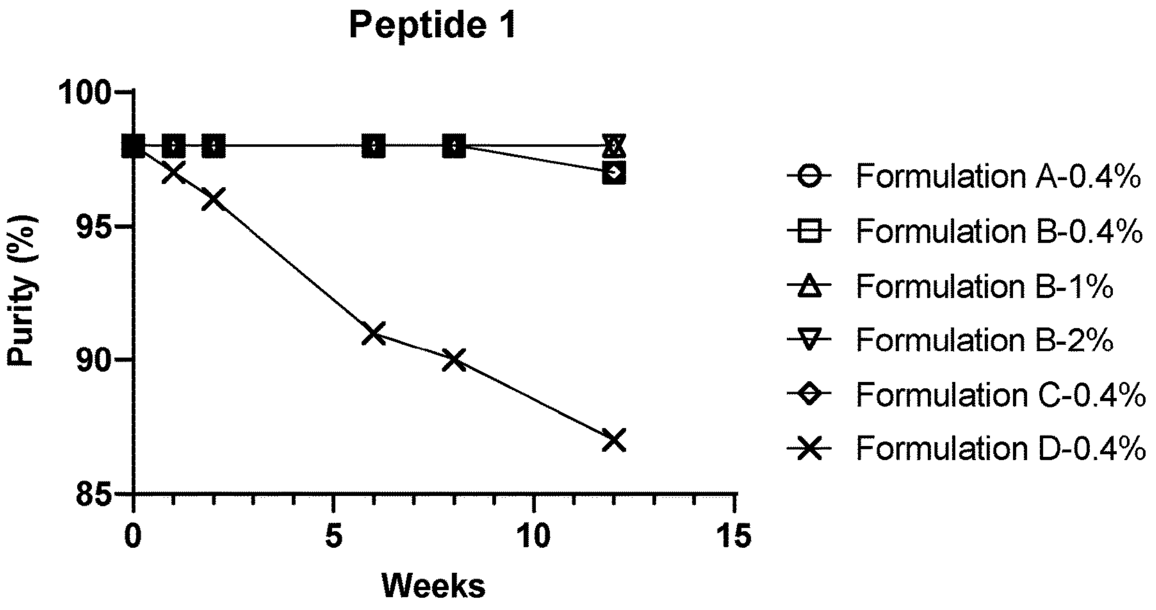
Figure 10:
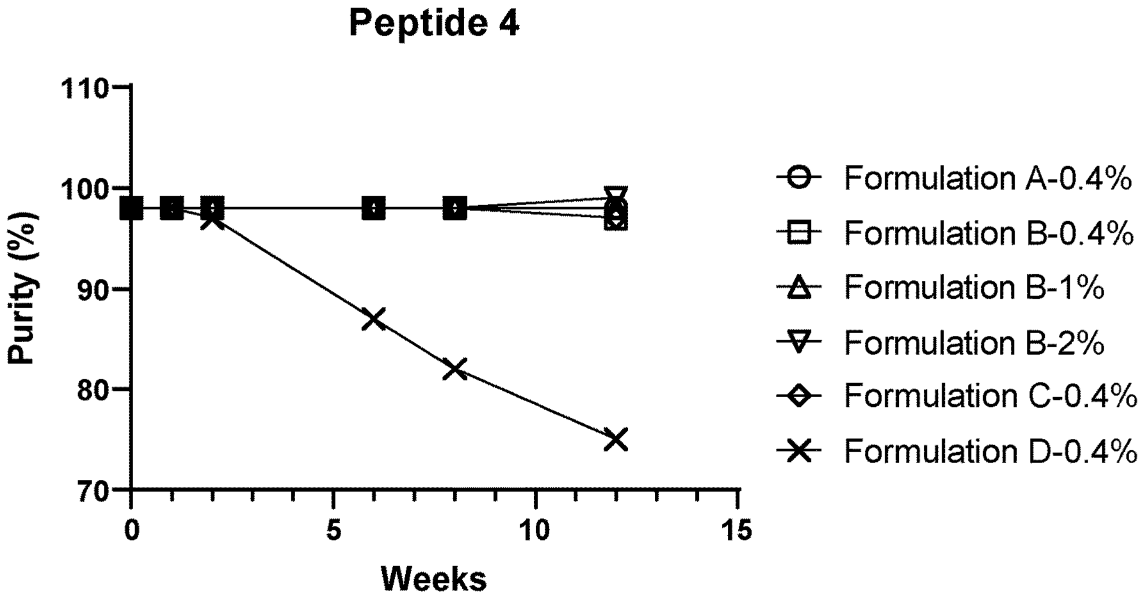

FIG. 10: Compositions comprising peptides

A) Purity of Peptide 1 (SEQ ID NO: 2) at 20° C. in three variations of a water-free formulation (see Example 12): A (peptide-sucrose dry powder mixed with premanufactured placebo and 0.4% peptide 1); B (suspension of peptide-sucrose dry powder and IPM mixed with ointment base containing 4% Span and 0.4%, 1% and 2% peptide 1); C (suspension of peptide-sucrose dry powder and IPM mixed with ointment base containing 2% Span and 0.4% peptide 1); and in a PBS solution D (peptide-sucrose dry powder dissolved in PBS. 0.4%, peptide 1). B) Purity of Peptide 4 (SEQ ID NO: 4) at 20° C. in three variations of a water-free formulation (see Example 12): A (peptide-sucrose dry powder mixed with premanufactured placebo and 0.4% peptide 4); B (suspension of peptide-sucrose dry powder and IPM mixed with ointment base containing 4% Span and 0.4%, 1% and 2% peptide 4); C (suspension of peptide-sucrose dry powder and IPM mixed with ointment base containing 2% Span and 0.4% peptide 4); and in a PBS solution D (peptide-sucrose dry powder dissolved in PBS. 0.4%, peptide 4).

Figure 11:
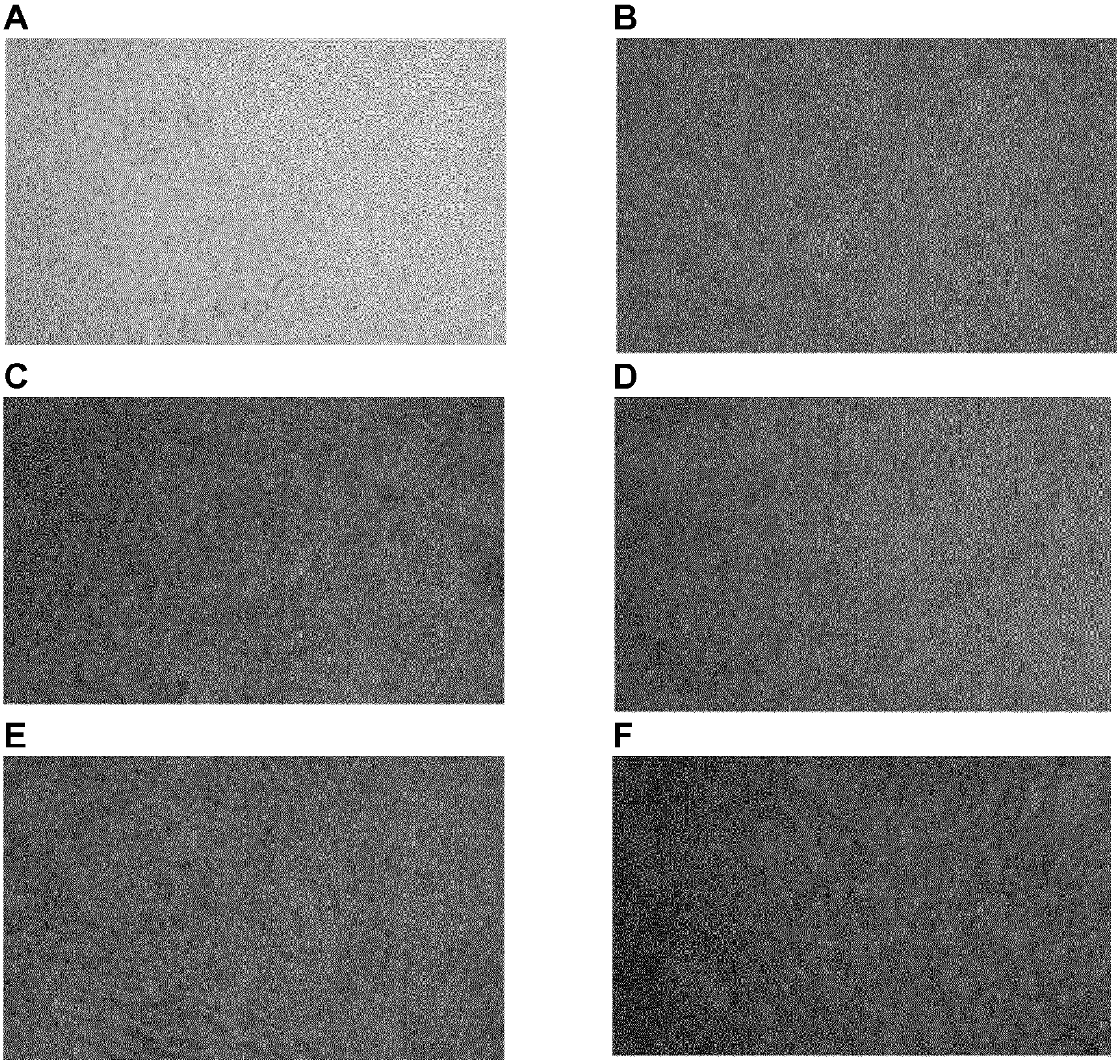
Figure 11:
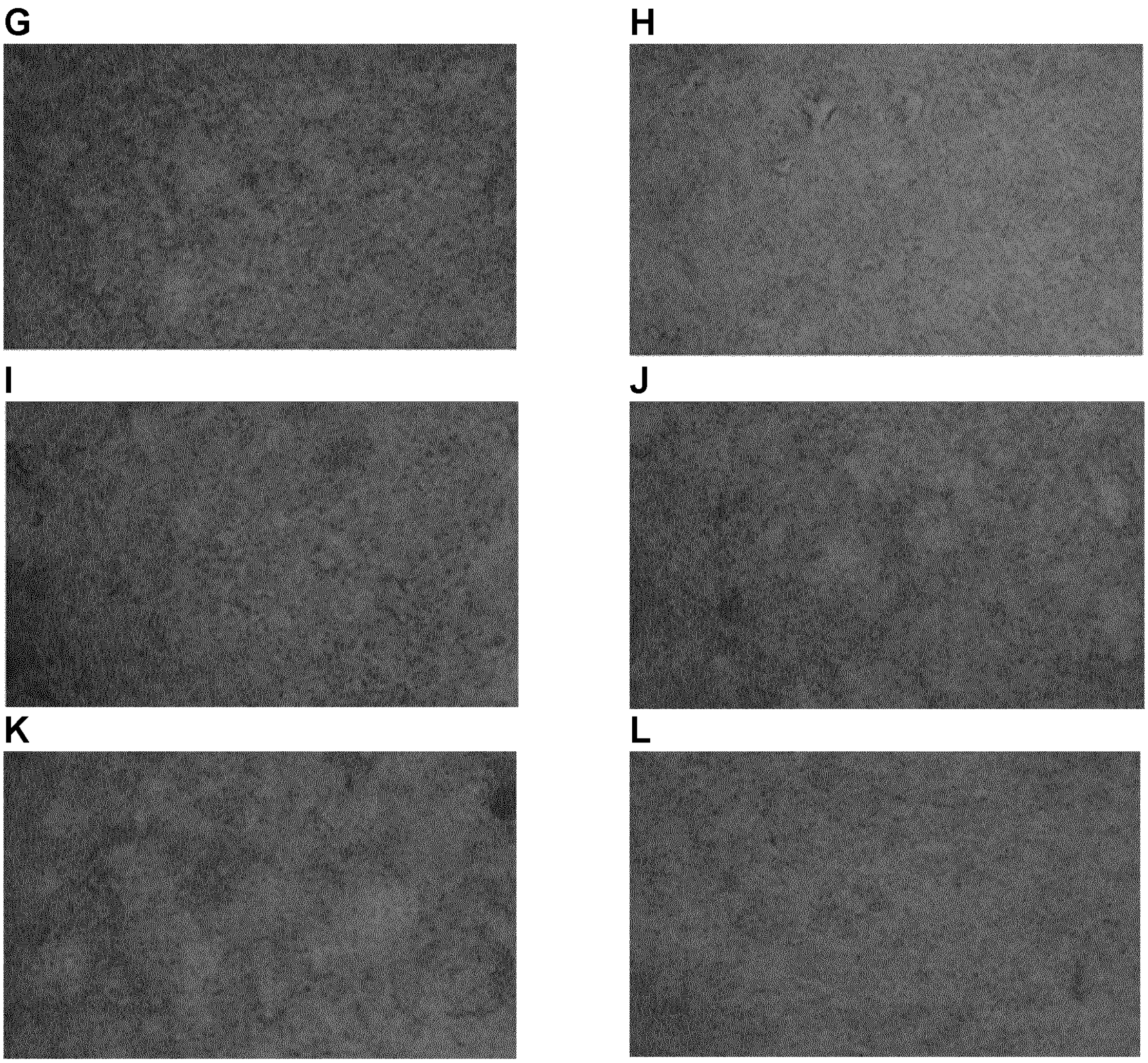

FIG. 11. Selected images showing the effect of peptides 1 and 4 in formulation B when tested on Melanoderm skin equivalent samples The pigmentation of the epidermis in Example 13 was macroscopically assessed by capturing high resolution images using the Olympus microscope camera (×10 magnification). A) Melanoderm day 0 prior to treatment; B) Untreated control (sterile water) day 7; C) formulation B vehicle control day 7; D) 1 μM synthetic α-MSH analogue ([Nle$^4$,D-Phe$^7$]-α-MSH) positive control day 7; E) 0.4% Peptide 1 in formulation B; F) 1% Peptide 1 in formulation B; G) 2% Peptide 1 in formulation B; H) Peptide 1 in water (10 mg/ml); I) 0.4% Peptide 4 in formulation B; J) 1% Peptide 4 in formulation B; K) 2% Peptide 4 in formulation B; and L) Peptide 4 in water (10 mg/ml).

Figure 12:
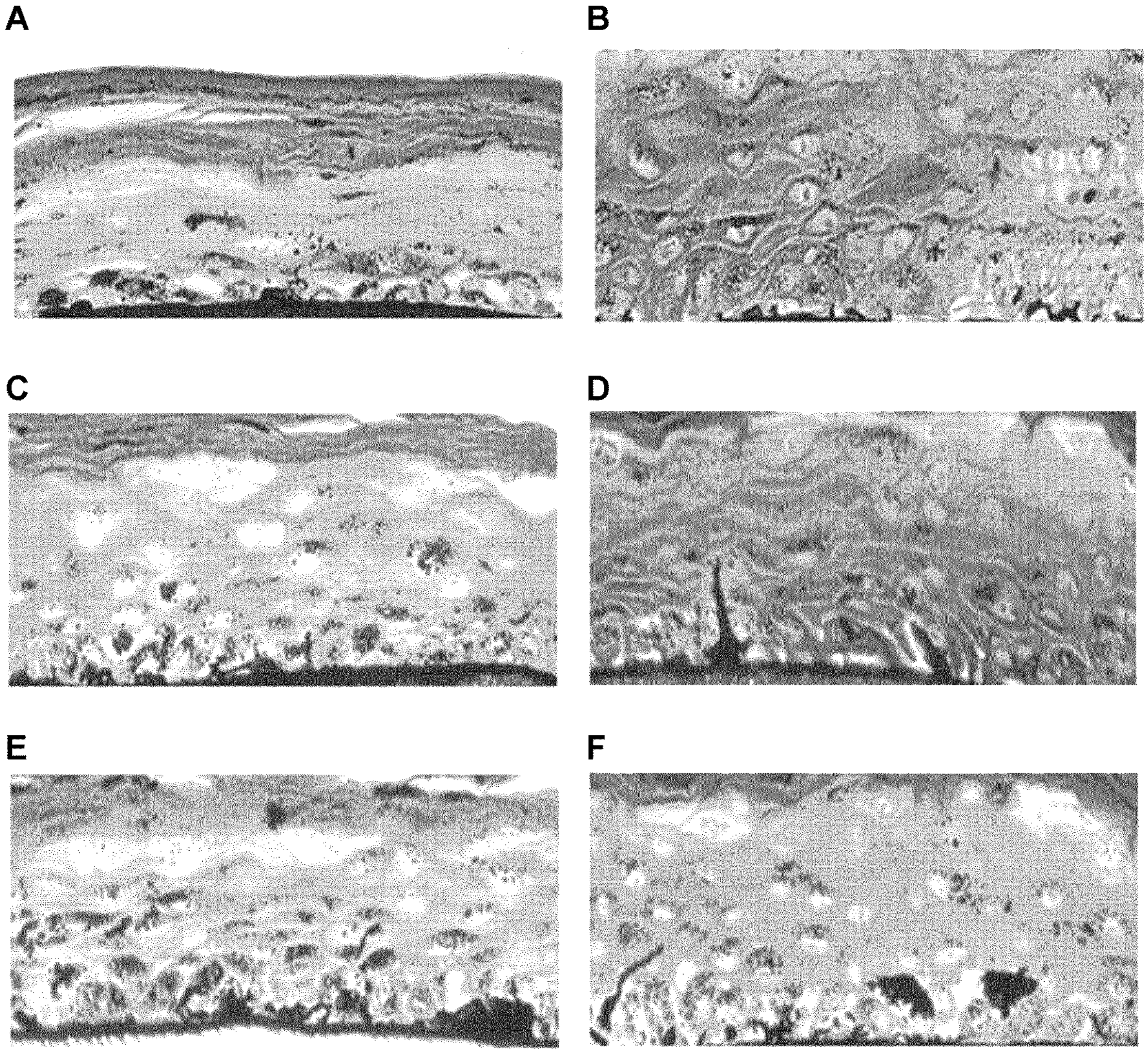
Figure 12:
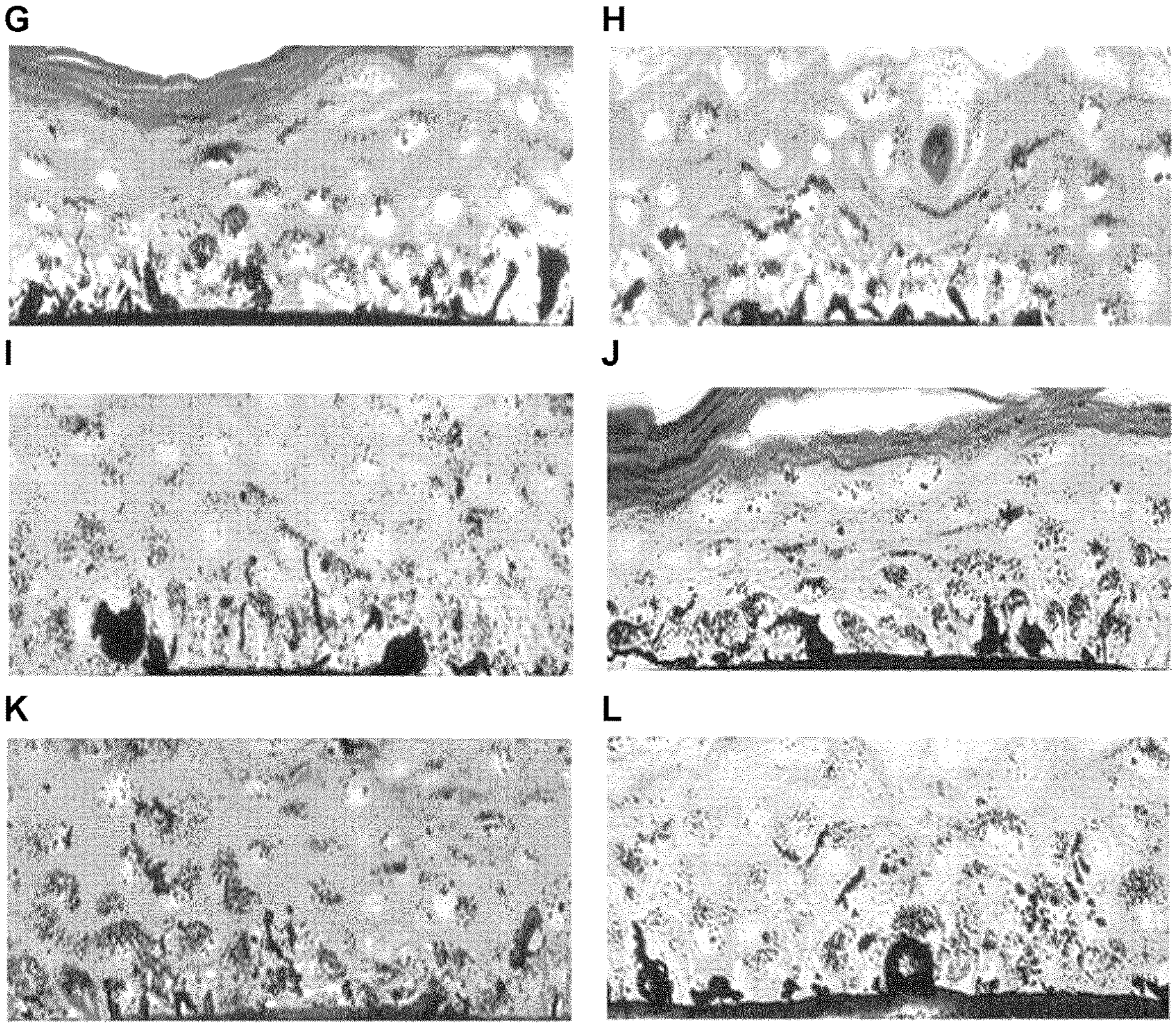

FIG. 12. Selected images of Warthin-Starry stained tissue sections showing the effect of peptides 1 and 4 in formulation B when tested on Melanoderm skin equivalent samples.

Skin equivalent samples were sectioned and stained with Warthin-Starry to visualize and quantify the melanin distribution in the epidermis. Images were captured at ×20 magnification and processed in ImageJ software (Example 14). A) Melanoderm day 0 prior to treatment; B) Untreated control (sterile water) day 7; C) formulation B vehicle control day 7; D) 1 μM synthetic α-MSH analogue ([Nle$^4$, D-Phe$^7$]-α-MSH) positive control day 7; E) 0.4% Peptide 1 in formulation B; F) 1% Peptide 1 in formulation B; G) 2% Peptide 1 in formulation B; H) Peptide 1 in water (10 mg/ml); I) 0.4% Peptide 4 in formulation B; J) 1% Peptide 4 in formulation B; K) 2% Peptide 4 in formulation B; and L) Peptide 4 in water (10 mg/ml).

Figure 13:
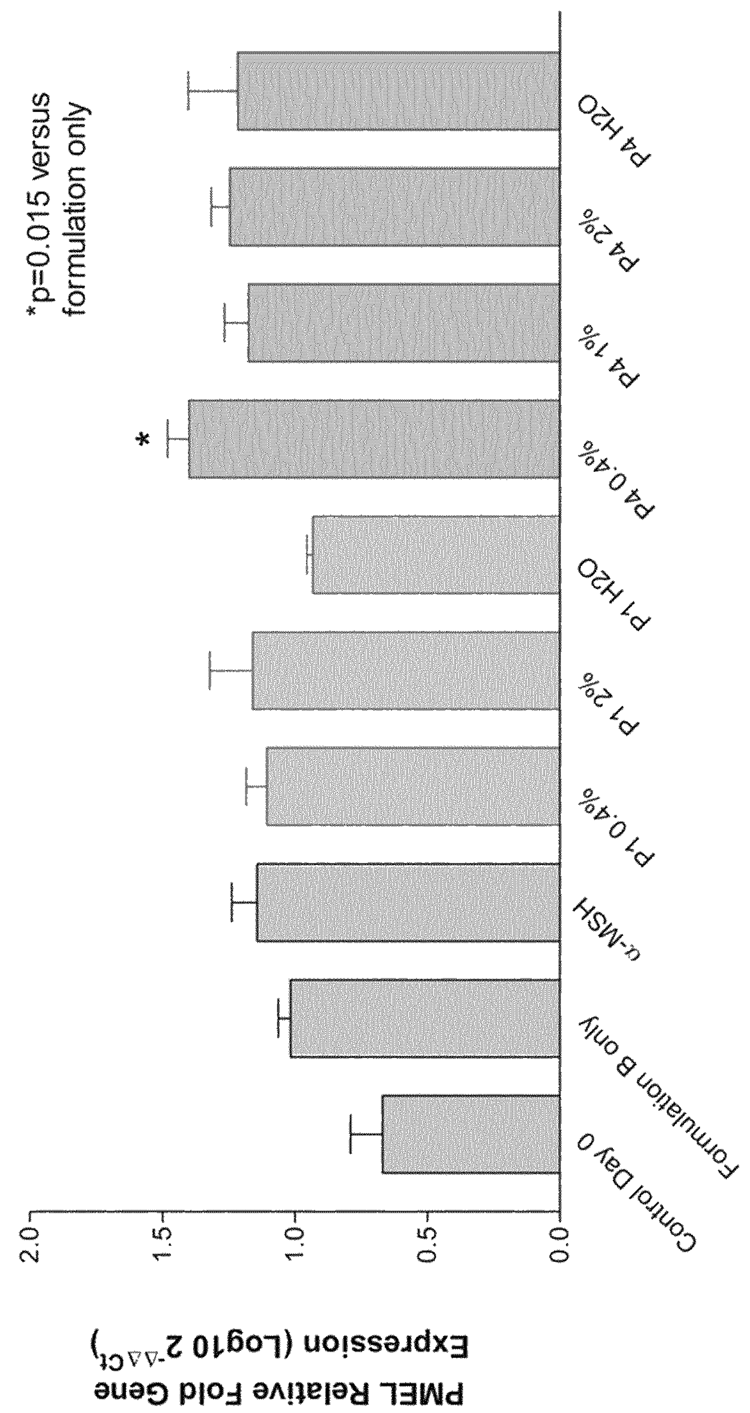
Figure 13:
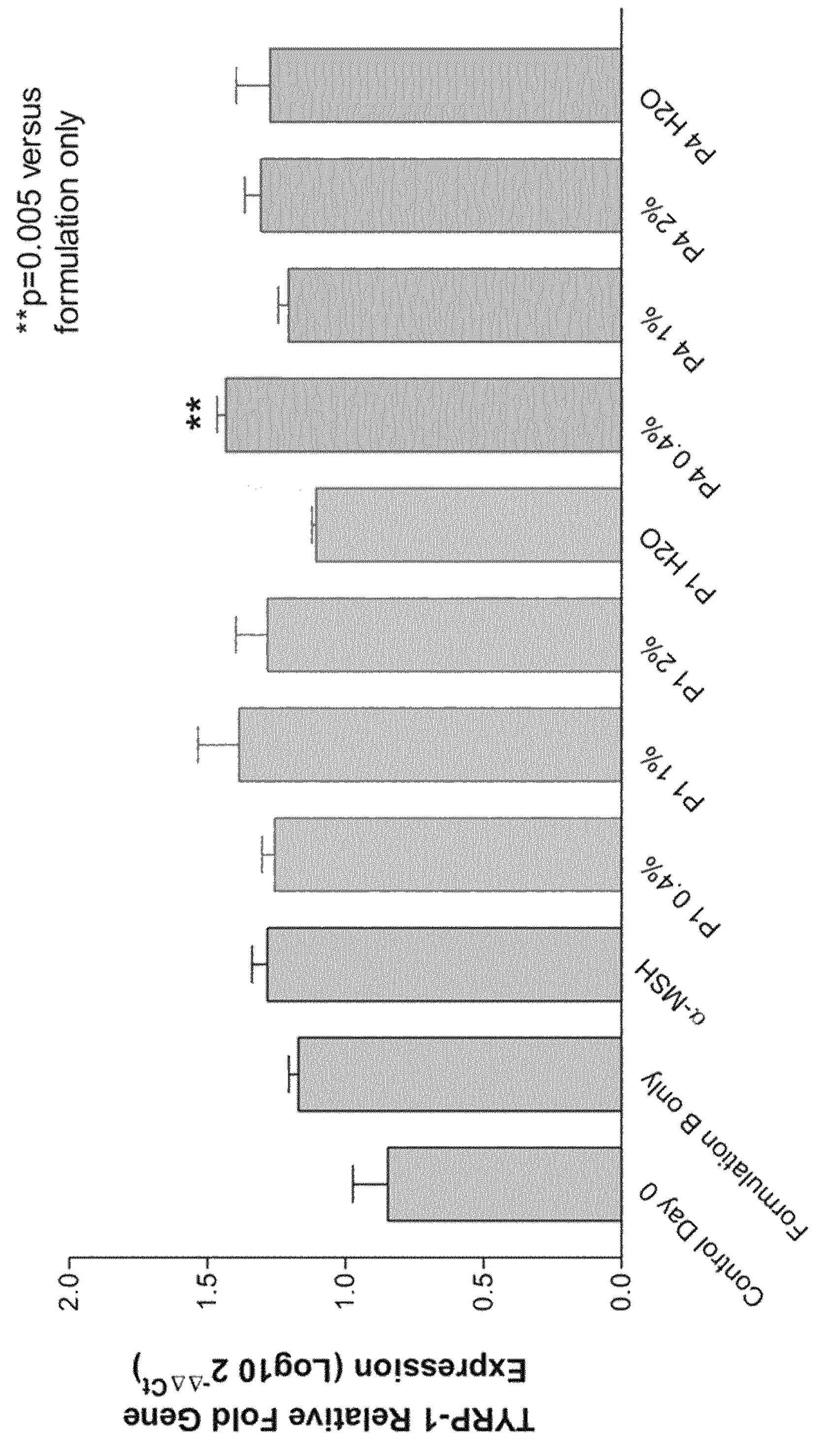
Figure 13:
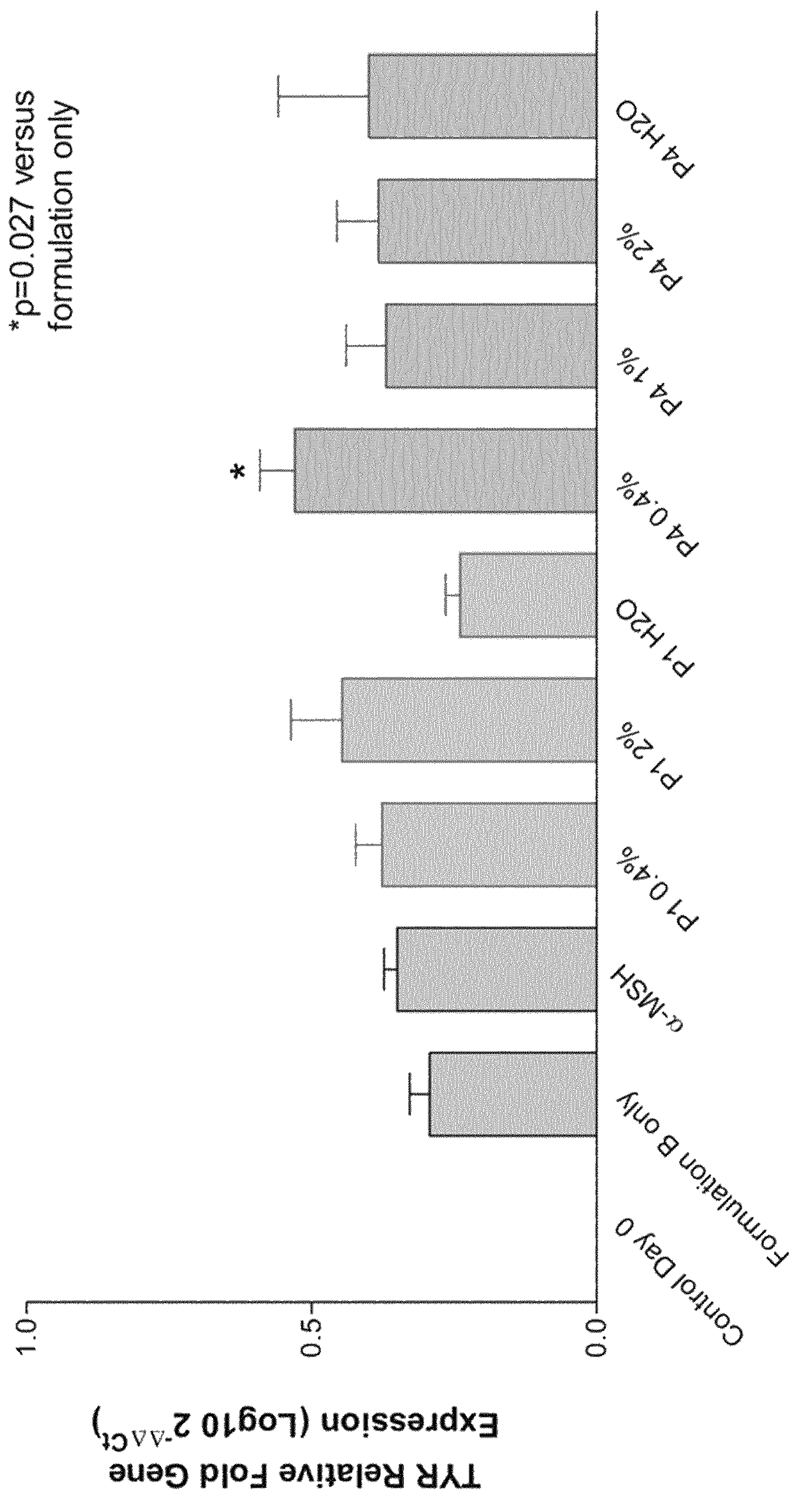

FIG. 13. Graph showing relative expression of PMEL in Melanoderms after treatment with peptides 1 and 4 in formulation B using qPCR analysis.

A) Graph showing relative expression of PMEL in Melanoderms after treatment with peptides 1 and 4 in formulation B using qPCR analysis (Example 15). cDNA from SEs was amplified with prevalidated primers for PMEL and relative PMEL expression calculated against untreated control samples on day 7 using the ΔΔCt method and the formula Log 10 ($2^{-\Delta\Delta C_t}$). RPS20 was used as a reference control (housekeeping gene). Bars from left to right: Melanoderm day 0 prior to treatment; Formulation B vehicle control day 7; 1 μM synthetic α-MSH analogue ([Nle$^4$,D-Phe$^7$]-α-MSH) positive control day 7; 0.4% Peptide 1 in formulation B; 2% Peptide 1 in formulation B; Peptide 1 in water (10 mg/ml); 0.4% Peptide 4 in formulation B; 1% Peptide 4 in formulation B; 2% Peptide 4 in formulation B; and Peptide 4 in water (10 mg/ml). Error bars show SEM. Statistical analysis, unpaired t-test.

B) Graph showing relative expression of TYRP-1 in Melanoderms after treatment with peptides 1 and 4 in formulation B using qPCR analysis (Example 15). cDNA from SEs was amplified with prevalidated primers for TYRP-1 and relative TYRP-1 expression calculated against untreated control samples on day 7 using the ΔΔCt method and the formula Log 10 ($2^{-\Delta\Delta C_t}$). RPS20 was used as a reference control (housekeeping gene). Bars from left to right: Melanoderm day 0 prior to treatment; Formulation B vehicle control day 7; 1 μM synthetic α-MSH analogue ([Nle$^4$,D-Phe$^7$]-α-MSH) positive control day 7; 0.4% Peptide 1 in formulation B; 1% Peptide 1 in formulation B; 2% Peptide 1 in formulation B; Peptide 1 in water (10 mg/ml); 0.4% Peptide 4 in formulation B; 1% Peptide 4 in formulation B; 2% Peptide 4 in formulation B; and Peptide 4 in water (10 mg/ml). Error bars show SEM. Statistical analysis, unpaired t-test.

C) Graph showing relative expression of Tyrosinase (TYR) in Melanoderms after treatment with peptides 1 and 4 in formulation B using qPCR analysis (Example 15). cDNA from SEs was amplified with prevalidated primers for TYR and relative TYR expression calculated against untreated control samples on day 7 using the ΔΔCt method and the formula Log 10 ($2^{-\Delta\Delta C_t}$). RPS20 was used as a reference control (housekeeping gene). Bars from left to right: Melanoderm day 0 prior to treatment; Formulation B vehicle control day 7; 1 μM synthetic α-MSH analogue ([Nle$^4$,D-Phe$^7$]-α-MSH) positive control day 7; 0.4% Peptide 1 in formulation B; 1% Peptide 1 in formulation B; 2% Peptide 1 in formulation B; Peptide 1 in water (10 mg/ml); 0.4% Peptide 4 in formulation B; 1% Peptide 4 in formulation B; 2% Peptide 4 in formulation B; and Peptide 4 in water (10 mg/ml). Error bars show SEM. Statistical analysis, t-test.

DETAILED DESCRIPTION

The Peptide

The term 'peptide' as used herein refers to a molecule comprising two or more amino acid residues joined to each other by peptide bonds. The terms 'peptide' and 'polypeptide' are used herein interchangeably throughout. In one embodiment, the term 'peptide' also includes peptide derivatives.

In one aspect, the present invention relates to a peptide or peptide derivate comprising the amino acid sequence of Ala-Xaa2-Met, wherein Xaa2 is His or Ala.

In one embodiment, the peptide or peptide derivative comprises the amino acid sequence of Xaa1-Ala-Xaa2-Met (SEQ ID NO: 13), wherein Xaa1 is Asn or Ala, and Xaa2 is His or Ala. In one embodiment, the peptide or peptide derivative comprises the amino acid sequence of Asn-Ala-Xaa2-Met (SEQ ID NO: 1), wherein Xaa2 is His or Ala.

In one embodiment, the amino acid sequence of Asn-Ala-Xaa2-Met (SEQ ID NO: 1) is Asn-Ala-His-Met (SEQ ID NO: 2). In one embodiment, the amino acid sequence of Asn-Ala-Xaa2-Met (SEQ ID NO: 1) is Asn-Ala-Ala-Met (SEQ ID NO: 4).

In one embodiment, the peptide or peptide derivative comprises the amino acid sequence Asn-Ala-His-Met (SEQ ID NO: 2). In one embodiment, the peptide consists of the amino acid sequence Asn-Ala-His-Met (SEQ ID NO: 2). In one embodiment, peptide derivative consists of the amino acid sequence Asn-Ala-His-Met (SEQ ID NO: 2), i.e. consisting of the sequence Asn-Ala-His-Met (SEQ ID NO: 2) which is modified or derivitized as disclosed herein. In one embodiment, the peptide or peptide derivative comprises the amino acid sequence Ala-Ala-His-Met (SEQ ID NO: 3). In one embodiment, the peptide consists of the amino acid sequence Ala-Ala-His-Met (SEQ ID NO: 3). In one embodiment, the peptide derivative consists of the amino acid sequence Ala-Ala-His-Met (SEQ ID NO: 3), i.e. consisting of the sequence Ala-Ala-His-Met (SEQ ID NO: 3) which is modified or derivitized as disclosed herein. In one embodiment, the peptide or peptide derivative comprises the amino acid sequence Asn-Ala-Ala-Met (SEQ ID NO: 4). In one embodiment, the peptide consists of the amino acid sequence Asn-Ala-Ala-Met (SEQ ID NO: 4). In one embodiment, the peptide derivative consists of the amino acid sequence Asn-Ala-Ala-Met (SEQ ID NO: 4) which is modified or derivitized as disclosed herein. In one embodiment, the peptide comprises or consists of the amino acid sequence Ala-His-Met.

The term 'peptide derivative' as used herein relates to a peptide which is modified or derivatized. In one embodiment, the peptide derivative is a peptide as disclosed herein which is conjugated to a moiety, such as a moiety selected from the group consisting of polyethylene glycol (PEG), monosaccharides, fluorophores, chromophores, radioactive compounds, and cell-penetrating peptides. In one embodiment, the peptide is glycosylated.

In one embodiment, the peptide derivative is a peptide as disclosed herein which is modified by being glycosylated or by PEGylation, amidation, esterification, acylation, acetylation and/or alkylation.

In one embodiment, the peptide derivative is a peptide as disclosed herein which is fused to another polypeptide, such as a polypeptide selected from the group consisting of glutathione-S-transferase (GST) and protein A, or to a tag.

The term 'amino acid' as used herein includes the standard twenty genetically-encoded amino acids and their corresponding stereoisomers in the 'D' form (as compared to the natural 'L' form), omega-amino acids and other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for peptides of the present invention, as long as the desired functional property is retained by the peptide. For the peptides shown, each encoded amino acid residue, where appropriate, is represented by a single letter designation, corresponding to the trivial name of the conventional amino acid.

In accordance with convention, the amino acid sequences disclosed herein are provided in the N-terminus to C-terminus direction.

In one embodiment, the peptide comprises no more than 20 amino acid residues, such as no more than 15 amino acid residues, such as no more than 14 amino acid residues, such as no more than 13 amino acid residues, such as no more than 12 amino acid residues, such as no more than 11 amino acid residues, such as no more than 10 amino acid residues, such as no more than 9 amino acid residues, such as no more than 8 amino acid residues, such as no more than 7 amino acid residues, such as no more than 6 amino acid residues, such as no more than 5 amino acid residues, such as no more than 4 amino acid residues, such as no more than 3 amino acid residues.

In one embodiment, the peptide comprises no more than 20 amino acid residues and the peptide is conjugated to a moiety as described above. Thus, in one embodiment, the peptide is conjugated to a moiety comprising amino acid residues, such as a cell-penetrating peptide, and the peptide and the conjugated moiety may then in total comprise more than 20 amino acid residues. In one embodiment, the peptide is fused to another polypeptide, such as a polypeptide selected from the group consisting of glutathione-S-transferase (GST) and protein A, or to a tag. In one embodiment, the peptide is fused to another polypeptide, such as to an additional peptide as described herein below. In one embodiment, when the peptide is fused to another polypeptide, the peptide and the polypeptide may in total comprise more than 20 amino acid residues. In one embodiment, the peptide and the conjugated moiety or polypeptide in total comprises no more than 100 amino acid residues, such as no more than 75 amino acid residues, such as no more than 50 amino acid residues, such as no more than 40 amino acid residues, such as no more than 30 amino acid residues, such as no more than 25 amino acid residues.

In one embodiment, the peptide comprises at least 4 amino acid residues, such as at least 5 amino acid residues, such as at least 6 amino acid residues, such as at least 7 amino acid residues, such as at least 8 amino acid residues, such as at least 9 amino acid residues, such as at least 10 amino acid residues, such as at least 11 amino acid residues, such as at least 12 amino acid residues, such as at least 15 amino acid residues.

In one embodiment, the peptide or peptide derivative consists of an amino acid sequence of 4 amino acid residues. In one embodiment, the peptide or peptide derivative consists of an amino acid sequence of 5 amino acid residues. In one embodiment, the peptide or peptide derivative consists of an amino acid sequence of 6 amino acid residues. In one embodiment, the peptide or peptide derivative consists of an amino acid sequence of 7 amino acid residues. In one embodiment, the peptide or peptide derivative consists of an amino acid sequence of 8 amino acid residues.

In one embodiment, the peptide comprises or consists of tandem repeats. In one embodiment, the peptide is cyclic.

In embodiment, the peptide is selected from the group consisting of Asn-Ala-His-Met (SEQ ID NO: 2), Ala-Ala-His-Met (SEQ ID NO: 3), Asn-Ala-Ala-Met (SEQ ID NO: 4) and Ala-His-Met. In one embodiment, the peptide consists of an amino acid sequence selected from the group consisting of Asn-Ala-His-Met (SEQ ID NO: 2), Ala-Ala- His-Met (SEQ ID NO: 3), Asn-Ala-Ala-Met (SEQ ID NO: 4) and Ala-His-Met, and the peptide is conjugated to a moiety, such as a moiety selected from the group consisting of polyethylene glycol (PEG), monosaccharides, fluorophores, chromophores, radioactive compounds, and cell-penetrating peptides. In one embodiment, the peptide consists of an amino acid sequence selected from the group consisting of Asn-Ala-His-Met (SEQ ID NO: 2), Ala-Ala-His-Met (SEQ ID NO: 3), Asn-Ala-Ala-Met (SEQ ID NO: 4) and Ala-His-Met, and said peptide is modified by being glycosylated or by PEGylation, amidation, esterification, acylation, acetylation and/or alkylation. In one embodiment, the peptide consists of an amino acid sequence selected from the group consisting of Asn-Ala-His-Met (SEQ ID NO: 2), Ala-Ala-His-Met (SEQ ID NO: 3), Asn-Ala-Ala-Met (SEQ ID NO: 4) and Ala-His-Met, and said peptide is fused to another polypeptide, such as a polypeptide selected from the group consisting of glutathione-S-transferase (GST) and protein A, or to a tag.

In one embodiment, the peptide or peptide derivative retains the same function as Asn-Ala-Ala-Met (SEQ ID NO: 4). In one embodiment, the peptide or peptide derivative retains the increasing melanin pigmentation activity of Asn-Ala-Ala-Met (SEQ ID NO: 4). In one embodiment, the peptide or peptide derivative retains the increasing melanin pigmentation activity of Asn-Ala-His-Met (SEQ ID NO: 2). In one embodiment, the peptide or peptide derivative retains the same function as Asn-Ala-His-Met (SEQ ID NO: 2). In one embodiment, the peptide or peptide derivative retains the same function as Ala-Ala-His-Met (SEQ ID NO: 3). In one embodiment, the peptide or peptide derivative retains the decreasing melanin pigmentation activity of Ala-Ala-His-Met (SEQ ID NO: 3).

The composition of the present invention comprises at least one peptide or peptide derivative. In one embodiment, the peptide or peptide derivative is the active agent. Importantly, the present composition promotes penetration of the peptide or peptide derivative, and at the same time keeps the peptide or peptide derivative in the solid state to provide chemical stability during the shelf life of the product.

Biological Activity of the Peptides

Bone morphogenetic proteins (BMPs) are a family of proteins involved in the development of the heart, nervous system and skeleton, in addition to the regulation of skin development and cutaneous biology, such as affecting hair and skin melanogenesis and hair follicle growth. BMP-6 has been reported to be involved in the control and regulation of melanin transfer and melanogenesis. BMP-6 binds to the Alk6 receptor, thereby stimulating the formation of filopodia and subsequent release of melanin granules (melanosomes) from the donor melanocyte to the recipient skin keratinocyte, which leads to pigmentation of the skin. Thus, inhibition of BMP-6 binding to Alk6 would lead to regulation of pigmentation, however, this could lead to undesired side effects, such as impact of interactions between the receptor and other BMPs. The inventors therefore aimed at producing very short peptides that would be capable of interacting with the receptor, and resulting in either an activation of the receptor, and thereby increasing the pigmentation, or prevention of interaction of BMP-6 and its receptor, which could lead to decreased pigmentation.

The inventors of the present invention subsequently produced four peptides derived from BMP-6 and tested their effect on pigmentation on human pigmented skin equivalents. As can be seen in Example 2, two of these peptides (SEQ ID NO: 2 and SEQ ID NO: 4) were able to increase pigmentation of the tested skin equivalents, as shown by photographic analysis. Furthermore, these two peptides could also be seen to increase the total melanin content in the skin samples (see Examples 3 and 4). These data suggest that these small peptides exhibit a good intra-epidermal delivery from a topical route, and that they show a promising use in the enhancement of skin pigmentation of human skin.

As can be seen from Example 4, treatment of peptide 3 (SEQ ID NO: 3) led to a reduction in melanin in the upper epidermal layers.

In one embodiment of the present invention, the composition exhibits the ability to modulate melanogenesis or melanin transfer. As used herein, the term "modulate" refers to increasing or decreasing for example melanogenesis or melanin transfer.

In one aspect, the present invention relates to a method of modulating pigmentation of skin and or hair, said method comprising administering a peptide or peptide derivative comprising the amino acid sequence of Xaa1-Ala-Xaa2-Met (SEQ ID NO: 13) wherein Xaa1 is Asn or Ala and Xaa2 is His or Ala, and wherein the peptide or peptide derivative comprises no more than 8 amino acid residues.

Method for Preparation of Peptides

The peptides according to the present invention may be prepared by any methods known in the art. Thus, the peptides as disclosed herein may be prepared by standard peptide-preparation techniques, such as solution synthesis or Merrifield-type solid phase synthesis.

In one embodiment, a peptide according to the invention is synthetically made or produced. The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999. In one embodiment, the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Construct, Delivery Vehicle and Host Cell

In one aspect, the present invention relates to a nucleic acid construct encoding the peptide as defined herein.

In another aspect, the present invention relates to a delivery vehicle comprising said nucleic acid construct. In one embodiment, the delivery vehicle is a delivery vector, such as a viral vector. In one embodiment of the present invention, the delivery vehicle is selected from the group consisting of: RNA based vehicles, DNA based vehicles, lipid based vehicles, polymer based vehicles, colloidal gold particles, virally derived DNA or RNA vehicles, adenoviruses, recombinant adeno-associated viruses (rAAV), retroviruses, lentiviruses, adeno-associated viruses, herpesviruses, vaccinia viruses, foamy viruses, cytomegaloviruses, Semliki forest virus, poxviruses, RNA virus vector and DNA virus vector.

In one aspect, the present invention relates to a host cell comprising said nucleic acid construct or delivery vehicle. In one embodiment, the host cell is a bacterial cell or mammalian cell, such as a human cell.

Composition

In one aspect, the present invention relates to a composition comprising said peptide, peptide derivate, nucleic acid construct, delivery vehicle or host cell. In one embodiment, the present invention relates to a composition comprising said peptide or peptide derivative.

In one embodiment, the composition is a pharmaceutical composition. In one embodiment, the composition is a cosmetic composition. In on embodiment, the composition is a topical formulation. In one embodiment, the composition is a medicament for topical delivery.

As used herein, the "particle composition" refers to the solid particle present in the formulation while "composition" refers to the composition of the intended product comprising peptide, peptide derivate, nucleic acid construct, delivery vehicle or host cell, particles and/or lipid vehicle.

In one embodiment, the composition comprises:

a) the peptide or peptide derivative as defined herein;

b) a saccharide or a modified saccharide; and c) a lipid.

In one embodiment, said composition comprises particles comprising, or consisting essentially of the peptide or peptide derivative and the saccharide or modified saccharide.

In one embodiment, said composition comprises 0.01 to 10 wt % particles, such as 0.1 to 5 wt % particles, such as 0.1 to 2 wt % particles.

In one embodiment, said particles have an average particle diameter of between 1 and 5 μm, such as between 5 and 10 μm, for example between 10 and 15 μm, such as between 15 and 20 μm, for example between 20 and 25 μm, such as between 25 and 30 μm, such as between 30 and 35 μm, for example between 35 and 40 μm, such as between 40 and 45 μm, for example between 45 and 50 μm.

In one embodiment, the particles have a diameter of less than 50 μm, for example less than 40 μm, such as less than 30 μm, for example less than 20 μm, such as less than 10 μm, such as less than 1 μm.

In one embodiment, the composition comprises at least 0.01 wt % peptide or peptide derivative, such as at least 0.1 wt %, such as at least 0.5 wt %, such as at least 1 wt %, such as at least 1.5 wt %, such as at least 2 wt %, such as at least 2.5 wt %, such as at least 3 wt %, such as at least 3.5 wt %, such as 4 wt %, such as 4.5 wt %, such as 5 wt %, such as 5.5 wt %, such as at least 6 wt %, such as at least 6.5 wt %, such as at least 7 wt %, such as at least 7.5 wt %, such as at least 8 wt %, such as at least 8.5 wt %, such as at least 9 wt %, such as at least 9.5 wt %, such as at least 10 wt %.

In one embodiment, the composition comprises no more than 2 wt % peptide or peptide derivative, such as no more than 5 wt %, such as no more than 10 wt %, such as no more than 15 wt %, such as no more than 20 wt %.

In one embodiment, the composition comprises between 0.01 and 5 wt % peptide or peptide derivative, such as between 0.1 and 5 wt % peptide or peptide derivative, such as between 0.1 and 2 wt % peptide or peptide derivative, such as between 0.1 and 1 wt % peptide or peptide derivative, such as between 1 and 5 wt % peptide or peptide derivative, such as between 5 and 10 wt % peptide or peptide derivative, such as between 10 and 15 wt % peptide or peptide derivative, such as between 15 and 20 wt % peptide or peptide derivative. In one embodiment, the composition comprises between 0.01 and 5 wt % peptide or peptide derivative, such as between such as between 0.01 and 2 wt % peptide or peptide derivative, such as between 0.1 and 1 wt % peptide or peptide derivative, such as between 1 and 5 wt % peptide or peptide derivative, such as between 5 and 10 wt % peptide or peptide derivative, such as between 10 and 15 wt % peptide or peptide derivative, such as between 15 and 20 wt % peptide or peptide derivative.

In one embodiment, the composition comprises at least 40 wt % lipid, such as at least 50 wt % lipid, such as at least 55 wt % lipid, such as at least 60 wt % lipid, such as at least 65 wt % lipid, such as at least 70 wt % lipid, such as at least 75 wt % lipid, such as at least 80 wt % lipid, such as at least 85 wt % lipid, such as at least 90 wt % lipid, such as at least 95 wt % lipid.

In one embodiment, the composition comprises no more than 55 wt % lipid, such as no more than 60 wt % lipid, such as no more than 65 wt % lipid, such as no more than 70 wt % lipid, such as no more than 75 wt % lipid, such as no more than 80 wt % lipid, such as no more than 85 wt % lipid, such as no more than 90 wt % lipid, such as no more than 95 wt % lipid.

In one embodiment, the composition comprises between 40 and 99 wt % lipid, such as between 40 and 60 wt % lipid, such as between 50 and 60 wt % lipid, such as between 60 and 70 wt % lipid, such as between 70 and 80 wt % lipid, such as between 80 and 90 wt % lipid, such as between 90 and 99.95 wt % lipid, In one embodiment, the composition comprises at least 0.1 wt % saccharide, such as at least 0.5 wt % saccharide, such as at least 1 wt % saccharide, such as at least 1.5 wt % saccharide, such as at least 2 wt % saccharide, such as at least 2.5 wt % saccharide, such as at least 3 wt % saccharide, such as at least 3.5 wt % saccharide, such as 4 wt %, such as 4.5 wt %, such as 5 wt %, such as 5.5 wt %, such as at least 6 wt % saccharide, such as at least 6.5 wt % saccharide, such as at least 7 wt % saccharide, such as at least 7.5 wt % saccharide, such as at least 8 wt % saccharide, such as at least 8.5 wt % saccharide, such as at least 9 wt % saccharide, such as at least 9.5 wt % saccharide, such as at least 10 wt % saccharide.

In one embodiment, the composition comprises no more than 2 wt % saccharide, such as no more than 5 wt % saccharide, such as no more than 10 wt % saccharide, such as no more than 15 wt % saccharide, such as no more than 20 wt % saccharide.

In one embodiment, the composition comprises between 0.01 and 5 wt % saccharide or modified saccharide, such as between 0.01 and 2 wt % saccharide or modified saccharide, such as between 0.1 and 2 wt % saccharide or modified saccharide, such as between 1 and 5 wt % saccharide, such as between 5 and 10 wt % saccharide or modified saccharide, such as between 10 and 15 wt % saccharide or modified saccharide, such as between 15 and 20 wt % saccharide or modified saccharide. In one embodiment, the composition comprises between 0.01 and 0.1 and 1 wt % saccharide, such as between 1 and 5 wt % saccharide, such as between 5 and 10 wt % saccharide, such as between 10 and 15 wt % saccharide, such as between 15 and 20 wt % saccharide.

In one embodiment, the saccharide is sucrose and the lipid is isopropyl myristate. In one embodiment, the composition further comprises petrolatum. In one embodiment, the composition further comprises glyceryl behenate. In one embodiment, the composition further comprises a surfactant. In one embodiment, said surfactant is sorbitan laurate (also known as Sorbitan monolaurate or Span20, CAS no. 1338-39-2). In one embodiment, the composition comprises or consists essentially of the peptide; sucrose; glyceryl behenate; petrolatum; isopropyl myristate; and sorbitan laurate.

It is to be understood that the sum of the components of the total composition does not exceed 100 wt %.

In one embodiment, the composition comprises or consists essentially of about 0.01 to 1 wt % peptide or peptide derivative; 0.01 to 4 wt % saccharide or modified saccharide; 85 to 95 wt % lipid; and optionally 2 to 10 wt % surfactant.

In one aspect, the present invention relates to a composition comprising:

a. 0.01 to 2 wt % peptide or peptide derivative;
b. 0.01 to 4 wt % saccharide or modified saccharide;
c. 35 to 50 wt % petrolatum; and
d. 40 to 60 wt % isopropyl myristate, with the proviso that the sum of the components of the total composition does not exceed 100 wt %.

In one embodiment, the composition comprises or consists essentially of about:

a) 0.01 to 1 wt % peptide or peptide derivative;
b) 0.01 to 2 wt % saccharide or modified saccharide;
c) 35 to 50 wt % petrolatum; and
d) 40 to 60 wt % isopropyl myristate.

In one embodiment, the composition comprises or consists essentially of about:

a) 0.01 to 1 wt % peptide or peptide derivative;
b) 0.01 to 2 wt % saccharide or modified saccharide;
c) 1 to 6 wt % glyceryl behenate;
d) 35 to 45 wt % petrolatum;
e) 40 to 60 wt % isopropyl myristate; and
f) 2 to 10 wt % surfactant, such as sorbitan laurate.

In one embodiment, the composition comprises or consists essentially of about:

a) 0.01 to 1 wt % peptide or peptide derivative;
b) 0.01 to 2 wt % sucrose, mannitol or glucose;
c) 1 to 8 wt % glyceryl behenate or carnauba wax;
d) 35 to 45 wt % petrolatum;
e) 40 to 60 wt % isopropyl myristate; and
f) 2 to 10 wt % surfactant, such as sorbitan laurate.

In one embodiment, the composition comprises 40 to 60 wt % isopropylmyristate, 2 to 6 wt % Sorbitan laurate and 2 to 6 wt % glyceryl behenate In one embodiment, the composition comprises 50% isopropylmyristate, 0.2% Sorbitan laurate and 3% glyceryl behenate or 6% carnauba wax. In one embodiment, the lipid comprises isopropyl myristate, petrolatum and glyceryl behenate. In one embodiment, the composition comprises 50 wt % isopropylmyristate, 4 wt % Sorbitan laurate and 3 wt % glyceryl behenate. In one embodiment, the composition comprises 50% isopropylmyristate, 0.2% Sorbitan laurate and 6% carnauba wax.

In one embodiment, the composition comprises or consists essentially of about:

a. 0.01 to 1 wt % peptide or peptide derivative;
b. 0.01 to 2 wt % sucrose;
c. 1 to 6 wt % glyceryl behenate;
d. 35 to 45 wt % petrolatum;
e. 40 to 60 wt % isopropyl myristate; and
f. 2 to 10 wt % sorbitan laurate.

In one embodiment, the composition comprises or consists essentially of about:

a. 0.01 to 1 wt % peptide or peptide derivative;
b. 0.01 to 1 wt % sucrose;
c. 1 to 6 wt % glyceryl behenate;
d. 35 to 45 wt % petrolatum;
e. 40 to 60 wt % isopropyl myristate; and
f. 2 to 6 wt % sorbitan laurate.

In one embodiment, the composition comprises or consists essentially of about:

a. 0.2 wt % peptide;
b. 0.4 wt % sucrose;
c. 3 wt % glyceryl behenate;
d. 42.4 wt % petrolatum;
e. 50 wt % isopropyl myristate; and
f. 4 wt % sorbitan laurate.

In one embodiment, the sum of the amounts in percent of the components does not exceed 100%.

In one embodiment, the composition comprises or consists essentially of about:

a) 1 wt % peptide;
b) 2 wt % sucrose;
c) 95 wt % lipid; and optionally
d) 2 wt % Sorbitan laurate.

In one embodiment, the composition is essentially a water free composition.

In one embodiment, the composition is in the form of an ointment, a powder, a spray, a lotion, a gel, a foam, a cream or a make-up. In one embodiment, the composition is in the form of a powder.

Method of Manufacturing

The particles can be manufactured by standard techniques such as freeze drying, spray drying or freeze spraying, followed by operations to reduce particle size to submicron levels. Such reduction of size can be performed using standard grinding techniques such as ball milling. Other suitable techniques are emulsification and solvent evaporation and yet other techniques for generation of particles can use precipitation of the active agent/saccharide.

In one aspect, the present invention provides a method of manufacturing a composition as described herein, comprising the following steps:

a) mixing the peptide with a saccharide;
b) freeze drying the mixture of a);
c) mixing b) with a lipid and a surfactant;
d) grinding the mixture of c); and
e) optionally mixing the mixture of d) with a lipid and a thickener.

Freeze-drying of the peptide together with sucrose may be performed to increase the dissolution of the peptide particles and to increase the chemical stability of the peptide.

In one embodiment, the method of manufacturing the composition as described herein comprises the following steps:

a) mixing the peptide together with the saccharide, such as sucrose;
b) lyophilizing the mixture of a);
c) mixing the lipid, such as isopropyl myristate, with a surfactant, for example sorbitan laurate, to obtain a homogenous solution;
d) adding the peptide-saccharide mixture of b) to the lipid-surfactant mixture in c) to obtain a suspension;
e) grinding the mixture of d), for example by using a standardized bead, wet-milling method;
f) mixing a lipid, such as petrolatum, with a surfactant, such as sorbitan laurate, and a thickener, such as glyceryl behenate; and
g) mixing the mixture of e) with the mixture of f).

The Saccharide

The composition comprises at least one saccharide or modified saccharide. Saccharides are made up of n monosaccharide units linked to each other by a glycosidic bond, wherein n is an integer. In one embodiment, the saccharide is selected from mono-, di- and trisaccharides. For monosaccharides, n is 1, for disaccharides, n is 2, and for trisaccharides, n is 3. In one embodiment, the saccharide is essentially consisting of a mono-, di- or trisaccharide, such as the properties of the saccharide are essentially determined by the mono-, di- or trisaccharide moiety. In one embodiment, the saccharide is a saccharide derivative or a modified saccharide, such as a sugar alcohol. In one embodiment, the saccharide is a sugar.

The melting point of a substance is the temperature at which it changes state from solid to liquid. At the melting point the solid and liquid phase exist in equilibrium. In one embodiment, the saccharide has a melting temperature between 60 and 140° C. In one embodiment, the saccharide has a melting temperature between 60 and 65° ° C., such as between 65 and 70° C., for example between 70 and 75° C., such as between 75 and 80° C., for example between 80 and 85° C., for example between 85 and 90° C., such as between 90 and 95° C., for example between 95 and 100° C., such as between 100 and 105° C., for example between 105 and 110° C., such as between 110 and 115° C., for example between 115 and 120° C., such as between 120 and 125° C., for example between 125 and 130° C., such as between 130 and 135° C., for example between 135 and 140° C.

In one embodiment, the saccharide is sucrose. In one embodiment, the saccharide is maltose. In one embodiment, the saccharide is trehalose. In one embodiment, the saccharide is raffinose. In on embodiment, the saccharide is maltotriose. In one embodiment, the saccharide is stachyose. In one embodiment, the saccharide is glucose. In one embodiment, the saccharide is dextran. In one embodiment, the saccharide is a sugar alcohol, such as mannitol.

In one embodiment, the weight ratio of saccharide and peptide or peptide derivative of the composition is 1:9 to 9:1, such as 1:9 or 9:1. In one embodiment, the weight ratio of saccharide and peptide or peptide derivative of the composition is 5:1 to 1:5, such as 2:1 or 1:1.

In one embodiment, the composition comprises at least 0.1 wt % saccharide, such as at least 0.5 wt % saccharide, such as at least 1 wt % saccharide, such as at least 1.5 wt % saccharide, such as at least 2 wt % saccharide, such as at least 2.5 wt % saccharide, such as at least 3 wt % saccharide, such as at least 3.5 wt % saccharide, such as at least 6 wt % saccharide, such as at least 6.5 wt % saccharide, such as at least 7 wt % saccharide, such as at least 7.5 wt % saccharide, such as at least 8 wt % saccharide, such as at least 8.5 wt % saccharide, such as at least 9 wt % saccharide, such as at least 9.5 wt % saccharide, such as at least 10 wt % saccharide. In one embodiment, the composition comprises no more than 2 wt % saccharide, such as no more than 5 wt % saccharide, such as no more than 10 wt % saccharide, such as no more than 15 wt % saccharide, such as no more than 20 wt % saccharide. In one embodiment, the composition comprises between 0.01 and 5 wt % saccharide or modified saccharide, such as between 0.01 and 2 wt % saccharide or modified saccharide, such as between 0.1 and 2 wt, such as between 0.1 and 1 wt % saccharide or modified saccharide, such as between 1 and 5 wt % saccharide or modified saccharide, such as between 5 and 10 wt % saccharide or modified saccharide, such as between 10 and 15 wt % saccharide or modified saccharide, such as between 15 and 20 wt % saccharide or modified saccharide.

Particles

As described herein, hydrophilic particles containing the active agent, such as a peptide or peptide derivative, and a saccharide dispersed in a lipid based vehicle generate drug penetration into the skin or follicle and its surroundings. This way of presenting the active agent to the disease area is useful for the treatment of many skin disorders and diseases.

Freeze-drying of the peptide together with sucrose may be performed to increase the dissolution of the peptide particles and to increase the chemical stability of the peptide. In one embodiment, the peptide and the saccharide form particles, which are hydrophilic. The particles may be in a solid, glass or rubber state. The particles can be manufactured by standard techniques such as freeze drying, spray drying or freeze spraying, followed by operations to reduce particle size to submicron levels.

In one embodiment, at least 50% of the particles have an average particle diameter of between 0.1 and 10 μm, such as between 0.1 and 1 μm, such as between 1 and 5 μm, such as between 5 and 10 μm, for example between 10 and 15 μm, such as between 15 and 20 μm, for example between 20 and 25 μm, such as between 25 and 30 μm, such as between 30 and 35 μm, for example between 35 and 40 μm, such as between 40 and 45 μm, for example between 45 and 50 μm.

In one embodiment, at least 50% of the particles have an average particle diameter of between 0.1 and 50 μm, for example between 0.1 and 15 μm, such as between 0.1 and 10 μm, such as between 0.1 and 2 μm.

In one embodiment, the size of the particles is below 50 μm, for example below 40 μm, such as below 30 μm, for example below 20 μm, such as below 10 μm.

In one embodiment, the composition comprises 0.01 to 10 wt % particles, such as 0.1 to 5 wt % particles, such as 0.1 to 2 wt % particles.

In one embodiment, the particles dissolve rapidly once coming in contact with water. In one embodiment, the particles dissolve within a minute in water at 37° C.

The Lipid Vehicle

The composition of the present invention comprises at least one lipid. The lipid function as a vehicle in the composition, i.e. serving as a medium for conveying the active ingredient. In one embodiment, the lipid vehicle comprises one or more different lipids. In one embodiment, the composition comprises one type of lipid. In one embodiment, the composition comprises two types of lipids.

Non-limiting examples of suitable lipids are mono-, di- and tri-esters of fatty acids, C6 to C22, and alcohols such as propanol, butanol, propyleneglycol and glycerol, and mixtures of lipids such as white or yellow soft paraffin. In one embodiment, the lipid is isopropyl myristate, In one embodiment, the lipid is isopropyl palmitate. In one embodiment, the lipid is petrolatum. In one embodiment, the lipid is selected from the group consisting of petrolatum, isopropyl myristate and glyceryl behenate.

The term 'petrolatum' as used herein refers to a semi-solid mixture of hydrocarbons (CAS number 8009-03-8). Petrolatum is also known as 'Petroleum jelly', 'white petrolatum', and 'soft paraffin', or multi-hydrocarbon. Petrolatum is also sold as Vaselin®.

In one embodiment, the lipid is a vaseline or a paraffin, such as paraffin oil. Paraffin oil or liquid paraffin oil is obtained in the process of petroleum distillation. Thus, the petroleum may be paraffin oil.

In one embodiment, isopropyl myristate is mixed with petrolatum 1:1. In one embodiment, the composition comprises isopropyl myristate and petrolatum. In one embodiment, the composition comprises isopropyl myristate and petrolatum in the weight ratio of 2:1 to 1:2, such as 3:2 to 2:3, such as about 1:1.

In one embodiment, the composition comprises petrolatum, isopropyl myristate and glyceryl behenate.

In one embodiment, the lipid is dried. In one embodiment, the isopropyl myristate is dried.

In one embodiment, the lipid is used to facilitate the distribution to skin.

In one embodiment, the lipid is used to facilitate the distribution to hair follicles, i.e. a lipid vehicle that is compatible with the sebum content in the hair follicle and to increase the chemical stability of the peptide. Thus, in one embodiment, the lipid is capable of solubilizing sebum.

Upon distribution to hair follicles, the lipid vehicle is important as a carrier of the particles and to make contact with the content of the follicle. Examples of components of such vehicle are fluid (at room and body temperature) lipids that dissolve sebum. The amount of solid material in the suspension may vary depending on the dose required and on the size of the area to be covered. A person skilled in the art will be able to recommend what particle concentration to use case by case.

In one embodiment, the lipid has solubility characteristics similar to sebum. In practice, this means that a mixture of compounds having a Hildebrand solubility coefficient between 6.5 and 10 $(cal/cm^3)^{1/2}$ are suitable solvents for sebum.

In one embodiment, the composition comprises at least 50 wt % lipid, such as at least 55 wt % lipid, such as at least 60 wt % lipid, such as at least 65 wt % lipid, such as at least 70 wt % lipid, such as at least 75 wt % lipid, such as at least 80 wt % lipid, such as at least 85 wt % lipid, such as at least 90 wt % lipid, such as at least 95 wt % lipid. In one embodiment, the composition comprises no more than 55 wt % lipid, such as no more than 60 wt % lipid, such as no more than 65 wt % lipid, such as no more than 70 wt % lipid, such as no more than 75 wt % lipid, such as no more than 80 wt % lipid, such as no more than 85 wt % lipid, such as no more than 90 wt % lipid, such as no more than 95 wt % lipid. In one embodiment, the composition comprises between 40 and 99 wt % lipid, such as between 40 and 60 wt % lipid, such as between 50 and 60 wt % lipid, such as between 60 and 70 wt % lipid, such as between 70 and 80 wt % lipid, such as between 80 and 90 wt % lipid, such as between 90 and 99.95 wt % lipid.

Additional Excipients

In one embodiment, additional excipients are added to the composition.

In one embodiment, the composition further comprises a surfactant. The hydrophilic-lipophilic balance (HLB) of a surfactant is a measure of the degree to which it is hydrophilic or lipophilic. In one embodiment, the HLB of the surfactant is between 9 and 16.

In one embodiment, the surfactant, such as sorbitan laurate, is added in order to prevent sedimentation of the particles, i.e. to maintain a homogenous suspension of the particles.

In one embodiment, the surfactant is selected form the group consisting of Sorbitan laurate, Span 80 and Brij 72. In one embodiment, the surfactant is Sorbitan laurate. The terms sorbitan laurate and span 20 are used herein interchangeably.

In one embodiment, the concentration of Sorbitan laurate is 1%.

In another embodiment, the surfactant is sugar based. In one embodiment, the sugar based surfactant is selected from the group consisting of sucrose cocoate, sorbitan laurate and polysorbate. In one embodiment, the sugar based surfactant has an HLB value between 9 and 16.

In one embodiment, the particles described above are adjusted to have surface properties making formulation of homogenous suspension possible. The surface properties can be adjusted or optimized by the use of surfactants. In one embodiment, the surfactant is selected from the group of nonionized surfactants that has a HLB, hydrophilic/lipophilic balance of 9 to 16.

In one embodiment, the composition comprises glycerol and/or propylene glycol.

In one embodiment, the composition further comprises a thickener. In one embodiment, glyceryl behenate is added as a thickener to achieve an attractive texture. Other thickeners known in the art may be used. In one embodiment, the thickener is glyceryl behenate or carnauba wax.

In one embodiment, the composition further comprises one or more additional active pharmaceutical ingredients, such as one or more additional peptides as defined below.

In one embodiment, traditional pharmaceutical compounds that increase viscosity, preservatives and buffers are added to the composition in order to improve physical characteristics of the composition.

In one embodiment, the composition comprises one or more so called "penetration enhancers". The term "penetration enhancer" as used herein refers to excipients that can accelerate the passage of API through the stratum corneum, for example by altering the state of the lipids in the stratum corneum or by increasing the solubility of the drug in the stratum corneum. Examples of penetration enhancers include 1-dodecylazacycloheptan-2-one, dimethyl sulfoxide, isopropyl myristate, decyl oleate, oleyl alcohol, octyldodecanol, propylene glycol, triacetin, and cocoyl caprylocaprate.

In one embodiment, the composition further comprises one or more additional components that absorbs or reflects some of the sun's ultraviolet (UV) radiation and thus helps protect against sunburn. Thus, in one embodiment, the composition function as a sunscreen. Such components are well-known to the person of skill in the art. For example, active ingredients of sunscreens include, but are not limited to, organic chemical compounds that absorb ultraviolet light; inorganic particulates that reflect, scatter, and absorb UV light (such as titanium dioxide, zinc oxide, or a combination of both); and organic particulates that mostly absorb UV light like organic chemical compounds, but contain multiple chromophores that reflect and scatter a fraction of light like inorganic particulates. In one embodiment, the composition further comprises one or more compounds selected from the group consisting of p-Aminobenzoic acid, Padimate O, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, Titanium dioxide, Zinc oxide, 4-Methylbenzylidene camphor, Bisoctrizole, Bemotrizinol, Tris-Biphenyl Triazine, bisimidazylate, Drometrizole Trisiloxane, Benzophenone-9,Octyl triazone, Diethylamino Hydroxybenzoyl Hexyl Benzoate, Iscotrizinol, Polysilicone-15 and Isopentyl-4-methoxycinnamate. In one embodiment, the composition further comprises titanium dioxide or zinc oxide. Micronized and nano-scale titanium dioxide and zinc oxide provide strong protection against UVA and UVB ultraviolet radiation.

In one embodiment, the composition further comprises one or more skin coloring agents, such as dihydroxyacetone and/or erythrulose.

Additional Peptides

In one embodiment, the composition further comprises one or more additional peptides. For example, the additional peptide may comprise or consist of an amino acid sequence selected from the group consisting of SEQ ID NO: 6 to 196. In one embodiment, the peptide is VDTYDGDISVVYGLR (FOL-005, SEQ ID NO: 6).

In one embodiment, the additional peptide is derived from a naturally-occurring peptide such as an osteopontin protein (e.g. the peptide comprises an amino acid sequence corresponding to that of a modified, for example mutated, version of a naturally-occurring osteopontin protein). A characterising feature of the osteopontin-derived peptide in the compositions of the invention is that the RGD domain naturally present in osteopontin is inactivated such that it is non-functional (at least in part). For example, inactivation of the RGD domain may prevent the osteopontin-derived peptide from binding to one or more of the integrins which bind the naturally occurring osteopontin protein.

Thus, by "modified osteopontin peptide" we include peptides corresponding to a modified form of a naturally-occurring osteopontin protein in which the RGD domain is non-functional (at least in part), as well as fragments and variants thereof which retain a hair-stimulatory property of the 'full length' modified osteopontin.

In one embodiment, the additional peptide comprises or consists of a fragment of the amino acid sequence of SEQ ID NO: 6 (FOL-005), or a variant thereof.

The term "fragment" as used herein may include any fragment, preferably a biologically active fragment of an amino acid sequence described herein. In one embodiment, the fragment is of at least 6 contiguous amino acids of the amino acid sequence of SEQ ID NO: 6, for example at least 7, 8, 9, 10, 11, 12, 13, 14, 15, 16, 17, 18, 19, 20, 30, 40, 50, 100, 150, 200, 210, 220, 230, 240, 250, 255, 260, 265, 270, 275, 280, 285, 286, 287, 288, 289 290, 291 or 292 contiguous amino acids of SEQ ID NO: 6.

By "variant" we mean that the peptide does not share 100% amino acid sequence identity with SEQ ID NO: 6, i.e. one or more amino acids of SEQ ID NO: 6 must be mutated. For example, the peptide may comprise or consist of an amino acid sequence with at least 50% identity to the amino acid sequence of SEQ ID NO: 6, more preferably at least 60%, 70% or 80% or 85% or 90% identity to said sequence, and most preferably at least 95%, 96%, 97%, 98% or 99% identity to said amino acid sequence.

The variant peptide may also comprise one or more additional amino acids, inserted at the N- and/or C-terminus and/or internally within the amino acid sequence of SEQ ID NO: 6. For example, the peptide may comprise or consist of at least 2, 3, 4, 5, 6, 7, 8, 9, 10, 15 or 20 additional amino acids at the N- and/or C-terminus and/or internally.

In one embodiment, the additional peptide shares amino acid sequence similarity with a sub-region of naturally occurring tenascin proteins. In some embodiments, said additional peptide may be regarded as an active fragment of a naturally-occurring tenascin protein or a variant of such as a fragment.

In one embodiment, the additional peptide comprises or consists of:

i) an amino acid sequence of the general formula:

(SEQ ID NO: 14)

$KX_2LAX_5X_6X_7X_8IX_{10}LX_{12}YGIK$ wherein:
$X_2$ is C, P or G;
$X_5$ is E or G;
$X_6$ is C, D or I;
$X_7$ is D, I, S or G;
$X_8$ is S, D or G;
$X_{10}$ is E or G;
$X_{12}$ is S or T;

with the proviso that if $X_{12}$ is T, the peptide comprises no more than 25 amino acid residues; and with the proviso that if $X_2$ is P, $X_5$ is E, $X_6$ is I, $X_7$ is D, $X_8$ is S, $X_{10}$ is E and $X_{12}$ is S, the peptide comprises no more than 85 amino acid residues;

ii) an amino acid sequence of the general formula:

(SEQ ID NO: 15)

$X_{10}LX_{12}YGIK$ wherein:
$X_{10}$ is E or G;
$X_{12}$ is S or T;

with the proviso that if $X_{12}$ is T, the peptide comprises no more than 25 amino acids; and with the proviso that if $X_{10}$ is E and $X_{12}$ is S, the peptide comprises no more than 85 amino acid residues;

iii) an amino acid sequence of the general formula:

(SEQ ID NO: 16)

$VDVPZ_5GDISLAYZ_{13}LR$ wherein:
$Z_5$ is E or N;
$Z_{13}$ is R or G;

iv) an amino acid sequence of the general formula:

(SEQ ID NO: 17)

$VDTYDGZ_7Z_8SVVYGLR$ wherein:
$Z_7$ is D or G;
$Z_8$ is I or G;

v) an amino acid sequence of the general formula:

(SEQ ID NO: 18)

$GDPNZ_5Z_6Z_7Z_8Z_9SVVYGLR$ wherein:
$Z_5$ is D or G;
$Z_6$ is D or G
$Z_7$ is I or R;
$Z_8$ is G or absent;
$Z_9$ is D or absent;

vi) an amino acid sequence of the general formula:

(SEQ ID NO: 19)

$KX_2LAX_5X_6X_7X_8IX_{10}LSYGIK$ wherein:
$X_2$ is C, P or G;
$X_5$ is E or G;
Xe is C, I or absent;
$X_7$ is D, G or absent;
$X_8$ is S, G or absent;
$X_{10}$ is E or G;

vii) an amino acid sequence of the general formula:

(SEQ ID NO: 20)

$KX_2LAX_{51}X_{10}LSYGIK$ wherein:
$X_2$ is C, P or G;
$X_5$ is E or G;
$X_{10}$ is E or G;

viii) an amino acid sequence of the general formula:

(SEQ ID NO: 21)
$Z_7Z_8SZ_{10}Z_{11}YGLR$ wherein:
$Z_7$ is D or G;
$Z_8$ is I or G;
$Z_{10}$ is V or L;
$Z_{11}$ is V or A;

ix) an amino acid sequence of the general formula:

(SEQ ID NO: 22)
$VDZ_3Z_4Z_5GZ_6Z_7Z_8SZ_{10}Z_{11}YGLR$ wherein:
$Z_3$ is T or V;
$Z_4$ is Y or P;
$Z_5$ is D or N;
$Z_7$ is D or G;
$Z_8$ is I or G;
$Z_{10}$ is V or L;
$Z_{11}$ is V or A.

The term 'absent' as used herein, e.g. "$X_6$ is C, I or absent" is to be understood as that the amino acid residues directly adjacent to the absent amino acid are directly linked to each other by a conventional amide bond.

In one embodiment, the additional peptide comprises or consists of an amino acid sequence selected from the group consisting of GDPNDGRGDSVVYGLR (SEQ ID NO: 23), VDTYDGGISVVYGLR (SEQ ID NO: 24), and VDTYDGDGSVVYGLR (SEQ ID NO: 25), VDVPEGDISLAYGLR (SEQ ID NO: 26), LDGLVRAYDNISPVG (SEQ ID NO: 27), GDPNGDISVVYGLR (SEQ ID NO: 28), VDVPNGDISLAYRLR (SEQ ID NO: 29), and VDVPEGDISLAYRLR (SEQ ID NO: 30).

In one embodiment, the additional peptide comprises or consists of an amino acid sequence selected from the group consisting of GDPNDGRGDSVVYGLR (SEQ ID NO: 23), VDTYDGGISVVYGLR (SEQ ID NO: 24), and VDTYDGDGSVVYGLR (SEQ ID NO: 25), VDVPEGDISLAYGLR (SEQ ID NO: 26), LDGLVRAYDNISPVG (SEQ ID NO: 27), GDPNGDISVVYGLR (SEQ ID NO: 28), VDVPNGDISLAYRLR (SEQ ID NO: 29), VDVPEGDISLAYRLR (SEQ ID NO: 30), V(beta-D)TYDGDISVVYGLR (SEQ ID NO: 31), VDTY(beta-D)GDISVVYGLR (SEQ ID NO: 32), and VDTYDG(beta-D)ISVVYGLR (SEQ ID NO:33).

In one embodiment, the additional peptide comprise or consists of the amino acid sequence of VDTYDGDISVVYGLR (SEQ ID NO: 6; FOL-005) or a fragment/variant thereof.

In one embodiment, the additional peptide comprises or consists of the amino acid sequence of KPLAEIDSIELSYGIK (SEQ ID NO: 10, FOL-014) or a fragment/variant thereof.

In one embodiment, the additional peptide comprises or consists of the amino acid sequence of VDVPNGDISLAYGLR (SEQ ID NO: 9, FOL-004) or a fragment/variant thereof.

In one embodiment, the additional peptide comprises or consists of an amino acid sequence selected from the group consisting of KCLAECDSIELSYGIK (SEQ ID NO: 34), CLAEIDSC (SEQ ID NO: 35), CFKPLAEIDSIECSYGIK (SEQ ID NO: 36), KPLAEDISIELSYGIK (SEQ ID NO: 37), KPLAEIGDIELSYGIK (SEQ ID NO: 38), KPLAEGDIELSYGIK (SEQ ID NO: 39), KPLAEIELSYGIK (SEQ ID NO: 40), KPLAEIDSIELTYGIK (SEQ ID NO: 41), KPLAEIDGIELSYGIK (SEQ ID NO: 42), KPLAEIDGIELTYGIK (SEQ ID NO: 43), KPLAEIGSIELSYGIK (SEQ ID NO: 44), KGLAEIDSIELSYGIK (SEQ ID NO: 45), KPLAGIDSIGLSYGIK (SEQ ID NO: 46), KCLAEIDSCELSYGIK (SEQ ID NO: 47) and CFKPLAEIDSIEC (SEQ ID NO: 48), or a variant or fragment thereof.

In one embodiment, the additional peptide comprises or consists of an amino acid sequence selected from the group consisting of LAEIDSIELSYGIK (SEQ ID NO: 49), AEIDSIELSYGIK (SEQ ID NO: 50), EIDSIELSYGIK (SEQ ID NO: 51), IDSIELSYGIK (SEQ ID NO: 52), DSIELSYGIK (SEQ ID NO: 53), SIELSYGIK (SEQ ID NO: 54), IELSYGIK (SEQ ID NO: 55), or a variant or fragment thereof.

In one embodiment, the additional peptide comprises or consists of an amino acid sequence selected from the group consisting of KPLAEIDSIELSYGI (SEQ ID NO: 56), KPLAEIDSIELSYG (SEQ ID NO: 57), KPLAEIDSIELSY (SEQ ID NO: 58), KPLAEIDSIELS (SEQ ID NO: 59), KPLAEIDSIEL (SEQ ID NO: 60), KPLAEIDSIE (SEQ ID NO: 61), or a variant of fragment thereof.

In another embodiment, the additional peptide is selected from the group consisting of SEQ ID NO: 6, 10, 62, 63, 6, 65, 66, 67, 68, 69, 70, 71, 72, 73, 74, 75, 76, 77, 178, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 9, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 24, 25, 34, 35, 36, 193, 37, 38, 39, 40, 41, 42, 43, 44, 45, 46, 47, 48, 26, 27, 28, 29, 30, 31, 32, 33, 49, 50, 51, 52, 53, 54, 55, 194, 195, 56, 57, 58, 59, 60, 61, 196, 8, and 12.

In one embodiment, the additional peptide is conjugated to a moiety, such as a moiety selected from the group consisting of polyethylene glycol (PEG), monosaccharides, fluorophores, chromophores, radioactive compounds, and cell-penetrating peptides. In one embodiment, the additional peptide consists of an amino acid sequence selected from the group consisting of SEQ ID NO: 6, 8 to 12 and 14 to 196, and said peptide is modified by being glycosylated or by PEGylation, amidation, esterification, acylation, acetylation and/or alkylation. In one embodiment, the peptide consists of an amino acid sequence selected from the group consisting of SEQ ID NO: 6, 8 to 12 and 14 to 196, and said peptide is fused to another polypeptide, such as a polypeptide selected from the group consisting of glutathione-S-transferase (GST) and protein A, or to a tag.

Area of Delivery

The present invention relates to a composition suitable for topical delivery of one or more active agents, such as one or more peptides. In one embodiment, the topical application site is on a skin surface of the patient. In one embodiment, the topical application site is on a tissue surface of a patient.

In one embodiment, the composition is suitable for delivery of one or more peptide or peptide derivative as defined herein into follicles. The follicular administration route presents an improvement over invasive administration forms. When a drug is injected by subcutaneous or intradermal routes, the drug concentration at administration site decreases instantly, and within a few hours the local drug concentration is not sufficient for generation of a biological effect. When treatment of local sites of the disease is desired, parenteral administration is undesirable. Generally, a constant drug concentration during the treatment period is more favourable. Follicular delivery is one non-invasive way of overcoming this problem. In addition, follicular delivery allows for a depo effect as the drug load can be maximized.

Use of the Composition

In one aspect, the present invention provides a method for topical delivery of the peptide or peptide derivative to a subject in need thereof, comprising applying an effective amount of a composition as described herein comprising said peptide or peptide derivative to a topical application site of the subject.

In one embodiment, the composition may be applied for several days, for example for several weeks, such as several months. In one embodiment, the composition is for long-term use.

The present invention is not limited to medical uses but the composition as described herein may also be used as cosmetic agents (in the sense that it does not provide any physical health improvement, as such, but merely provide an aesthetic benefit to the mammal).

In one embodiment, the peptide, peptide derivative or composition as defined herein is for use in self tanning. The term "self tanning", or "sunless tanning", as used herein refers to increase in skin pigmentation without UV exposure.

It will be further appreciated by skilled persons that the compositions of the invention may be used in vivo, ex vivo or in vitro.

In one embodiment, the composition is applied to a subject or a patient. In one embodiment, the subject or patient is a mammal. In one embodiment, the mammal is a human.

In one embodiment, the use is non-therapeutic.

Medical Use

In one aspect, the present invention is related to the peptide, peptide derivative or composition as described herein for use as a medicament. In one embodiment, the peptide of the pharmaceutical composition is the active ingredient, such as the active pharmaceutical ingredient. Thus, in one embodiment, the pharmaceutical composition is suitable for use in the treatment of the indications, which the peptide or peptide derivative is effective against.

In one embodiment, the peptide, peptide derivative or composition as described herein is for use in the treatment of dermatological conditions. In one embodiment, the dermatological condition is a hypo-pigmentary condition.

In one embodiment, the invention provides compositions for use in treating a medical condition associated with abnormal pigmentation of the skin. Such treatment may be curative, or it might be used in order to lessen symptoms. Diseases or medical conditions associated with altered pigmentation of the skin which could be treated include hyperpigmentation (e.g., melasma, chloasma, senile lentigo, solar lentigo, ephelides, post-inflammatory hyperpigmentation) and hypopigmentation (e.g. vitiligo, and post-inflammatory hypopigmentation) and pigmentation loss as a result of skin damage.

Thus, in one embodiment, the peptide, peptide derivative or composition as described herein is for use in the treatment of disorders of the skin and subcutaneous tissue. In one embodiment, the disorder of the skin and subcutaneous tissue is selected from the group consisting of postinflammatory hyperpigmentation, chloasma, freckles, café au lait spots, and melanin hyperpigmentation, such as lentigo. Hypopigmentation may for example be seen in albinism, idiopathic guttate hypomelanosis, leprosy, leucism, phenylketonuria, *pityriasis* alba, vitiligo, Angelman syndrome, *tinea versicolor*, and yaws.

In one aspect, the present invention relates to a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues, for use in the treatment a disease or disorder associated with hypopigmentation, such as selected from the group consisting of vitiligo, albinism, idiopathic guttate hypomelanosis, leprosy, leucism, phenylketonuria, *pityriasis* alba, Angelman syndrome, *tinea versicolor*, and yaws.

In one aspect, the present invention relates to a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues, for use in the treatment of hypopigmentation of the skin or for use in the treatment of vitiligo.

In one aspect, the present invention relates to use of the peptide, peptide derivative or composition as described herein in the manufacture of a medicament for treatment or prevention of a disease or condition associated with depigmentation and/or hypopigmentation.

In one aspect, the present invention relates to use of the composition as described herein in the manufacture of a medicament for treatment or prevention of a disease or condition associated with hyperpigmentation.

In one aspect, the present invention relates to a peptide or peptide derivative comprising the amino acid sequence of Ala-Ala-His-Met (SEQ ID NO: 3), wherein the peptide or peptide derivative comprises no more than 8 amino acid residues, for use in the treatment of hypopigmentation of the skin or for use in the treatment of a disease or condition associated with such hyperpigmentation, as postinflammatory hyperpigmentation, chloasma, f freckles, café au lait spots, and melanin hyperpigmentation, such as lentigo.

In one embodiment, an effective amount of the peptide, peptide derivative or composition is administered to the subject. As used herein, the term 'effective' means adequate to accomplish a desired, expected, or intended result. For instance, an 'effective amount' or a 'cosmetically effective amount' or a 'therapeutically effective amount' means an amount that is adequate to accomplish a desired, expected or intended result. This is a predetermined quantity of active material calculated to produce the desired therapeutic effect. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

As used herein, a 'therapeutically effective amount', or 'effective amount', or 'therapeutically effective', refers to that amount of active ingredient, which ameliorates the symptoms or condition. For example, in one embodiment, a 'therapeutically effective amount' refers to that amount which has the ability to modulate skin pigmentation.

Skin Pigmentation

In one aspect, the present invention provides the use of the peptide, peptide derivative or composition for stimulating melanin pigmentation of the skin and/or hair in a subject, such as a mammal. In one embodiment, the peptide, peptide derivative or composition is for use in stimulating melanin pigmentation of the skin in a mammal.

In one aspect, the present invention relates to use of a peptide or peptide derivative comprising the amino acid sequence of Asn-Ala-Xaa2-Met (SEQ ID NO: 1), wherein Xaa2 is His or Ala, and wherein the peptide or peptide derivative comprises no more than 8 amino acid residues, for non-therapeutic increase of melanin pigmentation of skin and/or hair of a subject. In one embodiment, said peptide or peptide derivative comprises or consists of an amino acid sequence Asn-Ala-Ala-Met (SEQ ID NO: 4). In one embodiment, said peptide or peptide derivative comprises or consists of an amino acid sequence Asn-Ala-His-Met (SEQ ID NO: 2)

In one aspect, the present invention provides the use of the peptide, peptide derivative or composition for decreasing melanin pigmentation of the skin and/or hair in a subject, such as a mammal.

In one embodiment, the peptide, peptide derivative or composition is for use in preventing or decreasing melanin pigmentation of the skin in a mammal.

In one aspect, the present invention relates to use of a peptide or peptide derivative comprises or consists of the amino acid sequence of Ala-Ala-His-Met (SEQ ID NO: 3), wherein the peptide or peptide derivative comprises no more than 8 amino acid residues, for non-therapeutic decrease of melanin pigmentation of skin and/or hair of a subject. In one aspect, the present invention provides a method of modulating melanin pigmentation of the skin and/or hair, said method comprising administering to a subject in need thereof, an effective amount of the peptide, peptide derivative or composition.

In one aspect, the present invention provides a method of treatment or prevention of a disease or condition associated with depigmentation and/or hypopigmentation, said method comprising administering to a subject in need thereof, an effective amount of the peptide, peptide derivative or composition.

In one aspect, the present invention provides a method of treatment of prevention of a disease or condition associated with hyperpigmentation, said method comprising administering to a subject in need thereof, an effective amount of the peptide, peptide derivative or composition.

In one embodiment, the administration is topical.

In one embodiment, the subject is a mammal. In one embodiment, the mammal is a human.

Cosmetic Use

In one aspect, the peptide, peptide derivative or composition as described herein is for cosmetic use.

In one aspect, the present invention relates to a cosmetic method of darkening of skin and/or hair color, the method comprising administering to a subject a peptide, peptide derivative or composition as defined herein. In one embodiment, said peptide or peptide derivative comprises or consists of an amino acid sequence Asn-Ala-Ala-Met (SEQ ID NO: 4). In one embodiment, said peptide or peptide derivative comprises or consists of an amino acid sequence Asn-Ala-His-Met (SEQ ID NO: 2). In one embodiment, the darkening of skin and/or hair color is through increasing the level of melanin pigmentation of the hair and/or the skin.

In one aspect, the present invention relates to a cosmetic method of lightening of skin and/or hair color, the method comprising administering to a subject a peptide, peptide derivative or composition as defined herein. In one embodiment, said peptide or peptide derivative comprises or consists of an amino acid sequence of Ala-Ala-His-Met (SEQ ID NO: 3). In one embodiment, the lightening of skin and/or hair color is through reducing the level of melanin pigmentation of the skin and/or hair.

Combination Treatment

It will be appreciated by persons skilled in the art that the compositions of the invention may be used on their own or in combination with other therapeutic or cosmetic agents. For example, the compositions of the invention may be used in a combination therapy with existing treatments to prevent and/or treat hypopigmentation or hyperpigmentation.

In one embodiment, the composition comprises one or more additional components that absorbs or reflects some of the sun's ultraviolet (UV) radiation and thus helps protect against sunburn. Thus, in one embodiment, the composition is a combined product functioning as a sunscreen while decreasing skin pigmentation, i.e. bleaching the skin. In another one embodiment, the composition is a combined product functioning as a sunscreen while increasing skin pigmentation, i.e. darkening the skin.

In one embodiment, the composition comprises one or more additional peptides as defined herein. In one embodiment, the additional peptide stimulates hair growth. Thus, in one embodiment, the composition is a combined product, which both increases the pigmentation of the hair and stimulates hair growth.

Items

1. A peptide or peptide derivative comprising the amino acid sequence of Ala-Xaa2-Met, wherein Xaa2 is His or Ala.
2. The peptide or peptide derivative according to item 1, wherein the peptide or peptide derivative comprises the amino acid sequence of Xaa1-Ala-Xaa2-Met (SEQ ID NO: 13), wherein Xaa1 is Asn or Ala, and Xaa2 is His or Ala.
3. The peptide or peptide derivative according to any one of the preceding items, wherein the peptide or peptide derivative comprises the amino acid sequence of Asn-Ala-Xaa2-Met (SEQ ID NO: 1), wherein Xaa2 is His or Ala.
4. The peptide or peptide derivative according to any one of the preceding items, wherein the peptide comprises or consists of an amino acid sequence Asn-Ala-His-Met (SEQ ID NO: 2).
5. The peptide or peptide derivative according to any one of the preceding items, wherein the peptide comprises or consists of an amino acid sequence Ala-Ala-His-Met (SEQ ID NO: 3).
6. The peptide or peptide derivative according to any one of the preceding items, wherein the peptide comprises or consists of an amino acid sequence Asn-Ala-Ala-Met (SEQ ID NO: 4).
7. The peptide or peptide derivative according to any one of the preceding items, wherein the peptide comprises no more than 20 amino acid residues, such as no more than 15 amino acid residues, such as no more than 14 amino acid residues, such as no more than 13 amino acid residues, such as no more than 12 amino acid residues, such as no more than 11 amino acid residues, such as no more than 10 amino acid residues, such as no more than 9 amino acid residues, such as no more than 8 amino acid residues, such as no more than 7 amino acid residues, such as no more than 6 amino acid residues, such as no more than 5 amino acid residues, such as no more than 4 amino acid residues, such as no more than 3 amino acid residues.

8. The peptide or peptide derivative according to any one of the preceding items, wherein the peptide comprises at least 4 amino acid residues, such as at least 5 amino acid residues, such as at least 6 amino acid residues, such as at least 7 amino acid residues, such as at least 8 amino acid residues, such as at least 9 amino acid residues, such as at least 10 amino acid residues, such as at least 11 amino acid residues, such as at least 12 amino acid residues, such as at least 15 amino acid residues.
9. The peptide or peptide derivative according to any one of the preceding items, wherein the peptide is cyclic.
10. The peptide or peptide derivative according to any one of the preceding items, wherein the peptide is glycosylated.
11. The peptide or peptide derivative according to any one of the preceding items, wherein the peptide derivative is a peptide which is conjugated to a moiety, such as a moiety selected from the group consisting of polyethylene glycol (PEG), monosaccharides, fluorophores, chromophores, radioactive compounds, and cell-penetrating peptides.
12. The peptide or peptide derivative according to any one of the preceding items, wherein the peptide or peptide derivative is modified by being glycosylated or by PEGylation, amidation, esterification, acylation, acetylation and/or alkylation.
13. The peptide or peptide derivative according to any one of the preceding items, wherein the peptide or peptide derivative is a peptide which is fused to another polypeptide, such as a polypeptide selected from the group consisting of glutathione-S-transferase (GST) and protein A, or to a tag.
14. A nucleic acid construct encoding a peptide according to any one of the preceding items.
15. A delivery vehicle comprising the nucleic acid construct according to any one of the preceding items.
16. The delivery vehicle according to any one of the preceding items, wherein said vehicle is selected from the group consisting of: RNA based vehicles, DNA based vehicles, lipid based vehicles, polymer based vehicles, colloidal gold particles, virally derived DNA or RNA vehicles, adenoviruses, recombinant adeno-associated viruses (rAAV), retroviruses, lentiviruses, adeno-associated viruses, herpesviruses, vaccinia viruses, foamy viruses, cytomegaloviruses, Semliki forest virus, poxviruses, RNA virus vector and DNA virus vector.
17. A host cell comprising the polynucleotide or the vector according to any one of the preceding items.
18. The host cell according to any one of the preceding items, wherein the host cell is a bacterial cell or a mammalian cell, such as a human cell.
19. A composition comprising the peptide, the peptide derivative, the nucleic acid construct, the delivery vehicle or the host cell according to any one of the preceding items.
20. A composition comprising the peptide or peptide derivative according to any one of the preceding items.
21. The composition according to any one of the preceding items, wherein the composition comprises:
    a) the peptide or peptide derivative according to any one of the preceding items;
    b) a saccharide or a modified saccharide; and
    c) a lipid.
22. The composition according to any one of the preceding items, wherein composition comprises particles comprising, or consisting essentially of the peptide or peptide derivative and the saccharide or modified saccharide.
23. The composition according to any one of the preceding items, wherein the composition comprises 0.01 to 10 wt % particles, such as 0.1 to 5 wt % particles, such as 0.1 to 2 wt % particles.
24. The composition according to any one of the preceding items, wherein at least 50% of the particles have an average particle diameter of between 1 and 5 μm, such as between 5 and 10 μm, for example between 10 and 15 μm, such as between 15 and 20 μm, for example between 20 and 25 μm, such as between 25 and 30 μm, such as between 30 and 35 μm, for example between 35 and 40 μm, such as between 40 and 45 μm, for example between 45 and 50 μm.
25. The composition according to any one of the preceding items, wherein at least 50% of the particles have a diameter of less than 50 μm, for example less than 40 μm, such as less than 30 μm, for example less than 20 μm, such as less than 10 μm, such as less than 1 μm.
26. The composition according to any one of the preceding items, wherein at least 50% of the particles have an average particle diameter of between 0.1 and 50 μm, for example between 0.1 and 15 μm, such as between 0.1 and 10 μm, such as between 0.1 and 2 μm.
27. The composition according to any one of the preceding items, wherein the composition comprises at least 0.01 wt % peptide or peptide derivative, such as at least 0.5 wt %, such as at least 0.1 wt %, 1 wt %, such as at least 1.5 wt %, such as at least 2 wt %, such as at least 2.5 wt %, such as at least 3 wt %, such as at least 3.5 wt %, such as at least 6 wt %, such as at least 6.5 wt %, such as at least 7 wt %, such as at least 7.5 wt %, such as at least 8 wt %, such as at least 8.5 wt %, such as at least 9 wt %, such as at least 9.5 wt %, such as at least 10 wt % peptide or peptide derivative.
28. The composition according to any one of the preceding items, wherein the composition comprises no more than 2 wt % peptide or peptide derivative, such as no more than 5 wt %, such as no more than 10 wt %, such as no more than 15 wt %, such as no more than 20 wt % peptide or peptide derivative.
29. The composition according to any one of the preceding items, wherein the composition comprises between 0.01 and 5 wt % peptide or peptide derivative, such as between 0.01 and 2 wt %, such as between 0.1 and 1 wt %, such as between 1 and 5 wt %, such as between 5 and 10 wt %, such as between 10 and 15 wt %, such as between 15 and 20 wt % peptide or peptide derivative.
30. The composition according to any one of the preceding items, wherein the saccharide is a sugar.
31. The composition according to any one of the preceding items, wherein the saccharide has a melting temperature between 60 and 140° C.
32. The composition according to any one of the preceding items, wherein the saccharide has a melting temperature between 60 and 65° C. such as between 65 and 70, for example between 70 and 75, such as between 75 and 80, for example between 80 and 85, for example between 85 and 90, such as between 90 and 95, for example between 95 and 100, such as between 100 and 105, for example between 105 and 110, such as between 110 and 115, for example between 115 and 120, such as between 120 and 125, for example between 125 and 130, such as between 130 and 135, for example between 135 and 140° C.

33. The composition according to any one of the preceding items, wherein the saccharide is sucrose.
34. The composition according to any one of the preceding items, wherein the saccharide is mannitol.
35. The composition according to any one of the preceding items, wherein the saccharide is glucose.
36. The composition according to any one of the preceding items, wherein the saccharide is selected form the group consisting of maltose, trehalose, raffinose, maltotriose, stachyose, dextran, glucose, mannitol and sucrose.
37. The composition according to any one of the preceding items, wherein the composition comprises at least 0.1 wt % saccharide, such as at least 0.5 wt % saccharide, such as at least 1 wt % saccharide, such as at least 1.5 wt % saccharide, such as at least 2 wt % saccharide, such as at least 2.5 wt % saccharide, such as at least 3 wt % saccharide, such as at least 3.5 wt % saccharide, such as at least 6 wt % saccharide, such as at least 6.5 wt % saccharide, such as at least 7 wt % saccharide, such as at least 7.5 wt % saccharide, such as at least 8 wt % saccharide, such as at least 8.5 wt % saccharide, such as at least 9 wt % saccharide, such as at least 9.5 wt % saccharide, such as at least 10 wt % saccharide.
38. The composition according to any one of the preceding items, wherein the composition comprises no more than 2 wt % saccharide, such as no more than 5 wt % saccharide, such as no more than 10 wt % saccharide, such as no more than 15 wt % saccharide, such as no more than 20 wt % saccharide.
39. The composition according to any one of the preceding items, wherein the composition comprises between 0.01 and 5 wt % saccharide or modified saccharide, such as between 0.01 and 2 wt % saccharide or modified saccharide, such as between 0.1 and 2 wt, such as between 0.1 and 1 wt % saccharide or modified saccharide, such as between 1 and 5 wt % saccharide or modified saccharide, such as between 5 and 10 wt % saccharide or modified saccharide, such as between 10 and 15 wt % saccharide or modified saccharide, such as between 15 and 20 wt % saccharide or modified saccharide.
40. The composition according to any one of the preceding items, wherein the lipid compounds have a Hildebrand solubility coefficient between 6.5 and 10 $(cal/cm^3)^{1/2}$.
41. The composition according to any one of the preceding items, wherein the lipid is isopropyl myristate.
42. The composition according to any one of the preceding items, wherein the lipid petrolatum, and/or isopropyl myristate.
43. The composition according to any one of the preceding items, wherein the composition comprises glycerol or propylene glycol.
44. The composition according to any one of the preceding items, wherein the lipid solubilizes sebum.
45. The composition according to any one of the preceding items, wherein the composition comprises at least 50 wt % lipid, such as at least 55 wt % lipid, such as at least 60 wt % lipid, such as at least 65 wt % lipid, such as at least 70 wt % lipid, such as at least 75 wt % lipid, such as at least 80 wt % lipid, such as at least 85 wt % lipid, such as at least 90 wt % lipid, such as at least 95 wt % lipid.
46. The composition according to any one of the preceding items, wherein the composition comprises no more than 55 wt % lipid, such as no more than 60 wt % lipid, such as no more than 65 wt % lipid, such as no more than 70 wt % lipid, such as no more than 75 wt % lipid, such as no more than 80 wt % lipid, such as no more than 85 wt % lipid, such as no more than 90 wt % lipid, such as no more than 95 wt % lipid.
47. The composition according to any one of the preceding items, wherein the composition comprises between 40 and 99 wt % lipid, such as between 40 and 60 wt % lipid, such as between 50 and 60 wt % lipid, such as between 60 and 70 wt % lipid, such as between 70 and 80 wt % lipid, such as between 80 and 90 wt % lipid, such as between 90 and 99.95 wt % lipid.
48. The composition according to any one of the preceding items, wherein the composition further comprises a thickener.
49. The composition according to any one of the preceding items, wherein the thickener is glyceryl behenate or carnauba wax.
50. The composition according to any one of the preceding items, wherein the composition further comprises a surfactant.
51. The composition according to any one of the preceding items, wherein the surfactant is sorbitan laurate.
52. The composition according to any one of the preceding items, wherein the surfactant is selected form the group consisting of Sorbitan laurate, Span 80 and Brij 72.
53. The composition according to any one of the preceding items, wherein the surfactant is sugar based surfactant.
54. The composition according to any one of the preceding items, wherein the sugar based surfactant is selected from the group consisting of sucrose cocoate, sorbitan laurate and polysorbate.
55. The composition according to any one of the preceding items, wherein the sugar based surfactant has an HLB value between 9 and 16.
56. The composition according to any one of the preceding items, wherein the lipid is paraffin oil.
57. The composition according to any one of the preceding items, wherein the composition further comprises one or more additional components that absorbs or reflects some of the sun's ultraviolet (UV) radiation.
58. The composition according to any one of the preceding items, wherein the composition further comprises an organic chemical compounds that absorb ultraviolet light; an inorganic particulates that reflect, scatter, and absorb UV light (such as titanium dioxide, zinc oxide, or a combination of both); and/or an organic particulates that mostly absorb UV light like organic chemical compounds, but contain multiple chromophores that reflect and scatter a fraction of light like inorganic particulates.
59. The compound according to any one of the preceding items, wherein the composition further comprises one or more compounds selected from the group consisting of p-Aminobenzoic acid, Padimate O, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, Titanium dioxide, Zinc oxide, 4-Methylbenzylidene camphor, Bisoctrizole, Bemotrizinol, Tris-Biphenyl Triazine, bisimidazylate, Drometrizole Trisiloxane, Benzophenone-9,Octyl triazone, Diethylamino Hydroxybenzoyl Hexyl Benzoate, Iscotrizinol, Polysilicone-15 and Isopentyl-4-methoxycinnamate.

60. The composition according to any one of the preceding items, wherein the composition comprises or consists essentially of about:
a) 0.01 to 1 wt % peptide or peptide derivative;
b) 0.01 to 2 wt % saccharide or modified saccharide;
c) 35 to 50 wt % petrolatum; and
d) 40 to 60 wt % isopropyl myristate.

61. The composition according to any one of the preceding items, wherein the composition comprises 50 wt % isopropylmyristate, 0.2 wt % Sorbitan laurate and 3 wt % glyceryl behenate or 6 wt % carnauba wax 62. The composition according to any one of the preceding items, wherein the composition comprises 40 to 60 wt % isopropylmyristate, 2 to 6 wt % Sorbitan laurate and 2 to 6 wt % glyceryl behenate.

63. The composition according to any one of the preceding items, wherein the composition comprises 50 wt % isopropylmyristate, 0.2 wt % Sorbitan laurate and 6 wt % carnauba wax.

64. The composition according to any one of the preceding items, wherein the composition comprises or consists essentially of about:
a) 0.01 to 1 wt % peptide or peptide derivative;
b) 0.01 to 2 wt % saccharide or modified saccharide;
c) 1 to 6 wt % glyceryl behenate;
d) 35 to 45 wt % petrolatum;
e) 40 to 60 wt % isopropyl myristate; and
f) 2 to 10 wt % surfactant, such as sorbitan laurate.

65. The composition according to any one of the preceding items, wherein the composition comprises or consists essentially of about:
a) 0.01 to 1 wt % peptide or peptide derivative;
b) 0.01 to 2 wt % sucrose, mannitol or glucose;
c) 1 to 8 wt % glyceryl behenate or carnauba wax;
d) 35 to 45 wt % petrolatum;
e) 40 to 60 wt % isopropyl myristate; and
f) 2 to 10 wt % surfactant, such as sorbitan laurate.

66. The composition according to any one of the preceding items, wherein the composition comprises or consists essentially of about:
a) 0.01 to 1 wt % peptide or peptide derivative;
b) 0.01 to 4 wt % saccharide or modified saccharide;
c) 85 to 95 wt % lipid; and optionally
d) 2 to 10 wt % surfactant.

67. The composition according to any one of the preceding items, wherein the lipid comprises isopropyl myristate, petrolatum and glyceryl behenate.

68. The composition according to any one of the preceding items, wherein the composition comprises or consists essentially of the peptide; sucrose; glyceryl behenate; petrolatum; isopropyl myristate; and sorbitan laurate.

69. The composition according to any one of the preceding items, wherein the saccharide is sucrose and the lipid is isopropyl myristate.

70. The composition according to any one of the preceding items, wherein the composition further comprises petrolatum.

71. The composition according to any one of the preceding items, wherein the composition further comprises glyceryl behenate.

72. The composition according to any one of the preceding items, wherein the composition further comprises sorbitan laurate.

73. The composition according to any one of the preceding items, wherein the composition comprises or consists essentially of about:
a) 0.01 to 1 wt % peptide or peptide derivative;
b) 0.01 to 2 wt % sucrose;
c) 1 to 6 wt % glyceryl behenate;
d) 35 to 45 wt % petrolatum;
e) 40 to 60 wt % isopropyl myristate; and
f) 2 to 10 wt % sorbitan laurate.

74. The composition according to any one of the preceding items, wherein the composition comprises or consists essentially of about:
a) 0.01 to 1 wt % peptide or peptide derivative;
b) 0.01 to 1 wt % sucrose;
c) 1 to 6 wt % glyceryl behenate;
d) 35 to 45 wt % petrolatum;
e) 40 to 60 wt % isopropyl myristate; and
f) 2 to 6 wt % sorbitan laurate.

75. The composition according to any one of the preceding items, wherein the composition comprises or consists essentially of about:
a) 0.2 wt % peptide or peptide derivative;
b) 0.4 wt % sucrose;
c) 3 wt % glyceryl behenate;
d) 42.4 wt % petrolatum;
e) 50 wt % isopropyl myristate; and
f) 4 wt % sorbitan laurate.

76. The composition according to any one of the preceding items, wherein the composition comprises or consists essentially of about:
a) 1 wt % peptide;
b) 2 wt % sucrose;
c) 95 wt % lipid; and optionally
d) 2 wt % Sorbitan laurate.

77. The composition according to any one of the preceding items, wherein the sum of the amounts in percent of the components does not exceed 100%.

78. The composition according to any one of the preceding items, wherein the composition is essentially water free.

79. The composition according to any one of the preceding items, wherein the composition comprises one or more further active pharmaceutical ingredients.

80. The composition according to any one of the preceding items, wherein the composition is a pharmaceutical composition.

81. The composition according to any one of the preceding items, wherein the composition is in the form on an ointment, a powder, a spray, a lotion, a gel, a foam, a make-up or a cream.

82. The peptide, peptide derivative or composition according to any one of the preceding items for use in medicine.

83. The peptide, peptide derivative or composition according to any one of the preceding items for use in the treatment of dermatological conditions.

84. The peptide, peptide derivative or composition for use according to item 6, wherein the dermatological condition is a hypo-pigmentary condition.

85. The peptide, peptide derivative or composition according to any one of the preceding items, for use in stimulating melanin pigmentation of the skin in a mammal.

86. The peptide, peptide derivative or composition according to any one of the preceding items, for use in preventing or decreasing melanin pigmentation of the skin in a mammal.
87. The peptide, peptide derivative or composition for use according to any one of the preceding items, wherein the mammal is a human.
88. Use of the peptide, peptide derivative or composition according to any one of the preceding items in the manufacture of a medicament for treatment or prevention of a disease or condition associated with depigmentation and/or hypopigmentation.
89. Use of the peptide, peptide derivative or composition according to any one of the preceding items in the manufacture of a medicament for treatment or prevention of a disease or condition associated with hyperpigmentation.
90. Use of a peptide, peptide derivative or composition according to any one of the preceding items for stimulating melanin pigmentation of the skin and/or hair in a mammal.
91. Use of a peptide, peptide derivative or composition according to any one of the preceding items for decreasing melanin pigmentation of the skin and/or hair in a mammal.
92. Use of a peptide, peptide derivative or composition according to any one of the preceding items for non-therapeutic increase of melanin pigmentation of skin and/or hair of a subject.
93. The use of a peptide, peptide derivative or composition according to any one of the preceding items, wherein the mammal is a human.
94. The use of a peptide, peptide derivative or composition according to any one of the preceding items, wherein the use is cosmetic.
95. The use of a peptide, peptide derivative or composition according to any one of the preceding items, wherein the use is medical.
96. A method of modulating melanin pigmentation of the skin and/or hair, said method comprising administering to a subject in need thereof, an effective amount of the peptide, peptide derivative or composition according to any one of the preceding items.
97. A method of treatment or prevention of a disease or condition associated with depigmentation and/or hypopigmentation, said method comprising administering to a subject in need thereof, an effective amount of the peptide, peptide derivative or composition according to any one of the preceding items.
98. A method of treatment or prevention of a disease or condition associated with hyperpigmentation, said method comprising administering to a subject in need thereof, an effective amount of the peptide, peptide derivative or composition according to any one of the preceding items.
99. A cosmetic method of darkening of skin and/or hair color, the method comprising administering to a subject a peptide, peptide derivative or composition according to any one of the preceding items.
100. A cosmetic method of lightening of skin and/or hair color, the method comprising administering to a subject a peptide, peptide derivative or composition according to any one of the preceding items.
101. The method according to any one of the preceding items, wherein the administration is topical.
102. The method according to any one of the preceding items, wherein the composition exhibits the ability to modulate melanogenesis or melanin transfer.
103. The method according any one of the preceding items, wherein the subject is a human.
104. A method of manufacturing a composition according to any one of the preceding items, comprising the following steps:
    a) mixing the peptide with a saccharide;
    b) freeze drying the mixture of a);
    c) mixing b) with a lipid and a surfactant;
    d) grinding the mixture of c); and
    e) optionally mixing the mixture of d) with a lipid and a thickener.
105. The method according to any one of the preceding items, wherein the lipid is isopropyl myristate.
106. The method according to any one of the preceding items, wherein the surfactant is sorbitan laurate.

EXAMPLES

Example 1. Peptides

It was hypothesized that the native tetrapeptide Asn-Ala-His-Met (SEQ ID NO: 2) could itself affect the binding between BMP-6 and its receptor. To test this hypothesis, such a peptide (Asn-Ala-His-Met, Peptide 1, SEQ ID NO: 2) were synthesised, as well as a number of peptide analogues; where with residues modified, omitted or replaced by alanine, namely: Ala-His-Met; Ala-Ala-His-Met (Peptide 3, SEQ ID NO: 3); Asn-Ala-Ala-Met (Peptide 4, SEQ ID NO: 4); and Ala-His-Met (Peptide 2). These four peptides were synthesized using a peptide synthesizer. Peptides were dissolved in distilled water to a concentration of 10 mg per ml (see molarities in Table 1). Topical application was in 25 µl aliquots per skin equivalent sample, per time-point for dosing.

TABLE 1

Molarities for a peptide concentration of 10 mg/mL.

| SEQ ID NO | Peptide | Molecular weight | Molarity (mM) |
|---|---|---|---|
| 2 | Peptide 1 | 471.2 | 21.2 |
| | Peptide 2 | 357.1 | 28.2 |
| 3 | Peptide 3 | 428.2 | 23.4 |
| 4 | Peptide 4 | 405.2 | 24.7 |

Example 2. Skin Equivalent Culture

The aim of this study was to evaluate the effect of peptides 1, 3 and 4 on pigmentation of skin samples by photographic assessment of pigmentation.

Materials and Methods

Pigmented skin equivalents (SEs), Melanoderms Mel-300-A (Asian donor) and Mel-300-C-2 (Caucasian donor) were obtained from Mattek Ltd together with the associated media EPI-100-NMM-113 and Sterile Stainless Steel Washers. The skin equivalent surface area was 63.6 $mm^2$. Other equipment used included SMZ1000 Stereo Microscope (Nikon); UC30 Microscope Camera (Olympus); Phosphate-Buffered Saline (PBS); 6-well Tissue Culture Plates (Sarstedt); Image J software (https://imagej.nih.gov); Paintshop Photo Pro Software (Corel). The Melanoderms were prepared by carefully removing the agarose with sterile forceps and placing them in pre-warmed culture medium (37° C.) for an hour prior to treatment. The Melanoderms were then topically treated (without rubbing) with 25 μl of the various peptides, dissolved in $dH_2O$ at 10 mg/ml. They were placed onto 2 stacked sterile washers in 6 well plates. 5 ml of culture medium was then added to each well and the SEs were maintained at 37° C., 5% $CO_2$ in a humidified incubator. Generally the SEs were treated up to 5 times (including on day 0) over 0-20 days, with the culture medium being replaced every other day. The SEs were examined and removed from culture when skin darkening became visible.

The pigmentation of the Melanoderms was macroscopically assessed by capturing high-resolution images using the Olympus microscope camera. The SEs were removed from the culture medium and washed with 1 ml PBS. They were then placed into a 6-well plate containing 1 ml PBS/well and images captured at ×8 magnification. The images were then processed using Image J & Paintshop Photo Pro software, to determine a quantifiable pixel area, which equated to the level of pigmentation present in the skin equivalent. The image brightness was normalised and the image gray-scaled using Paintshop Photo Pro, then Image J was used to threshold the image. The pigmentation was quantified by assessing total pixel area of pigmentation coverage in a fixed sample area. An ANOVA test (Dunnett's post-test) was used for the statistical analysis.

Three different experiments were conducted. In the first, skin equivalents from both donors were included, and in experiment 2 and 3, only the Asian donor was included. The SE of the Asian donor from the first experiment received 5 treatments of 25 μl of peptide solution at 10 mg/ml; starting on the first day following receipt then on days 3, 5, 9 and 12. Peptides 1 (SEQ ID NO: 2), 3 (SEQ ID NO: 3) and 4 (SEQ ID NO: 4) were tested. The images were taken on Day 14. In experiment 2, peptide 3 and 4 were selected for testing to see if it had any efficacy in reducing melanin content or the distribution of melanin throughout the SE. This time, 5 SEs were used per treatment to improve statistical robustness. The experiment was continued for 20 days with treatments on days 0, 3, 7 and 12 and medium changes every other day. In experiment 3 a more highly pigmented SE (Asian donor melanocytes) was used and with an increased sample size with n=7 per treatment. Again, peptide 1, 3 and 4 were tested. The SEs were allowed to settle then topical treatment started on day 0 with each peptide prepared in dH20 and applied at a concentration of 10 mg/ml in a dose of 25 μl. Treatment was repeated on days 5, 9, 12 and 15 with medium changed every other day.

Results

Figure 1A:
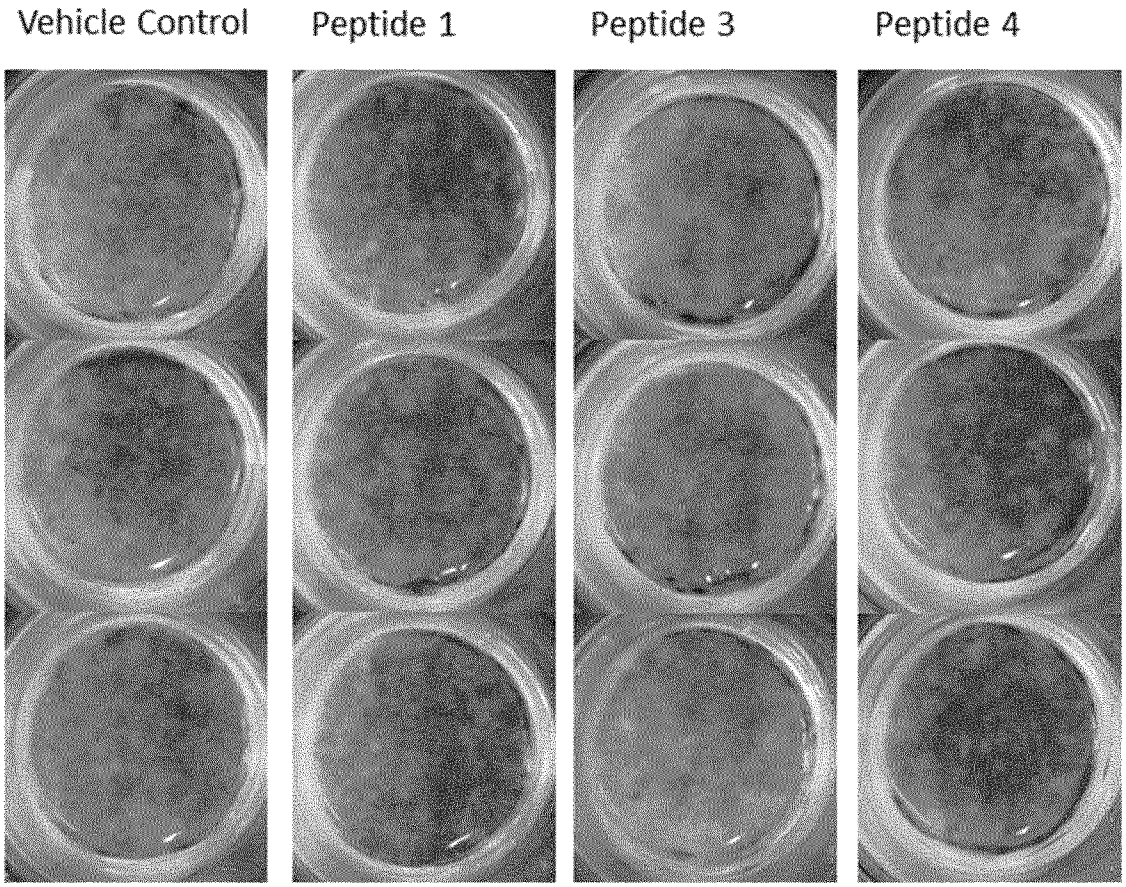
FIG. 1. Skin equivalent (SE) culture
Figure 1B:
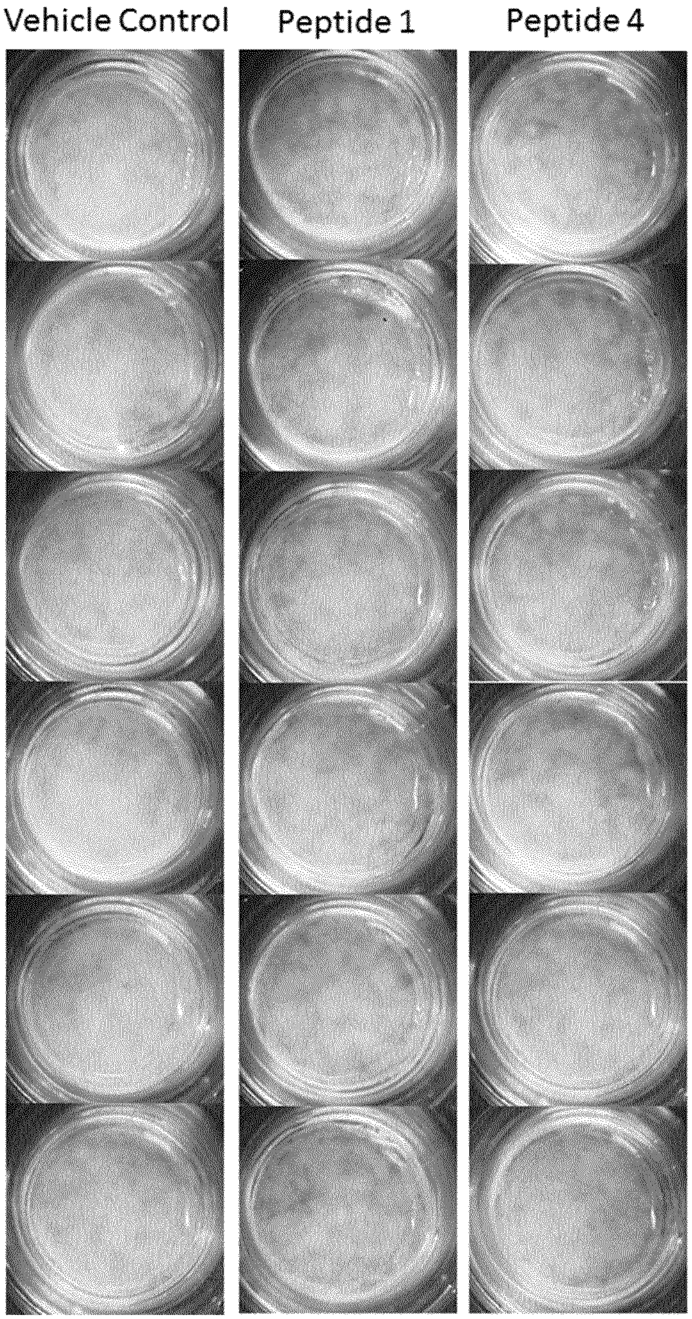
Figure 1C:
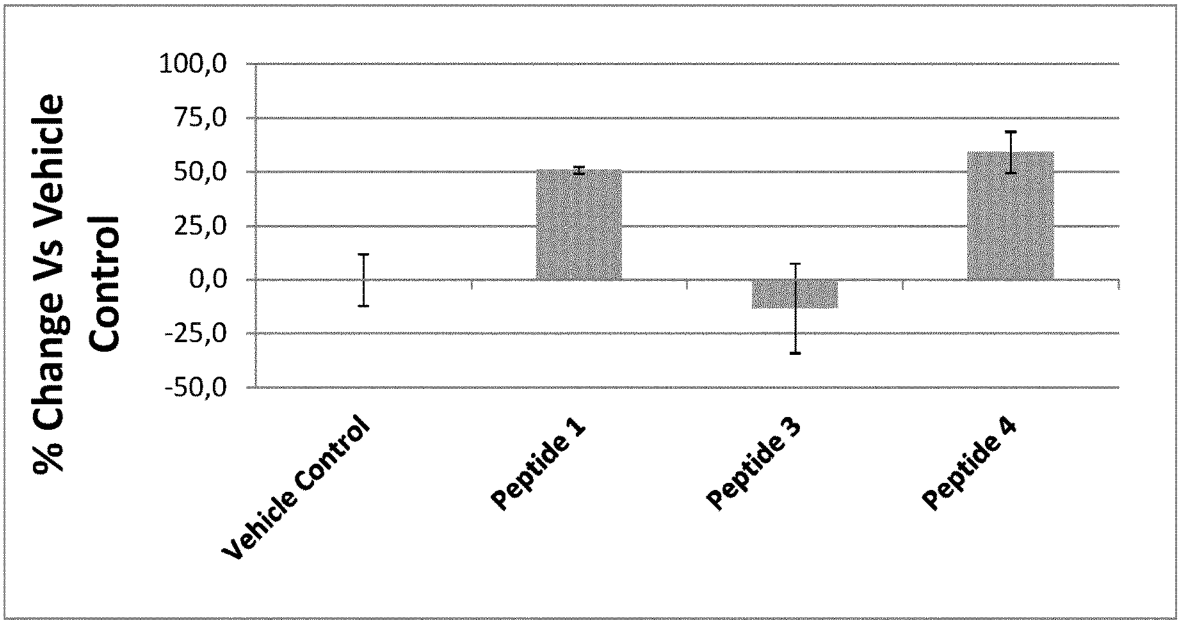

Analyzing the Asian donor of the first experiment, it was apparent that peptide 3 was equivalent or slightly less pigmented than the vehicle control and that both peptide 1 and 4 were more pigmented compared to the vehicle (statistically significant) (FIGS. 1A and B). In the same experiment, peptide 1 and 4 were tested on the skin equivalent from the Caucasian donor. In this experiment, the vehicle control samples were paler after 20 days in culture, while Peptides 1 and 4 showed a somewhat darker and mottled appearance (FIG. 1C).

Figure 1D:
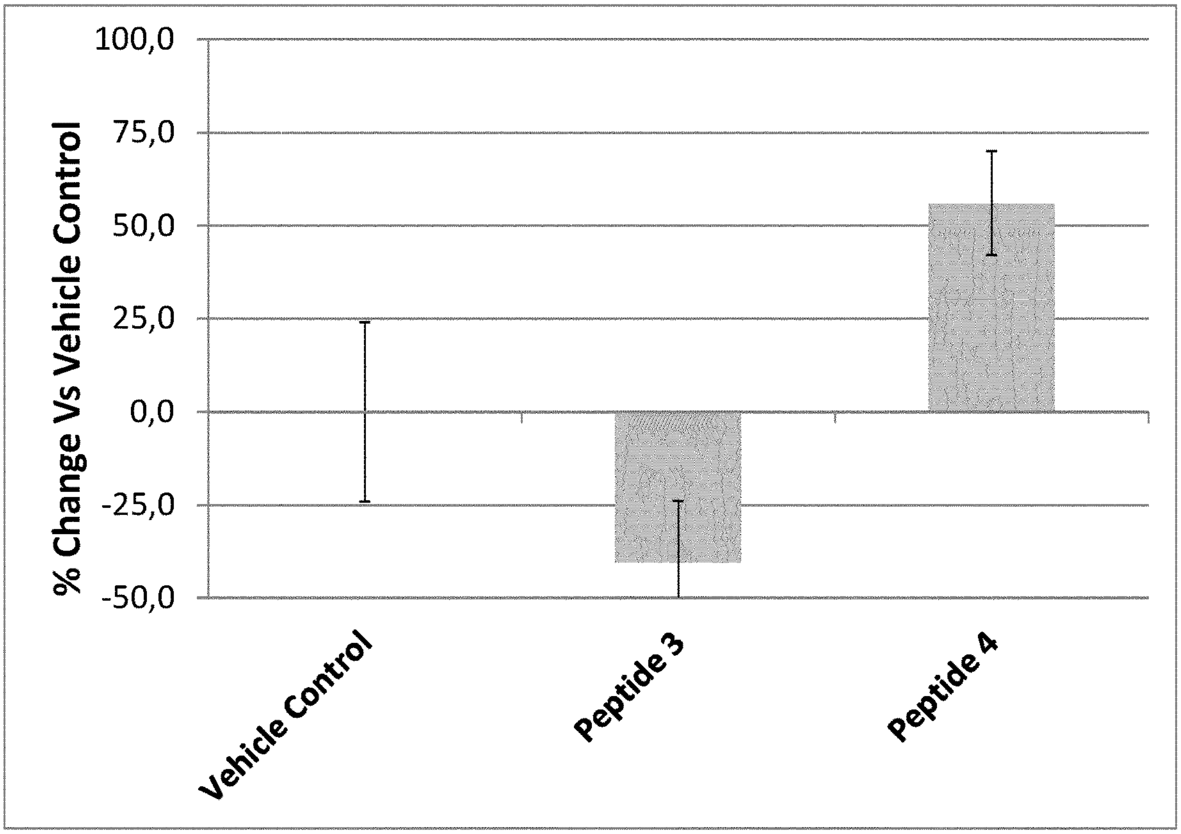

In experiment 2, peptide 3 and 4 were selected for experimental testing, on the basis that peptide 4 showed the greatest response in terms of melanin increase in experiment 1, as well as peptide 3. Also in this experiment, peptide 4 showed an increase in pigmentation compared to the vehicle control samples (statistically significant) (FIG. 1D). Peptide 3 showed a slight decrease in pigmentation but with a fairly large degree of error, hence not statistically significant (FIG. 1D).

Figure 1E:
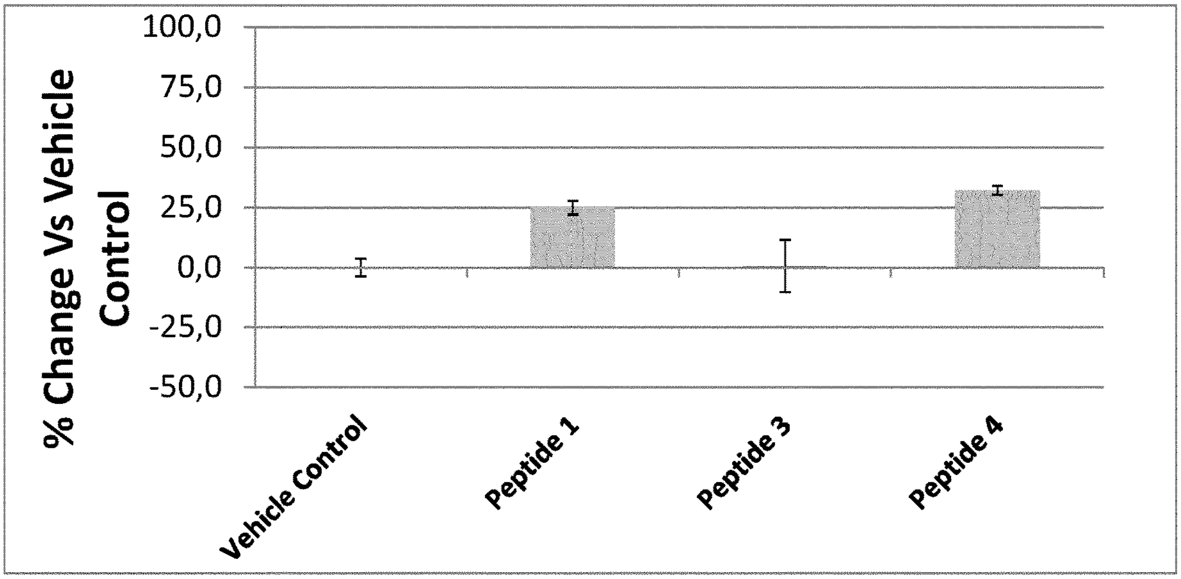

Experiment 3 further showed an increase in pigmentation by peptide 1 and 4 (statistically significant compared to the vehicle controls) (FIG. 1E). Peptide 3 appeared to have little effect.

Conclusions

The results from these three experiments suggest that peptide 1 and 4 are able to increase pigmentation in skin samples. Peptide 3 appeared to have little effect on pigmentation, suggesting that peptide 3 is not influencing pigmentation in any reproducible manner, as determined over 20 days in these SE cultures.

Example 3. Total Melanin Assay

The aim of this study was to study the total melanin content in skin equivalents.

Materials and Methods

The skin equivalents used in this study was from the same donors as in Example 2. The determination of the total melanin content of the skin equivalent was determined using a total melanin assay.

The total melanin content of the SE was calculated by dissolving the SE in Soluene and reading the absorbance against a standard curve. The SEs were removed from culture on day 20 and washed with PBS. They were then transferred to a glass centrifuge tube and 500 μl Soluene added. The tubes were then covered with PARAFILM®, gently vortexed and placed on the Thermomixer at 50° C. for 1 hour. The tubes were then gently vortexed and 150 μl of the sample and synthetic melanin standards pipetted in triplicate into a glass 96 well plate. The absorbance was then measured at 490 nm on a Spectrophotometer. Results are presented in μg/ml against a standard curve. The change of melanin content is expressed as a percentage change versus vehicle control samples. An ANOVA (with Dunnett's post-test) was used for the statistical analysis.

Three experiments were conducted, and the same donors were used as in Example 2. The sample sizes were as follows: experiment 1 n=2, experiment 2 n=4 and experiment 3 n=7. Peptides 1 (SEQ ID NO: 2), 3 (SEQ ID NO: 3) and 4 (SEQ ID NO: 4) were tested.

Results

In experiments 1 and 3, an increase in melanin content was observed in the skin samples treated with peptide 1 and 4 (FIGS. 2A, C and D). In experiment 2, peptide 4 exhibited a significant increase in melanin content, while no difference was seen in skin samples treated with peptide 3 (FIGS. 2B and E).

Conclusions

Similar to Example 2, peptides 1 and 4 appears to lead to an increase in pigmentation, further supporting the pro-pigmentary effect of these peptides on skin samples.

Example 4. H&E and Warthin Starry Staining of Skin Equivalents (SEs)

The aim of this study was to visualize and quantify the melanin distribution in the skin sections and to ensure that the histology of the SEs was normal.

Materials and Methods

Two skin equivalents (SEs) were used from one Asian donor.

The analysis was achieved using the Warthin Starry assay using our recently published method (Joly-Tonetti et al 2016) and hematoxylin&eosin (H&E) staining.

The SEs were stained with Warthin Starry stain to visualise and quantify the melanin in sections. The SEs were removed from culture on day 20 and washed in PBS. They were then flash frozen in liquid nitrogen and mounted in OCT for sectioning. 10 μm sections were cut using a cryostat, the sections collected on slides and fixed in Acetone for 10 mins. The OCT was removed from the section by washing in acidulated water for 20 mins. The slides were then incubated in 1% silver nitrate solution for 1 hour at 43° C. 41.5 ml 2% silver nitrate, 103.5 ml 5% gelatin & 55 ml 0.15% hydroquinone was then mixed and warmed to 54° C. The slides were stained for 2 mins then the staining was stopped by running the slides under hot tap water. Slides were then mounted using Histomount. Brightfield images were captured using a Nikon Eclipse microscope. Image analysis of the melanin density in sections was performed using Image J and densitometric thresholding. Results are presented in pixel intensity units. For the hematoxylin&eosin (H&E) staining, the SEs were flash frozen, sectioned and fixed as above. The slides were then washed in $dH_2O$ to remove the OCT for 20 mins. Haematoxylin was filtered using filter paper into a Coplin jar. Further Coplin jars were also prepared containing the following: Tap Water, Scott's Tap Water, 0.25% Eosin, 50% Ethanol, 70% Ethanol, 90% Ethanol, Ethanol and Histoclear. The slides were then placed into Haematoxylin for 2 mins, and then placed into tap water for 30 secs, Scott's Tap Water for 1 min & Eosin for 2 mins. The slides were then dehydrated through the Ethanol (1 min each) then placed into Histoclear for 2 mins and mounted using Histomount. Brightfield images were captured using a Nikon Eclipse microscope.

Results

Figure 3A:
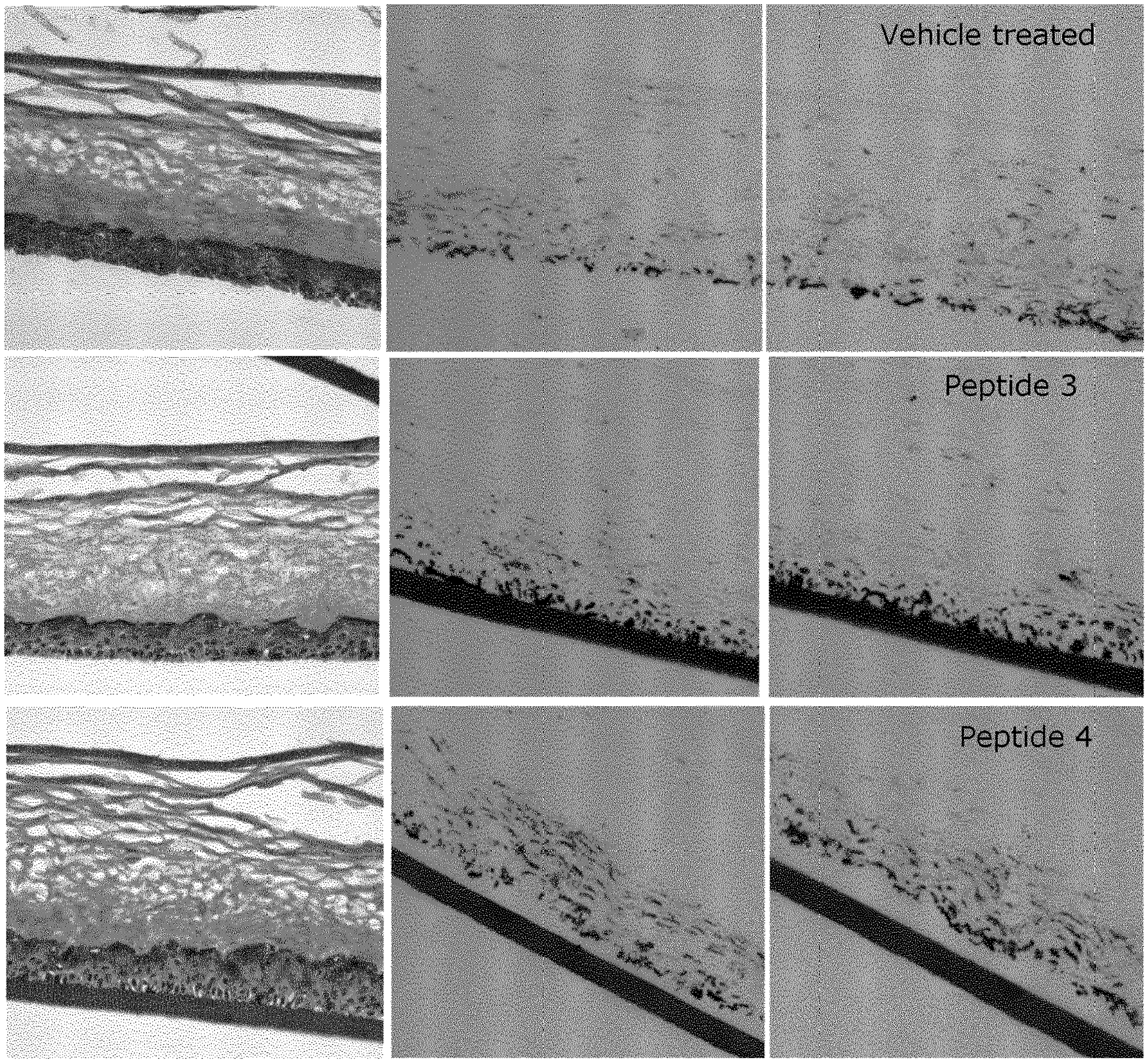
Figure 3B:
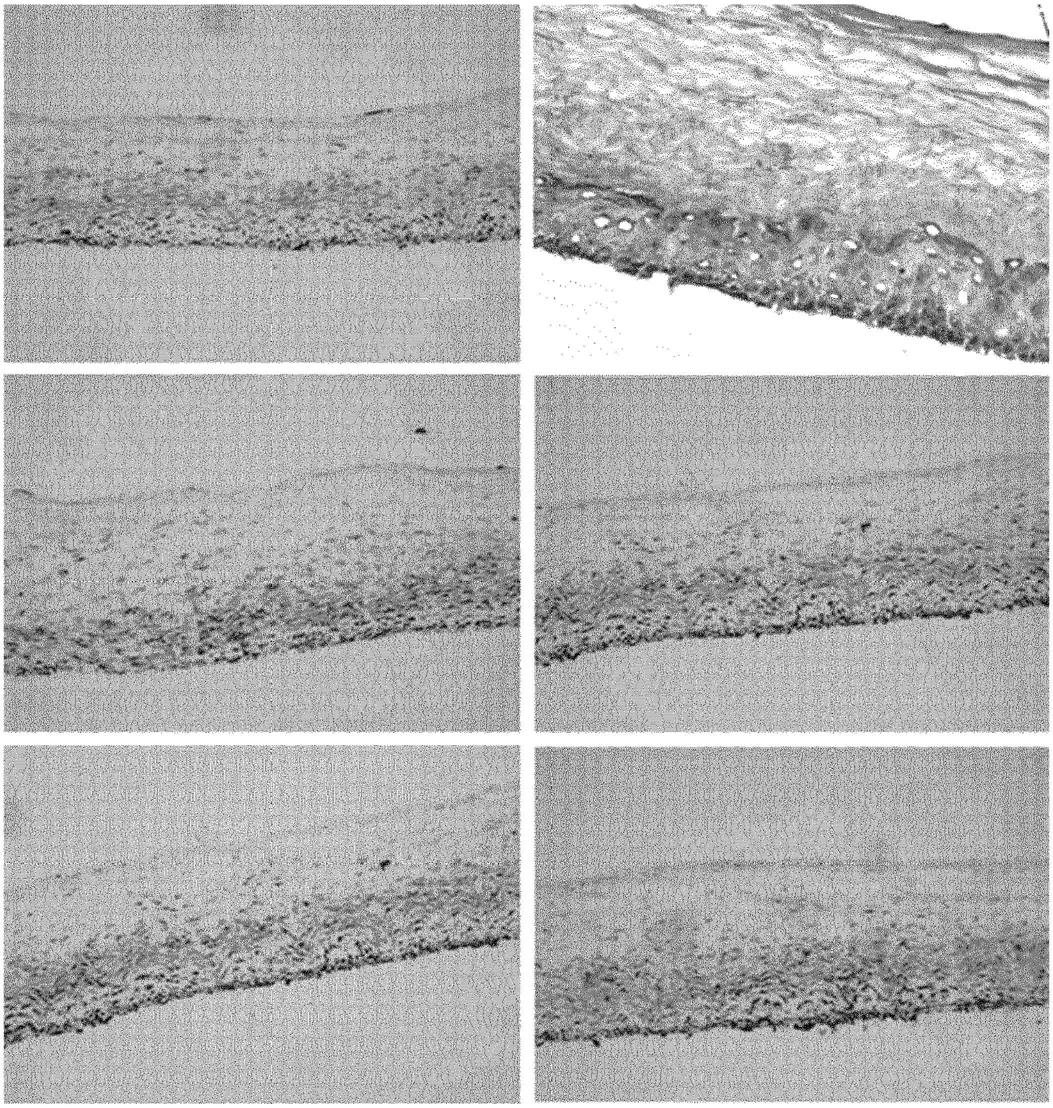
Figure 3C:
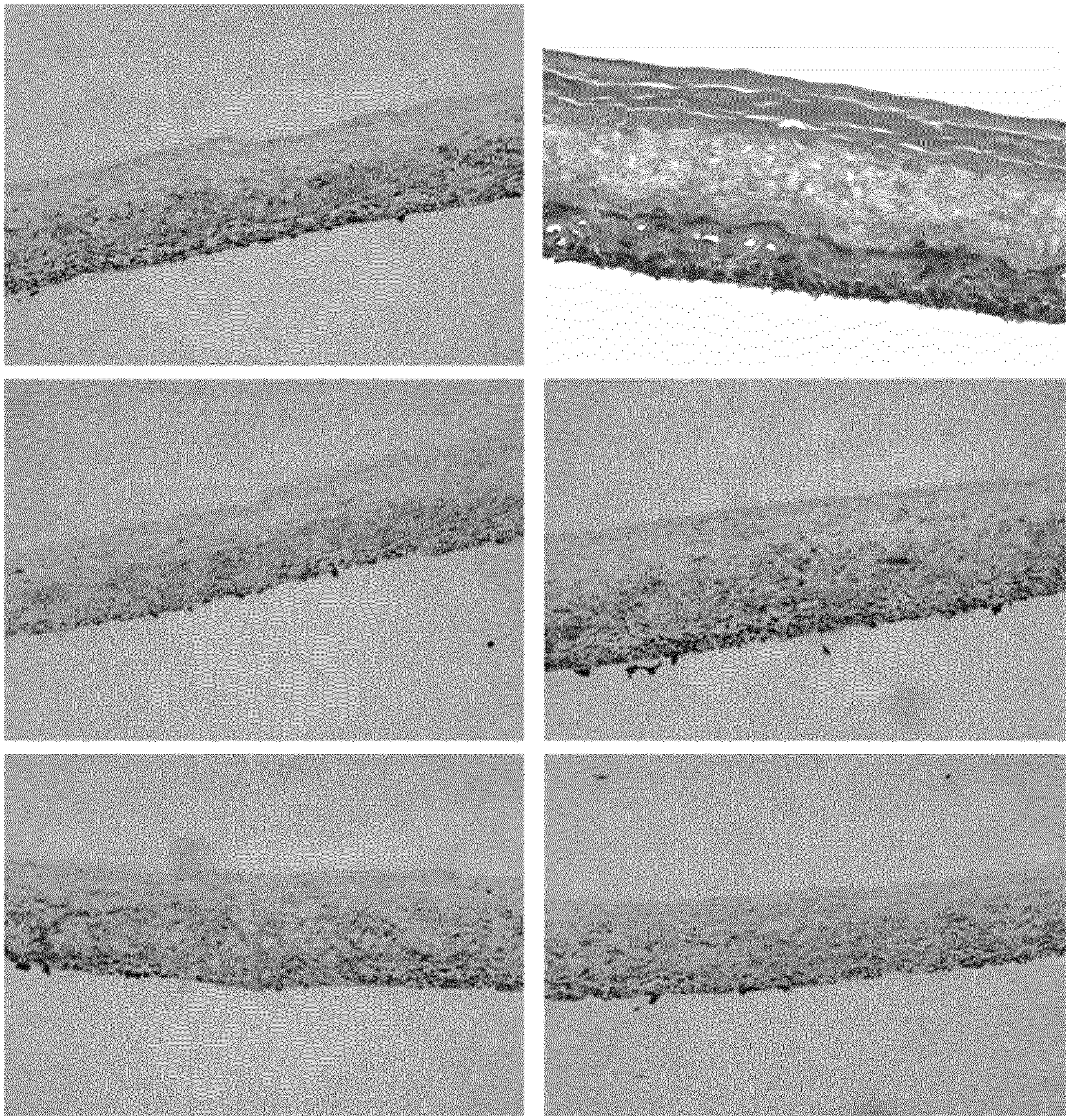
Figure 3D:
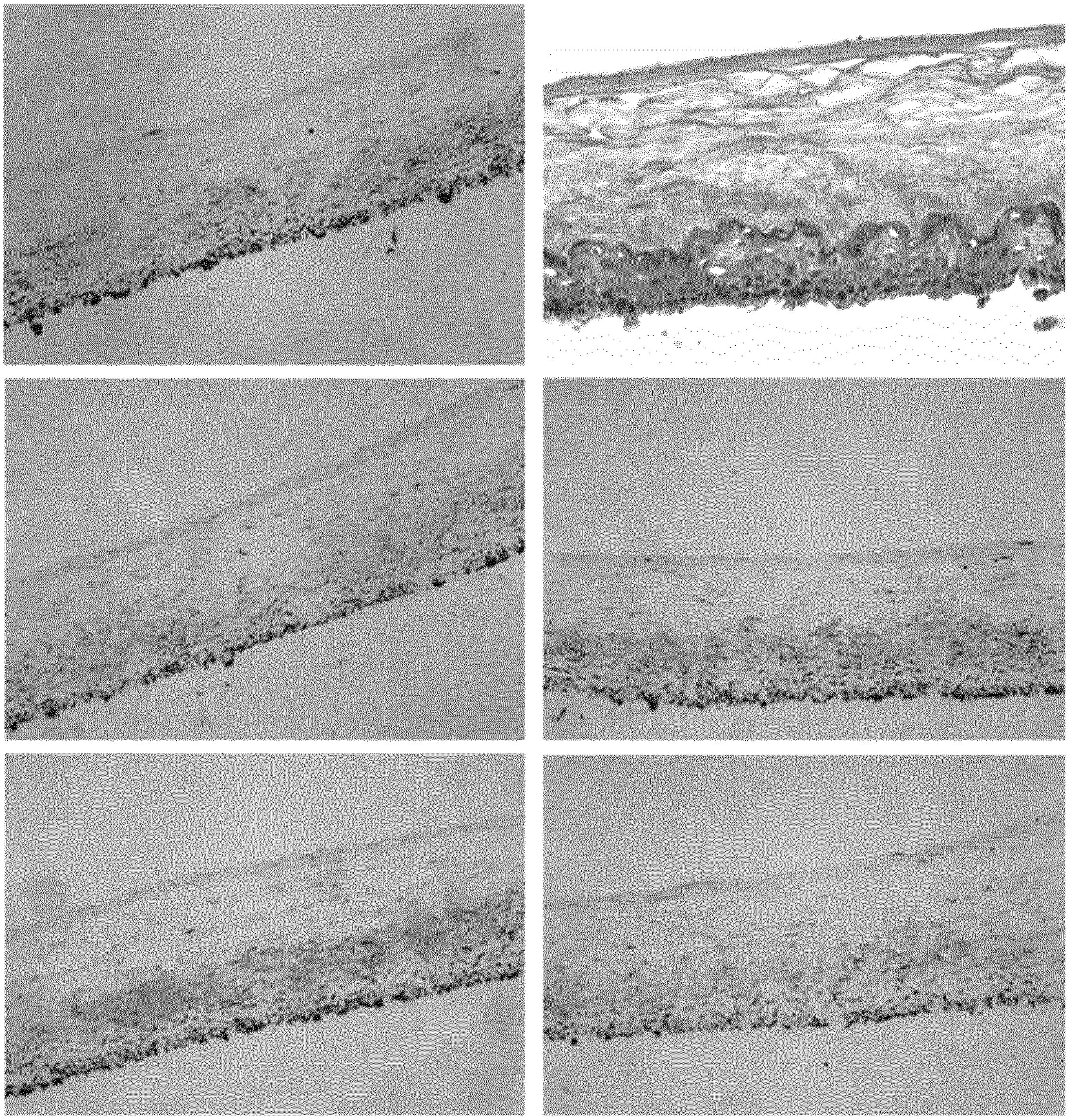
Figure 3E:
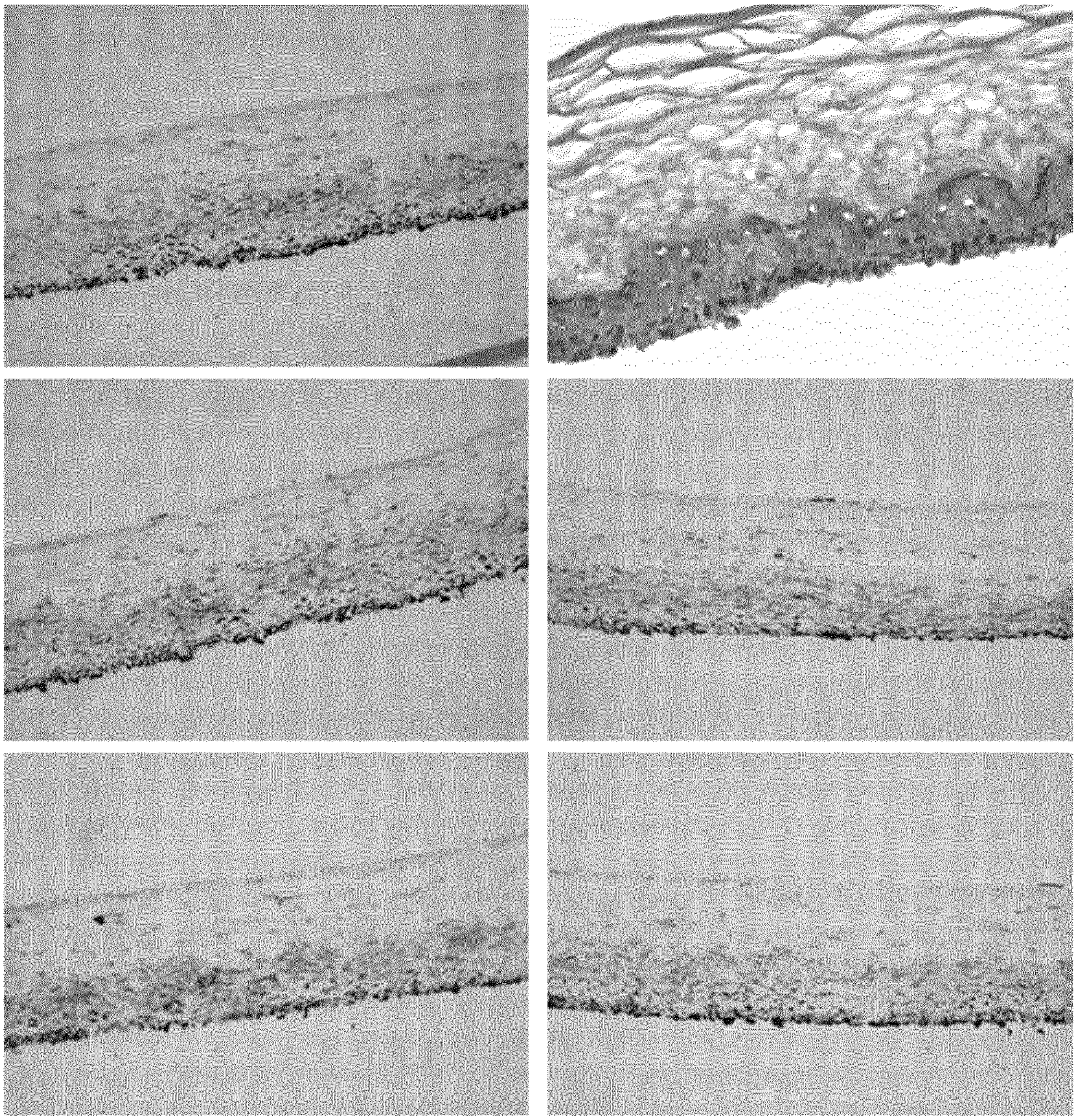

In one of the donors, treatment with peptide 4 (SEQ ID NO: 4) increased the melanin content in the SEs across all layers, while peptide 3 (SEQ ID NO: 3) appeared to lead to a reduction in melanin in the upper epidermal layers (Stratum spinosum, granulosum and corneum) (FIG. 3A). In the second donor, peptides 1 (SEQ ID NO: 2) and 4 (SEQ ID NO: 4) visibly increased melanin content in the SEs (FIGS. 3B and C). Peptide 3 did not appear to have any obvious effect (FIG. 3D). All the SEs (including untreated control) showed some epidermal vacuolation. The distribution of melanin within the SEs looked normal in the untreated SEs with the majority of the melanin in the viable epidermis and granules distributed well into the Stratum corneum (FIG. 3E).

Conclusions

All the SEs (including untreated control) from the second donor showed some epidermal vacuolation, likely due to the SEs beginning to degrade by day 20, which is the life of SEs according to the manufacturer. This has also contributed to the slightly "spongy" appearance of the most newly formed stratum corneum. In conclusion, peptide 4 (SEQ ID NO: 4) increased the melanin content in both donors and peptide 1 (SEQ ID NO: 2) in one of the donors.

Example 5. FOL-005 Stability Testing

Preparation of peptide having the sequence VDTYDGDISVVYGLR (FOL-005, SEQ ID NO: 6) suspension studied in a screening stability study.

Preparation of FOL-005 Suspensions

Aerosil was charged into a beaker. Paraffin oil was added, and the mixture was stirred until a homogenous viscous gel was formed. The gel was heated to 70° C. under stirring, and homogenized at 70° ° C., until a homogenous gel was obtained. The homogenous gel was cooled to room temperature. Isopropyl myristate was added and the mixtured was stirred until a homogenous suspension was formed. The homogenous suspension was added into a beaker charged with FOL-005 sucrose particles and Sorbitan laurate, and the mixture was homogenized at 70° C., until a homogenous suspension was formed.

Results

TABLE 2a

Results from stability testing of FOL-005 (sodium salt) in three suspensions.

| Ingredient | Batch no<br>ISM16192<br>S1 | <br>ISM16193<br>S2<br>% (w/w) | <br>ISM16194<br>S3 |
|---|---|---|---|
| FOL-005 sucrose 1:1 pH 7 | 0.20 | 0.20 | 0.20 |
| (FOL-005)* | (0.086) | (0.086) | (0.086) |
| Sorbitan laurate | — | — | 0.02 |
| Paraffin oil | 96.80 | 86.74 | 86.74 |
| Isopropyl myristate | — | 10.04 | 10.04 |
| Aerosil R972 | 3.00 | 3.01 | 3.00 |
| Total | 100.0 | 100.0 | 100.0 |

TABLE 2a-continued

Results from stability testing of FOL-005 (sodium salt) in three suspensions.

| Ingredient | Batch no ISM16192 S1 | ISM16193 S2 % (w/w) | ISM16194 S3 |
|---|---|---|---|
| Initial analysis | | | |
| FOL-005 HPLC assay recovery % | 57.3[1] | 77.5[1] | 106.7[1] |
| Sum related subst., % rel. area | Not detected[2] | Not detected[2] | Not detected[2] |
| beta-asp, RRT = 0.96 | Not detected[2] | Not detected[2] | Not detected[2] |
| 4 weeks, 25° C. | | | |
| FOL-005 HPLC assay recovery % | 85.9[4] | 73.2 | 106.2 |
| Sum related subst., % rel. area | 7.22 | 4.93 | 3.55 |
| beta-asp, RRT = 0.96 | Not detected | Not detected | Not detected |
| RRT = 0.98 | 3.42 | 0.15 | Not detected |
| 10 weeks, 25° C. | | | |
| FOL-005 HPLC assay recovery % | 92.5 | 98.7 | 110.2 |
| Sum related subst., % rel. area | 10.13 | 6.11 | 4.04 |
| beta-asp, RRT = 0.96 | Not detected | Not detected | Not detected |
| RRT = 0.98 | 5.30 | 0.34 | 0.12 |
| RRT = 1.09 | 1.64 | 1.55 | 2.31 |
| RRT = 1.21 | 1.47 | 2.48 | Not detected |
| 4 weeks, 30° C. | | | |
| FOL-005 HPLC assay recovery % | 90.1 | 97.5 | 80.8 |
| Sum related subst., % rel. area | 9.81 | 4.74 | 4.15 |
| beta-asp, RRT = 0.96 | Not detected | Not detected | Not detected |
| RRT = 0.98 | 5.83 | 0.17 | 0.13 |

*FOL-005 sucrose 1:1 contains 45.8% FOL-005

[1]Different sample preparation steps in the analytical method were evaluated. The data given in the Table is from the analysis giving the highest recovery.

[2]Rel. substances could not be detected due to too small sample quantity (0.25 g sample per 25 ml solution).

[3]Sample preparation tetrahydrofuran and water

[4]Sample preparation Span, water and acetonitrile

Conclusion

The recovery of FOL-005 in S3 was low when stored at 25° C. It was however increased when the analytical sampling preparation was improved. No beta-ASP (degradation product of FOL-005) was detected in the three suspensions after 4 and 10 weeks storage at 25° C. and 4 weeks storage at 30° C. Low amounts of degradation product RRT=0.98 was seen in S2 and S3, while higher amounts were seen in S1. It was concluded that the chemical stability of FOL-005 looks promising in S2 and S3.

Tables 2b-d show the purity of FOL-005. Data is also shown in FIGS. 4-6.

TABLE 2b

Purity of FOL-005 in different pH. Purity FOL-005 (%)

| weeks | months | buffer pH 5 | buffer pH 6 | buffer pH 7 | buffer pH 7.6 | water free |
|---|---|---|---|---|---|---|
| 0 | 0 | 98.66 | 98.64 | 98.85 | 99 | 98.17 |
| 1 | 0.25 | 92.63 | 96.06 | 97.42 | 97.15 | |
| 4 | 1 | 78 | 90 | 92 | 92 | 99.06 |
| 8 | 2 | 65.42 | 84.53 | 87.84 | 87.83 | 98.04 |
| 12 | 3 | 55.44 | 76.89 | 82.96 | 82.65 | 98.33 |
| | 6 | | | | | 98.34 |
| | 9 | | | | | 98.22 |
| | 12 | | | | | 97.7 |

TABLE 2c

Purity of FOL-005 with different conditions of isopropyl myristate (IPM). Purity FOL-005 (%)

| | Months 0 | 1 | 2 | 3 | 6 | 9 | 12 |
|---|---|---|---|---|---|---|---|
| Un-Dried IPM 2-8 C. | 99.04 | 99.28 | | 98.84 | 99.04 | | 99 |
| Dried IPM 2-8 C. | 98.17 | 98.18 | | 98.13 | 97.95 | | 97.81 |
| Un-Dried IPM 25 C. | 99.04 | 98.48 | 98.16 | 97.04 | 96.73 | 95.77 | 95.57 |
| Dried IPM 25 C. | 98.17 | 99.06 | 98.04 | 98.33 | 98.34 | 98.22 | 97.7 |
| Un-Dried IPM 30 C. | 99.04 | 98.01 | 97.68 | 96.24 | 95.91 | 94.24 | 94.59 |
| Dried IPM 30 C. | 98.17 | 97.38 | | | 97.74 | | 96.86 |

TABLE 2d

Purity of FOL-005 with or without sucrose at different temperatures. Purity FOL-005 (%)

| | Months 0 | 1 | 2 | 3 | 6 | 9 | 12 |
|---|---|---|---|---|---|---|---|
| Sucrose 2-8 C. | 99.04 | 99.28 | | 98.84 | 99.04 | | 99 |
| Sucrose 25 C. | 99.04 | 98.48 | 98.16 | 97.04 | 96.73 | 95.77 | 95.57 |
| Sucrose 30 C. | 99.04 | 98.01 | 97.68 | 96.24 | 95.91 | 94.24 | 94.59 |
| Na 2-8 C. | 98.99 | 99.13 | | 98.23 | 98.8 | | 98.96 |
| Na 25 C. | 98.99 | 98.29 | 97.17 | 95.17 | 93.1 | 92.86 | 92.7 |
| Na 30 C. | 98.99 | 96.82 | 95.74 | 94.06 | 93.58 | 91.79 | 90.47 |

Conclusion

It is demonstrated that FOL-005 was degraded at various pH, whereas the degradation was very limited in water free conditions. Further, dried IPM resulted in less degradation than un-dried IPM of FOL-005 at 25 and 30° ° C., and sucrose particles resulted in less degradation than Na sait of FOL-005 at 25 and 30° C.

Example 6. Lyophilization of FOL-005 with Mannitol

The possibility to make particles of FOL-005 (acetate-salt) by freeze drying and test the compatibility between peptide and a prototype vehicle.

Materials and Methods

The following chemicals were used in this study:

Mannitol, Sodium hydroxide, HCl (37%), API, FOL-005 Ac-salt, Beta-Asp FOL-005 (degradation product), Deionized water, Paraffin oil, Glycerol, Propylene glycol, Cithrol™ DPHS, Tween 60 BergaBest MCT oil 60/40.

Preparation of Solution for Freeze Drying Test

The mixtures given in Table 3a were prepared for freeze drying. The mixtures were dispensed into 2 ml glass vials. The number of glass vials per mixture is given in the table below. Each vial contains approximately 2 mg FOL-005.

TABLE 3a

Composition mixtures prepared for freeze drying

| Ingredient | FOL-005: Mannitol 2:1, pH 7.1 % | FOL-005: Mannitol 1:1, pH 7.1 % |
|---|---|---|
| FOL-005 Ac-salt | 0.10 | 0.11 |
| Mannitol | 0.05 | 0.10 |
| Sodium hydroxide 0.1M to pH 7.4 | 1.62 | — |
| Sodium hydroxide 1M to pH 7.4 | — | 0.20 |
| HCl 0.1M to pH 3.5 | — | 0.14 |
| Water | 98.23 | 99.46 |
| Total | 100.00 | 100.00 |
| pH | 7.5 | 7.5 |
| Number of vials | 22 | 22 |

TABLE 3a-continued

Composition mixtures prepared for freeze drying

| Ingredient | FOL-005: Mannitol 2:1, pH 7.1 % | FOL-005: Mannitol 1:1, pH 7.1 % |
|---|---|---|
| | Batch no | |
| Ingredient | ISM16111 FOL-005/ Mannitol 2:1 pH 3.5 | ISM16113 FOL-005/ Mannitol 1:1, pH 3.5 |
| ISM16111 | 98 | |
| ISM16113 | | 98 |
| HCl 0.1M to pH 3.5 | 2 | 2 |
| Total | 100 | 100 |
| pH | 3.5 | 3.5 |
| Number of vials | 3 | 3 |

*pH tends to decrease with time. pH was determined to 7.1 before freeze drying.

Freeze Drying Conditions

Vials were first stored at −35° C. for 2 hours and then transferred quickly to the Freeze dryer. Vials were freeze dried under vacuum at −55° C. for 24 hours.

Preparation of Formulations for Compatibility Testing

The compatibility between FOL-005 powder and vehicle excipients was tested in pure paraffin oil and in one potential formulation. The composition of the formulations is presented in Table 53b.

TABLE 3b

Formulations for compatibility testing of freeze dried powder.

| Ingredient | Formulation A % (w/w) | Formulation B % (w/w) |
|---|---|---|
| Paraffin oil | 100.00 | 15.50 |
| Glycerol | — | 44.83 |
| Propylene glycol | — | 30.10 |
| Cithrol ™DPHS | — | 2.64 |
| Tween 60 | — | 2.61 |
| BergaBest MCT oil 60/40 | — | 4.33 |
| Total | 100.00 | 100.00 |

Assay Method

The test items were analyzed using the HPLC-UV method Assay of FOL-005 in formulation by HPLC. The concentration of FOL-005 was determined and beta-asp FOL-005 as well.

Results

The results from the HPLC analysis of freeze dried powder of FOL-005 in shown in Table 4a-c.

TABLE 4a

Results from HPLC analysis of freeze dried powders of FOL-005 (acetate salt) and mannitol, initial analysis and after 4 weeks storage at 2-8° C. and room temperature.

| | ISM16113 FOL-005:Mannitol 1:1, pH 3.5 | ISM16113 FOL-005:Mannitol 1:1, pH 7.1 | ISM16111 FOL-005:Mannitol 2:1, pH 3.5 | ISM16111 FOL-005:Mannitol 2:1, pH 7.1 |
|---|---|---|---|---|
| Initial analysis | | | | |
| FOL-005 in weight % | 43.6 | 44.6 | 52.8 | 59.1 |
| Sum related subst., % | 5.61 | 4.91 | 5.02 | 4.81 |
| rel. area | | | | |
| beta-asp, RRT = 0.96 | 0.34 | 0.29 | 0.32 | 0.32 |

TABLE 4a-continued

Results from HPLC analysis of freeze dried powders of FOL-005 (acetate salt) and mannitol, initial analysis and after 4 weeks storage at 2-8° C. and room temperature.

| | ISM16113 FOL-005:Mannitol 1:1, pH 3.5 | ISM16113 FOL-005:Mannitol 1:1, pH 7.1 | ISM16111 FOL-005:Mannitol 2:1, pH 3.5 | ISM16111 FOL-005:Mannitol 2:1, pH 7.1 |
|---|---|---|---|---|
| 4 weeks, 2-8° C. | | | | |
| FOL-005 in weight % | 44.4 | 45.9 | 59.4 | 61.3 |
| Sum related subst., % rel. area | 3.53 | 3.49 | 3.27 | 3.73 |
| beta-asp, RRT = 0.96 | 0.46 | 0.50 | 0.51 | 0.51 |
| RRT = 1.04 | 0.37 | 0.32 | 0.39 | 0.33 |
| RRT = 1.05 | na | na | na | na |
| 4 weeks, room temperature | | | | |
| FOL-005 in weight % | — | 44.7 | — | 59.5 |
| Sum related subst., % rel. area | — | 6.30 | — | 6.20 |
| beta-asp, RRT = 0.96 | — | 031 | — | 0.50 |
| RRT = 1.04 | — | 0.46 | — | 0.45 |
| RRT = 1.05 | — | 2.09 | — | 2.13 |

TABLE 4b

Results from HPLC analysis of freeze dried powder of FOL-005 (acetate salt) and mannitol in paraffin oil (formulation A), initial analysis and after 4 weeks storage at 2-8° C. and room temperature.

| | FOL-005:Mannitol 1:1, pH 3.5 + Formulation A | FOL-005:Mannitol 1:1, pH 7.1 + Formulation A | FOL-005:Mannitol 2:1, pH 3.5 + Formulation A | FOL-005:Mannitol 2:1, pH 7.2 + Formulation A |
|---|---|---|---|---|
| Initial analysis | | | | |
| FOL-005 in weight % | 0.077 | 0.092 | 0.085 | 0.087 |
| Sum related subst., % rel. area | 4.23 | 4.51 | 4.85 | 4.27 |
| beta-asp, RRT = 0.96 | 0.22 | 0.21 | 0.22 | 0.23 |
| 4 weeks, 2-8° C. | | | | |
| FOL-005 in weight % | 0.097 | 0.096 | 0.088 | 0.090 |
| Sum related subst., % rel. area | 3.36 | 2.99 | 2.81 | 2.78 |
| beta-asp, RRT = 0.96 | 0.60 | 0.26 | 0.26 | 0.24 |
| RRT = 1.04 | 0.55 | 0.35 | 0.41 | 0.46 |
| 4 weeks, room temperature | | | | |
| FOL-005 in weight % | — | 0.092 | — | 0.091 |
| Sum related subst., % rel. area | — | 2.90 | — | 3.16 |
| beta-asp, RRT = 0.96 | — | 0.40 | — | 0.32 |
| RRT = 1.04 | — | 0.42 | — | 0.45 |

TABLE 4c

Results from compatibility testing of freeze dried powder of FOL-005 (acetate salt) and mannitol in formulation B, initial analysis and after 4 weeks storage at 2-8° C. and room temperature.

| | FOL-005:Mannitol 1:1, pH 3.5 + Formulation B | FOL-005:Mannitol 1:1, pH 7.1 + Formulation B | FOL-005:Mannitol 2:1, pH 3.5 + Formulation B | FOL-005:Mannitol 2:1, pH 7.2 + Formulation B |
|---|---|---|---|---|
| Initial analysis | | | | |
| FOL-005 in weight % | na | na | 0.085 | 0.073 |
| Sum related subst., % rel. area | na | na | 5.96 | 7.52 |
| beta-asp, RRT = 0.96 | na | na | 0.25 | 0.28 |

TABLE 4c-continued

Results from compatibility testing of freeze dried powder of FOL-005 (acetate salt) and mannitol in formulation B, initial analysis and after 4 weeks storage at 2-8° C. and room temperature.

| | FOL-005:Mannitol 1:1, pH 3.5 + Formulation B | FOL-005:Mannitol 1:1, pH 7.1 + Formulation B | FOL-005:Mannitol 2:1, pH 3.5 + Formulation B | FOL-005:Mannitol 2:1, pH 7.2 + Formulation B |
|---|---|---|---|---|
| 4 weeks, 2-8° C. | | | | |
| FOL-005 in weigth % | 0.057 | 0.067 | 0.080 | 0.068 |
| Sum related subst., % rel. area | 7.36 | 9.92 | 6.08 | 9.68 |
| beta-asp, RRT = 0.96 | na | na | na | na |
| RRT = 1.04 | 5.27 | 7.34 | 3.08 | 7.32 |
| 4 weeks, room temperature | | | | |
| FOL-005 in weight % | — | 0.024 | — | 0.027 |
| Sum related subst., % rel. area | — | 50.99 | — | 50.76 |
| beta-asp, RRT = 0.96 | — | na | — | na |
| RRT = 1.04 | — | 36.59 | — | 36.97 |

Conclusion

The acetate salt of FOL-005 was successfully freeze dried with mannitol as stabilizer. Two different pH of the lyophilisation mixtures, 3.5 and 7.1, and two different ration between FOL-005 and mannitol, 1:1 and 2:1, were tested. No difference in the chemical stability of the freeze dried powders due to pH or ration between FOL-005 and mannitol could be seen when stored at 2-8° C. for 4 weeks.

The freeze dried powder of FOL-005 and mannitol was chemically stable when stored at 2-8° C. for 4 weeks. When stored at room temperature for 4 weeks an increase in the sum of related substances could be seen from 5 to 6%.

The freeze dried powder of FOL-005 was found to be chemically stable when dispersed in formulation A, containing 100% paraffin oil, and stored at 2-8° C. and room temperature for 4 weeks.

The chemical stability was found to be poorer in formulation B, containing paraffin oil (16%), glycerol (45%), propylene glycol (30%), Cithrol (3%), Tween 60 (3%) and BergaBest MCT oil (4%). When stored at 2-8° C. for 4 weeks no change in the content of FOL-005 could be seen, but an increase in the amount of related substances could be seen, from 7.5 to 10%, as well as a difference in the pattern of related substances.

When stored at room temperature for 4 weeks the content of FOL-005 decreased 0.07% to 0.03% and the sum of related substances increased from 7.5 to 50.8.

Example 7: Thickening of Placebo Formulations

In this study, we have investigated the positivity to form viscous formulations with petrolatum and high concentration of isopropylmyristate.

Materials and Methods

Petrolatum/Isopropylmyristate Formulations

Petrolatum/isopropylmyristate mixtures were visually inspected to determine if formulations with high viscosity could be made using these two components. The compositions of the formulations manufactured are given in Table 5.

TABLE 5

Formulation compositions % (w/w).

| Ingredients | ISM17165 | ISM17166 | ISM17167 | ISM17168 |
|---|---|---|---|---|
| Isopropylmyristate | 50 | 30 | 20 | 10 |
| Petrolatum | 50 | 70 | 80 | 90 |
| Total | 100 | 100 | 100 | 100 |

Addition of Thickening Agents

In order to increase the viscosity of Petrolatum/Isopropylmyristate formulations, thickening agents were added and formulations were visually inspected. Formulations compositions are given in Table 6.

TABLE 6

Formulation compositions % (w/w).

| Ingredients | ISM17169 | ISM17170 | ISM17171 | ISM17172 |
|---|---|---|---|---|
| Isopropylmyristate | 50 | 30 | 50 | 30 |
| Petrolatum | 43.8 | 63.8 | 46.8 | 66.8 |
| Carnauba wax 2442 | 6 | 6 | — | |
| Glyceryl behenate | — | — | 3 | 3 |
| Sorbitan laurate | 0.2 | 0.2 | 0.2 | 0.2 |
| Total | 100 | 100 | 100 | 100 |

Placebo Formulations with Sucrose Particles

Centrifugation of formulations containing sucrose particles was performed in order to investigate particle sedimentation. 2% (w/w) sucrose were added to ISM17167-ISM17172 in Table 5 and 6 and 1% (w/w) sucrose were added to ISM17166. The formulations were mixed before they were centrifuged at 1000 rpm for 3 min and visually inspected.

Formulations with FOL-005 Particles

Particle sedimentation in selected formulations were also investigated by analysing the content of FOL-005 at different positions in tubes with centrifuged formulations. 0.2% (w/w) FOL-005 were added to the placebo formulations according to Table 7, the formulations were then mixed by magnetic stirring for 2 hours. Each formulation was distributed into two Eppendorf tubes whereof one was centrifuged for 3 min at 1000 rpm. Tubes were stored in a refrigerator until the content of FOL-005 was assayed. The analysis was performed by high-pressure liquid chromatography (RP-HPLC) and ultra violet detection (UV). The compounds were monitored at 220 nm. The unidentified related substances were quantified as % relative area. FOL-005 salt (sodium) was used as external standard.

TABLE 7

| Formulation compositions % (w/w) | | |
|---|---|---|
| Ingredients | ISM17180 | ISM17181 |
| FOL-005 (Na-salt) | 0.2 | 0.2 |
| Isopropylmyristate | 49.9 | 49.9 |
| Petrolatum | 43.7 | 46.7 |
| Carnauba wax 2442 | 6 | — |
| Glyceryl behenate | — | 3 |
| Sorbitan laurate | 0.2 | 0.2 |
| Total | 100 | 100 |

Results

Petrolatum/Isopropylmyristate Formulations

As described in Table 8 it was not possible to create nice viscous formulations with only isopropylmyristate and petrolatum. Formulations with 50% (w/w) or less petrolatum had a low viscosity while formulations with 70% (w/w) or higher content of petrolatum showed a tendency for phase separation.

TABLE 8

| Formulation properties. | | | | |
|---|---|---|---|---|
| | ISM17165 | ISM17166 | ISM17167 | ISM17168 |
| Isopropyl-myristate | 50 | 30 | 20 | 10 |
| Petrolatum | 50 | 70 | 80 | 90 |
| Viscosity | low | medium | medium | high |
| Appearance | OK | Tendency for separation | Tendency for separation | Tendency for separation |

Addition of Thickening Agents

Thickening agents were added to the formulations in order to increase the viscosity. In addition, 0.2% (w/w) Sorbitan laurate were added to the formulations as it has a stabilizing effect on FOL-005 particles. As seen in Table 9 addition of Carnauba wax and Glyceryl behenate had positive effect on the formulations. By adding these ingredients formulations with medium to high viscosity could be created.

TABLE 9

| Formulation properties. | | | | |
|---|---|---|---|---|
| | ISM17169 | ISM17170 | ISM17171 | ISM17172 |
| Isopropylmyristate | 50 | 30 | 50 | 30 |
| Petrolatum | 43.8 | 63.8 | 46.8 | 66.8 |
| Carnauba wax 2442 | 6 | 6 | — | |
| Glyceryl behenate | — | — | 3 | 3 |
| Sorbitan laurate | 0.2 | 0.2 | 0.2 | 0.2 |
| Viscosity | medium | high | medium | medium |
| Appearance | OK | OK | OK | Tendency for separation |

Conclusion

Mixtures of only isopropylmyristate and petrolatum were found to have either a low viscosity or showed a tendency for phase separation. However, by adding Glyceryl behenate or carnauba wax, the formulations showed good appearance and medium viscosity.

The particle sedimentation in the formulations with carnauba wax or glyceryl behenate was investigated and FOL-005 did not appear to sediment in these formulations.

Therefore, petrolatum formulations containing 50% (w/w) isoprpylmyristate 0.2% (w/w) Sorbitan laurate and 3% (w/w) glyceryl behenate or 6% (w/w) camnauba wax appeared to be promising alternative for FOL-005 particle suspensions.

Example 8. Ex Vivo Testing of Formulations of FOL-005 Particles

Materials and Methods

The compositions which were tested ex vivo are given in Table 10.

TABLE 10a

| Compositions tested ex vivo in experiment 1. | | | |
|---|---|---|---|
| Ingredient | ISM17209 “FOL-005/sucrose” % (w/w) | ISM17216 “FOL-005/Na” % (w/w) | ISM17213 “Placebo” % (w/w) |
| FOL-005 | 1.53 | 1.53 | — |
| Sucrose | 2.97 | — | — |
| Sorbitan laurate | 4.00 | 2.00 | 4.00 |
| Isopropyl myristate | 91.50 | 96.47 | 96.00 |
| Total (%) | 100.00 | 100.00 | 100.00 |
| Particle size, µm | | | |
| D[v, 0.1] | 2.4 | 2.7 | n.a. |
| D[v, 0.5] | 8.4 | 7.2 | n.a. |
| D[v, 0.9] | 25.8 | 15.6 | n.a. |

TABLE 10b

| Compositions tested ex vivo in experiment 2. | | | |
|---|---|---|---|
| Ingredient | FOL-005/sucrose suspension % (w/w) | FOL-005/sucrose formulation % (w/w) | Placebo % (w/w) |
| FOL-005: sucrose particles (contain 28% (w/w) FOL-005) | 4.52 | 1.56 | — |
| Sorbitan laurate | 4.02 | 4.01 | 4.03 |
| Isopropyl myristate (dried) | 91.46 | 41.53 | 50.01 |
| Petrolatum | — | 49.91 | 42.93 |
| Glyceryl behenate | — | 2.99 | 3.03 |
| Total (%) | 100.00 | 100.00 | 100.00 |

Skin Membranes

Pig ear full thickness membranes were prepared in the following way:

The pig ears were rinsed with lukewarm water to remove dirt, blood and wax. The ears were dreid using Kleenex and the bristles were removed with a beard trimmer. The inner ear skin was dermatomed into a thickness of approximately 600-700 µm and membranes from the dermatomed skin pieces were punched out. The thickness of the skin membranes was determined using a micrometer. The skin membranes were prepared the day before the ex vivo experiment and were stored, covered with aluminium foil, in a refrigerator until they were used. The skin membranes were put in the diffusion cell equipment and allowed to hydrate for one hour at the chosen temperature for the experiment. After one hour of hydration 100 mg per cell of each formulation was applied. Massage of the formulation was performed using a small metallic spoon, tops "dressed" in PARAFILM® and glass rods. At end of the experiment the skin samples were cleaned using tops and a solvent/fluid to remove access formulation. Water free propylene glycol was used as the solubility of FOL-005 is limited in propylene glycol (0.16 mg/ml in propylene glycol at room temperature) and it does not interact with sebum in the same way as non-polar solvents do.

Ex Vivo Experimental Design

The in vitro drug penetration experiment was performed in the following way: A 9 cell Frans cell equipment, Crown Glass Company, Inc., was used and, the volume of the cells were about 7 ml. Full thickness skin membranes were used for 48 h experiment time with sampling at the end of the experiment. The temperature was 32° C. in the Franz cells. Administration was performed two times, at 0 and 24 h. At each administration time, 100 mg of formulation was applied and gentle massage of the tissue was performed for 3 min using a glass rod. At termination of the experiment the skin samples are saved for analysis. In Table 10a and 10b the compositions for the formulations used in the ex vivo drug penetration experiments are given.

TABLE 11a

Experimental design of the ex vivo drug penetration experiment number 1.

| | Cell 1-3 | Cell 4-6 | Cell 7-9 |
|---|---|---|---|
| Membrane | Full-thickness pig ear skin | Full-thickness pig ear skin | Full-thickness pig ear skin |
| Receptor solution | PBS pH 7.4 | PBS pH 7.4 | PBS pH 7.4 |
| Formulation Batch no. | FOL-005/sucrose suspension ISM17209 | FOL-005/Na suspension ISM17216 | Placebo ISM17213 |
| Dose, at 0 and 24 hours | 100 mg | 100 mg | 100 mg |
| Sampling (h) | 48 | 48 | 24/48 |
| Administration (h) | 0 and 24 | 0 and 24 | 0 and 24 |
| Experimental time (h) | 48 | 48 | 48 |

TABLE 11b

Experimental design of the ex vivo drug penetration experiment number 2.

| | Cell 1-3 | Cell 4-6 | Cell 8 |
|---|---|---|---|
| Membrane | Full-thickness pig ear skin | Full-thickness pig ear skin | Full-thickness pig ear skin |
| Receptor solution | PBS pH 7.4 | PBS pH 7.4 | PBS pH 7.4 |
| Formulation Batch no. | FOL-005/sucrose suspension ISM 18097 | FOL-005/sucrose formulation ISM 18098 | Placebo ISM 18099 |
| Dose, at 0 and 24 hours | 100 mg | 100 mg | 100 mg |
| Sampling (h) | 48 | 48 | 48 |
| Administration (h) | 0 and 24 | 0 and 24 | 0 and 24 |
| Experimental time (h) | 48 | 48 | 48 |

At termination of the experiment the skin membranes were cleaned using tops and fluid. Each cell was washed 5 times with propylene glycol. The retrieved material was collected in vials. The membranes were removed from the equipment and snap frozen.

Maldi Mass Spectrometry Imaging (MSI)

Samples from the ex vivo experiment were analysed using MALDI mass spectrometry imaging. An analytical method was developed and the FOL-005 content and its distribution in the skin were studied.

Assessment and optimization of the detection of FOL-005 in the treated pig inner ear skin samples by MALDI FTICR MS Imaging was performed. Four different MALDI matrices (2,5-Dihydroxylbenzoic acid, α-Cyano-4-Hydroxycinnamic acid, 9-Aminoacridine and 1,5-Diaminoaphtalene) were evaluated and solvent optimization were performed for the optimal matrix.

Mass spectrometry imaging analysis was performed on pig inner ear skin biopsy samples by evaluating the frozen treated skin samples (n=1 per treated skin sample) and placebo sample (n=1 per placebo skin sample) using the developed MALDI-FTICR. In brief the frozen skin samples were sectioned in the hair follicles plane and one section per sample was analyzed by 7T-MALDI-FTICR imaging to determine the bio-distribution of FOL-005. Adjacent sections were stained with hematoxylin and eosin and were combined with the molecular distribution of FOL-005 to confirm the specific localization of the compound. The compound concentration per histological region was calculated by quantitative mass spectrometry imaging (QMSI) based on the generated MALDI images.

Results

Analysis of Applied Formulations

The formulations applied were analysed and the analysis was performed by high-pressure liquid chromatography (RP-HPLC) and ultra violet detection (UV). The compounds were monitored at 220 nm. The unidentified related substances were quantified as % relative area. FOL-005 salt (sodium) was used as external standard.

Experiment Number 1

The content of FOL-005 was found to be 1.33% (w/w) in ISM17209 and 1.13% (w/w) in ISM17216. The sum of related substances was 3.30% in ISM17209 and 3.39% in ISM17216, respectively. The measured particles size of the two formulations was about the same with an average size of 7.2 μm and 8.4 μm for FOL-005/sodium and FOL-005/sucrose particles, respectively.

Experiment Number 2

The content of FOL-005 were found to be 1.35% (w/w) in ISM18097 and 0.47% (w/w) in ISM18098. The sum of related substances was 1.65% in ISM18097 and 1.87% in ISM18098. The measured particles size of the two formulations was about the same with an average size of 7.2 μm and 8.4 μm for FOL-005/sodium and FOL-005/sucrose particles, respectively.

Ex Vivo Experiments

The preferred MALDI matrix were DHB 40 mg/mL methanol/water and 0.1% TFA (v/v).

The detection of FOL-005 in treated skin sections was also confirmed while no interfering peaks from the control tissue was detected.

Experiment Number 1

FOL-005 was detected in epidermis and dermis both in samples treated with FOL-005/sucrose suspension and FOL-005/Na suspension. Furthermore, FOL-005 was detected in a hair follicle of treated skin.

FOL-005 was detected in each treated skin while no signal was observed in the placebo treated sample. FOL-005 was mainly detected in epidermis with a decreasing gradient of FOL-005 from epidermis to dermis. This indicates that FOL-005 is transported by a trans-epidermal transport pathway in this experiment. However, some indications on a trans-follicular penetration could also be observed with some hair follicles having a larger signal intensity than the surrounding dermis.

A strong heterogeneity between molecular distributions and quantification was observed in both FOL-005/sucrose and FOL-005/Na treated samples. Penetration depth of FOL-005 into each tissue were calculated as the maximum distance from the surface in which FOL-005 was detected.

Furthermore, the concentration of FOL-005 in the tissues was registered for epidermis, dermis and as the global concentration. In Table 12 the penetration depth of FOL-005 and concentrations in the tissues are shown. Despite the heterogenicity and large variability, a slightly larger FOL-005 accumulation could be seen in FOL-005/sucrose treated skin (71.4±34.4 μg/g) compared to FOL-005/Na treated skin (35.7±24.1 μg/g). However, no difference in the penetration depth between FOL-005/sucrose suspension and FOL-005/Na suspension could be detected.

TABLE 12

Quantification of FOL-005 in the treated skin samples.

| Formulation | Penetration depth (mm) | Average penetration depth (mm) | Conc. Epidermis (μg/g) | Conc. Dermis (μg/g) | Conc. Global (μg/g) | Average conc. Dermis (μg/g) |
|---|---|---|---|---|---|---|
| FOL-005/sucrose suspension | 1.59 | 1.10 ± 0.34 | 308.5 | 97.5 | 105.5 | 71.4 ± 34.4 |
| | 0.90 | | 56.9 | 22.8 | 26.9 | |
| | 0.83 | | 165.7 | 93.9 | 62.7 | |
| FOL-005/Na suspension | 1.53 | 0.97 ± 0.42 | 330.3 | 69.4 | 70.8 | 35.7 ± 24.1 |
| | 0.83 | | 30.3 | 14.7 | 16.0 | |
| | 0.54 | | 66.0 | 23.1 | 28.0 | |
| Placebo | nd | | nd | nd | nd | nd |

Quantification of FOL-005 in hair follicles was determined and results are presented in Table 13. The percentage of hair follicles presenting FOL-005 were larger for skin samples treated with FOL-005/sucrose suspension (56%) compared to skin samples treated with FOL-005/Na suspension (21%). It appeared that the depth of hair follicles presenting FOL-005 detection was larger in skin biopsies treated with sucrose suspension (0.48±0.46 mm) than in skin biopsies treated with Na salt suspension (0.15±0.16 mm).

TABLE 13

Quantification of FOL-005 in the hair follicles.

| Formulation | Number of hair follicles analysed | Percentage of hair follicles presenting FOL-005 detection | Average depth of hair follicles presenting FOL-005 detection (mm) | Average concentration of FOL-005 in hair follicles (μg/g of tissue)* |
|---|---|---|---|---|
| FOL-005/sucrose suspension | 18 | 56% | 0.48 ± 0.46 | 45.5 ± 76.8 |
| FOL-005/Na suspension | 28 | 21% | 0.15 ± 0.16 | 64.6 ± 185.1 |

*"nd" values were considered as "0" for the average concentration calculation

The results indicate that the FOL-005/sucrose particle formulation have superior penetration properties compared to the FOL-005/sodium particle formulation. The observed differences could be an effect of the difference in particle composition where one of the applied formulations contains particles with FOL-005 and sucrose while the particles in the other formulation only contains FOL-005. The measured particles size of the two formulations are about the same with an average size of 7.2 μm and 8.4 μm for FOL-005/sodium and FOL-005/sucrose particles, respectively. However, there are other differences between the formulations which could have an effect. The amount of Sorbitan laurate differs between the formulations where the formulation with FOL-005/sucrose particles contains 4% Sorbitan laurate and the formulation with FOL-005/sodium particles contains 2% Sorbitan laurate.

Experiment Number 2

FOL-005 was weakly and heterogeneously detected in the epidermis and/or in the deep dermis of the tissues treated with formulations 18098. A more intense detection was observed in the pig ear samples treated with formulation 18097 with similar distribution in epidermis and deep dermis. Moreover, a passive diffusion from the epidermis to the dermis was observed. The dermis penetration was quantified at about 530 μm (high biological variability calculated at 51.3%).

A trans-follicular pathway was particularly highlighted in some of the tissues. In these tissues, global concentrations of FOL-005 were quantified at 144.0 μg/g of tissue with a low biological variability calculated at 8.1%.

| Formulation | Penetration depth (μm) | Average penetration depth (μm) | Conc. Epidermis (μg/g) | Conc. Dermis (μg/g) | Conc. Deep Dermis (μg/g) | Hair follicle | Global (μg/g) |
|---|---|---|---|---|---|---|---|
| FOL-005/ | 250 | | 194..5 | 91.2 | 234.4 | BLOQ | 156.9 |
| sucrose | 800 | 533 | 422.9 | 144.5 | 86.8 | 119.1 | 140.9 |
| suspension | 55 | | 523.4 | 104.9 | 88.7 | BLOQ | 134.3 |
| ISM 18097 | | | | | | | Mean |
| | | | | | | | 144.0 |
| FOL-005/ | 50 | 75 | 55.5 | BLOQ | 86.2 | BLOQ | 58.6 |
| sucrose | 100 | | 60.5 | BLOQ | | BLOQ | |
| formulation | | | BLOQ | BLOQ | BLOQ | BLOQ | |
| ISM 18098 | | | | | BLOQ | | |
| Placebo | na | na | na | na | na | na | na |
| ISM 18099 | | | | | | | |

BLOQ Below Limit of Quantification = 53.7 μg/g

In FIG. 7 overlays between Hematoxylin and Eosin adjacent section and FOL-005 molecular distribution can be seen for tissue samples treated with FOL-005/sucrose formulation.

Conclusion

Experiment Number 1

FOL-005 was successfully transported into the tissue. A difference was detected between tissue treated with FOL-005/sucrose particles and tissue treated with FOL-005/sodium particles. Accumulation of FOL-005 was larger in tissues treated with FOL-005/sucrose compared to tissue treated with FOL-005/sodium particles. The average dermal concentration of FOL-005 in the skin was 71.4±34.4 μg/g and 35.7±24.1 μg/g for tissue treated with FOL-005/sucrose and FOL-005/sodium particles respectively. FOL005 was found in follicles in all the treated tissues. A larger fraction of the follicles in the tissues were found to contain FOL-005 in tissue treated with FOL-005/sucrose particle (56%) compared to tissue treated with FOL-005/sodium particles (21%). Similarly, the average depth of hair follicles presenting FOL-005 were larger in tissue treated with FOL-005/sucrose particle (0.48±0.46 mm) compared to tissue treated with FOL-005/sodium particles (0.15±0.16 mm). The results indicate that FOL-005/sucrose particles could have superior penetration properties compared to FOL-005/sodium particles.

Experiment Number 2

FOL-005 was successfully transported into the tissue. A difference was detected between tissue treated with FOL-005/sucrose formulation and tissue treated with FOL-005/sucrose suspension. Accumulation of FOL-005 was larger in tissues treated with FOL-005/sucrose suspension compared to tissue treated with FOL-005/sucrose formulation. This is at least partly explained by the lower FOL-005 concentration in the formulation as compared to suspension.

A passive diffusion from the epidermis to the dermis was observed. A trans-follicular pathway was particularly highlighted in some of the tissues.

Data is shown in FIG. 7.

Example 9. In Vivo Testing

The present study was conducted to evaluate the hair growth promotion efficacy of FOL-005 in C57BL/6 mouse model by topical route of administration. Male C57BL/6 mice in stable telogen phase (resting phase) of hair growth cycle were used. The hair on the dorsal back of the animals was clipped and the area was treated with FOL-005 topical formulation, placebo formulation or commercially available Minoxidil 5%.

Materials and Methods

Three formulations of FOL-005 (High dose-0.5%, Medium dose-0.05% and Low dose-0.005%) along with placebo were screened for hair growth promotion efficacy by applying 50 μL/cm2 on the dorsal clipped skin of animals in the respective groups. The application regimen was total of 4 weeks (5 days/week) followed by 1 week of observation period. During the study, all the animals were observed for skin color change from pink skin (telogen) to black skin (anagen) and appearance of new hair re-growth. After completion of observation period, it was observed that FOL-005 formulation led to hair growth promotion efficacy in a dose response manner. A faster anagen induction was observed in High dose (3/7 animals) followed by Medium dose (2/7 animals) and in Low dose (1/7 animal). Hair growth was observed in high dose (3/7 animals) and in medium dose (1/7 animals). No hair growth was observed in low dose of the formulation. Visual melanogenesis was also observed in the peeled skin of 3/7 animals, 2/7 animals and 1/7 animal in the High, Medium and Low dose respectively.

Minoxidil solution (5%) was used as a control and was applied topically (50 μL/cm2) on the dorsal clipped skin of the mice. The application regimen was twice daily application for total of 4 weeks followed by 1 week of observation period. Anagen induction followed by hair growth was observed in 4/5 animals in this group. Visual melanogenesis was also observed in the peeled skin of 4/5 animals.

Conclusion

All the three topical formulations of FOL-005 (High dose, Medium dose and Low dose) demonstrated hair growth promotion efficacy in a dose dependent manner with highest hair growth promotion efficacy in High dose (0.5%) followed by Medium dose (0.05%) and then in Low dose (0.005%).

Data is shown in FIG. 8.

Example 10. Method of Manufacturing Composition

In brief the manufacturing process is described as follows: FOL-005 Sodium salt was freeze dried together with sucrose. The freeze-dried particles were mixed with dried Isopropyl myristate and Sorbitan laurate and then a ball milling step was performed.

The three excipients (Sorbitan laurate, Glyceryl behenate, Petrolatum) were added to the reactor at ambient temperature. The reactor was fitted with a stirrer. The excipients were mixed at room temperature until a homogenous viscous gel was formed. The reactor was then heated to 75° C. under stirring and then cooled to room temperature. Thereafter the ball milled FOL-005/sucrose—Isopropyl myristate suspension was added to the reactor and the mixture was stirred until a homogeneous mixture was obtained.

Example 11. Compositions Comprising Peptides

In this study, compositions comprising a number of representative peptides (see table 14) were manufactured. Further, the compositions were stored for 4 weeks at 20° C. to investigate the stability of the peptides in the compositions.

TABLE 14

Peptides.

| SEQ ID NO | Number of amino acids | Amino acid sequence | Name |
|---|---|---|---|
| | 3 | GHK | GHK |
| 8 | 9 | CYIQNCPLG | Oxytocin |
| 9 | 15 | VDVPNGDISLAYGLR | FOL-004 |
| 10 | 16 | KPLAEIDSIELSYGIK | FOL-014 |
| 11 | 25 | GKYGFYTHVFRLKKWI QKVIDQFGE | FOL-199 |
| 12 | 37 | LLGDFFRKSKEKIGKEFK RIVQRIKDFLRNLVPRTES | LL-37 |

Manufacture

Each peptide was lyophilized together with sucrose in a w/w-ratio 2:1 (Sucrose/Peptide) according to standard lyophilization methods.

Span20 was mixed with IPM to obtain a 4% (w/w) homogenous solution.

The peptide-sucrose was added to the Span20-IPM mixture to obtain a 0.4% suspension with regard to the peptide content. Using a standardized bead, wet-milling method the peptide-sucrose particles were micronized in the Span20-IPM suspension.

An ointment base was produced by mixing 89.5% Petrolatum, 4.2% Span20 and 6.3% Glyceryl behenate (w/w %). The mixture was heated to 75° C. during stirring. The stirring was continued until glyceryl behenate was dissolved. Then the ointment base was cooled to room temperature under gentle stirring.

When the ointment base had been cooled to room temperature, the ointment base was added to the separate peptide suspensions to obtain 0.2% ointments with regard to peptide concentration. The mixture was stirred at ambient temperature for 2 hours. The total composition is given in table 15.

TABLE 15

Total composition.

| Component | Amount (wt %) |
|---|---|
| Peptide | 0.20 |
| Sucrose | 0.40 |
| Span20 | 4.0 |
| Isopropyl myristate (IPM) | 50.0 |
| Petrolatum | 42.4 |
| Glycerol behenate | 3.0 |

Stability Study

Samples of the separate formulations were stored at 20° C. Further, samples of PBS solutions of oxytocin and FOL-004, respectively, were prepared and stored at 20° C.

Analysis of peptide purity in ointment and PBS solutions was performed using standard HPLC-UV-DA methods when the samples were freshly prepared (time 0) and after 1, 2 and 4 weeks. Data is shown in FIG. 9.

Example 12. Compositions Comprising Peptides 1 and 4

In this study, compositions comprising of peptides 1 and 4 were manufactured. Further, the compositions were stored for 12 weeks at 20° C. to investigate the stability of the peptides in the compositions.

Manufacture

Each peptide was lyophilized together with sucrose in a w/w-ratio 2:1 (Sucrose/Peptide) according to standard lyophilization methods.

Span20 was mixed with IPM to obtain a 4% or 2% (w/w) homogenous solution. The peptide-sucrose was added to the Span20-IPM mixture to obtain a 0.4, 1 or 2% suspension with regard to the peptide content. Using a standardized bead, wet-milling method the peptide-sucrose particles were micronized in the Span20-IPM suspension.

The ointment base was produced by mixing either 89.1% Petrolatum, 4.2% Span20 and 6.7% Glyceryl behenate for formulation B or 91.7% Petrolatum, 2.0% Span20 and 6.2% Glyceryl behenate for formulation C (w/w %). The mixture was heated to 75° C. during stirring. The stirring was continued until glyceryl behenate was dissolved. Then the ointment base was cooled to room temperature under gentle stirring.

When the ointment base had been cooled to room temperature, the ointment base was added to the separate peptide suspensions to obtain 0.4, 1.0 and 2% ointments with regard to peptide concentration for formulation B and 0.4% ointments with regard to peptide concentration for formulation C. The mixture was stirred at ambient temperature for 2 hours. The total composition is given in table 15.

In addition formulation A was prepared by mixing 98.8% ready-made placebo formulation with 1.2% lyophilized Sucrose/Peptide dry powder (w/w-ratio 2:1) resulting in a 0.4% ointments with regard to peptide concentration.

TABLE 16

Total composition.

| | Formulation [Amount (wt %)] | | | | |
|---|---|---|---|---|---|
| Component | A 0.4% | B 0.4% | B 1.0% | B 2.0% | C 0.4% |
| Peptide | 0.40 | 0.40 | 1.0 | 2.0 | 0.40 |
| Sucrose | 0.80 | 0.80 | 2.0 | 4.0 | 0.80 |

TABLE 16-continued

| Total composition. | | | | | |
|---|---|---|---|---|---|
| | Formulation [Amount (wt %)] | | | | |
| Component | A 0.4% | B 0.4% | B 1.0% | B 2.0% | C 0.4% |
| Span20 | 4.0 | 4.0 | 4.0 | 4.0 | 2.0 |
| Isopropyl myristate (IPM) | 50.0 | 50.0 | 50.0 | 50.0 | 50.0 |
| Petrolatum | 41.8 | 41.8 | 40.0 | 37.0 | 43.8 |
| Glycerol behenate | 3.0 | 3.0 | 3.0 | 3.0 | 3.0 |

Stability Study

Samples of the separate formulations were stored at 20° C. Further, samples of PBS solutions of 0.4% peptide 1 and 4, were prepared and stored at 20° C.

Analysis of peptide purity in ointment and PBS solutions was performed using standard HPLC-UV-DA methods when the samples were freshly prepared (time 0) and after 1, 2, 6, 8 and 12 weeks. Data is shown in FIG. 10.

Conclusions

Peptides 1 and 4 were stable in the studied formulations A, B and C throughout the 12 weeks.

Example 13. Skin Equivalent Culture

The aim of this study was to evaluate the effect of peptides 1 and 4 in formulation on pigmentation of skin samples by photographic assessment of pigmentation.

Materials and Methods

Pigmented skin equivalents (SEs), Melanoderms Mel-300-A (Asian donor) were obtained from Mattek Ltd together with the associated media EPI-100-NMM-113 and hanging well plates. The skin equivalent surface area was 63.6 $mm^2$. Other equipment used included SMZ1000 Stereo 10 Microscope (Nikon); UC30 Microscope Camera (Olympus); Sterile Phosphate-Buffered Saline (PBS, Thermofisher, UK); 12-well Tissue Culture Plates (Sarstedt). All incubations were carried out in a humidified incubator maintained at 37° C. with 5% $CO_2$. Pure peptide (>99%) was obtained from Biomatik, USA as acetate salt.

The Melanoderms were prepared by carefully removing the agarose with sterile forceps and placing in 5 ml prewarmed culture medium in hanging plates and incubated overnight. The following day prior to treatment, SEs were rinsed gently in PBS, excess moisture was removed from the surface using a sterile cotton bud, then transferred to 12-well plates containing 1 ml PBS in each well (to avoid drying out) for imaging. The tissue surface was photographed using an Olympus camera system attached to an inverted microscope to record initial pigmentation levels. SEs were transferred back to hanging well plates containing 5 ml fresh media. Three SEs were removed to provide baseline day 0 controls for analysis using WS staining and qPCR analysis.

SEs (n=3 per treatment) were topically treated for 7 days with 25 μl of the various peptide concentrations in formulations as prepared in Example 12 in parallel with relevant controls. These were as follows:

formulation B with 0.4%, 1% and 2% concentrations each of peptide 1, formulation B with 0.4%, 1% and 2% concentrations each of peptide 4, formulation B only (placebo), Peptides 1 and 4 each dissolved in sterile water at 10 mg/ml, 1 μM synthetic α-MSH analogue ([$Nle^4$,D-$Phe^7$]-α-MSH, Tocris, UK) dissolved in sterile water, and Untreated control (25 μl sterile water).

Each formulation was applied to the surface of SEs using a positive displacement pipette and spread evenly using a sterile microbiological loop. SEs were maintained at 37° C., 5% CO2 in a humidified incubator with media refreshed every other day until the end of treatment. On day 7 SEs were removed from culture and formulation carefully removed using a sterile microbiological loop and the surface rinsed in PBS then blotted dry with a sterile cotton bud. SEs were transferred to 12-well plates containing 1 ml PBS for imaging. The pigmentation of the Melanoderms was macroscopically assessed by capturing high-resolution images using the Olympus microscope camera.

Results

It was apparent from visual assessment that both peptides 1 and 4 in formulation B were more pigmented than the vehicle control (formulation B only) and the individual peptides dissolved in water (FIG. 11). Peptide 1 showed the highest response at the higher 1% and 2% concentrations whereas Peptide 4 at 0.4%, 1% and 2% showed an approximately equal increase in pigmentation relative to vehicle controls.

Conclusion

Visual assessment of SEs in culture suggests that treatment with peptide 1 and 4 for 7 days in formulation B can increase pigmentation in skin equivalent samples more effectively than when dissolved in water.

Example 14. Warthin-Starry Silver Staining of Melanin Granules in Melanoderms The aim of this study was to visualize and quantify the melanin distribution in the Melanoderm sections treated with three concentrations each of Peptides 1 and 4 in formulation B.

Methods

Tissue from each Melanoderm of Example 13 was carefully cut from inserts using a sterile scalpel blade (no. 11) and cut in half. One half was submerged overnight at −20° C. in RNAlater solution (Qiagen, UK) for RNA stabilization. The following day excess RNAlater solution was removed, and samples stored at −80° C. until RNA extracted for qPCR. The second half of each tissue was fixed overnight in 10% neutral buffered formalin then processed for wax embedding, sectioning, and Warthin-Starry staining.

All reagents used were of research grade quality and obtained from Sigma, UK. For silver staining high purity photo-grade (>99%) Silver nitrate was used. All reagents were prepared in acidulated (citrulated) distilled water (approx. 1 ml/L of 1% Citric acid was added to distilled water to change the pH to 3.4). Other equipment used were two water baths pre-set at 43° C. and 54° C., plastic staining tubs and slide racks for incubating slides, magnetic stirrers, and calibrated pH meter.

Melanin in tissue sections was stained using the modified Warthin-Starry staining method (Warthin, A. et al., Am. J. Syph. (1920) 4:97-103; Warkel, R. et al., Am. J. Clin. Path.

(1980) 73 June (6): 812-5.). Briefly, 7 μm tissue sections were cut from wax blocks and floated onto charged slides (Leica Xtra clipped corner glass slides). Sections were dried overnight at room temperature then dewaxed in HistoclearII solution (SLS, UK) and rehydrated through ethanol's to distilled water. Slides were pre-equilibrated in citrulated water for 5 min then melanin stained using the modified Warthin-Starry method (Warthin, A. et al., Am. J. Syph. (1920) 4:97-103; Warkel, R. et al., Am. J. Clin. Path. (1980) 73 June (6): 812-5.; Joly-Tonetti, N., Experimental Dermatology. (2016) 25(7): 501-504). Sections were impregnated in 1% (w/v) silver nitrate solution for 2 h at 4320 C. and transferred to freshly prepared developer solution (2% (w/v) silver nitrate solution, 5% (w/v) Gelatin, 0.15% (w/v) Hydroquinone) prewarmed at 54° C. Staining was viewed by observing under a microscope (between 30 see-2 min). Slides were rinsed in hot running tap water for 3 min, distilled water for 2 min then transferred to 5% Sodium thiosulphate for 2 min. Following further rinsing in tap water and distilled water for 5 min, slides were dehydrated in ethanol's, cleared in Histoclear II and a coverslip added with Histomount reagent (SLS, UK). Slides were allowed to dry for 48 hours before imaging. Images were captured using a Nikon binocular microscope and camera software in 8-bit greyscale and processed using FIJI software (Schindelin, J. et al.; Nature Methods (2012) 9(7), 676-682).

Results

Melanoderms treated with peptide 1 (in formulation B) at all three concentrations showed a modest increase in melanin in the basal and stratum spinosum layers compared to formulation only and a slight increase compared to the peptide dissolved in water particularly in the upper layers of the epidermis (FIG. 12). Melanoderms treated with peptide 4 (in formulation B) at all three concentrations showed a greater increase in melanin in all layers of the epidermis compared to both formulations only treated SEs and those treated with peptide 1 (in formulation B), with a visible increase in larger clusters of transferred granules within the keratinocytes of the upper (more differentiated) layers of the epidermis (stratum granulosum and corneum).

Conclusions

Both peptides 1 and peptide 4 in formulation B both increased the melanin content and number of transferred melanin granules in Melanoderm SEs compared to controls. Peptide 4 was more effective at increasing the amount of melanin in SEs and the number of transferred granules than Peptide 1.

Example 15. qPCR Expression Analysis of Melanogenesis Markers in Melanoderm SEs

The aim of this study was to measure the relative gene expression of selected pigmentation markers (PMEL, TYRP-1 and TYR) in SEs treated with three concentrations of Peptides 1 and 4 in formulation B.

Methods

RNA stabilized Melanoderm tissue from Example 13 was thawed on ice RNA extracted using the RNeasy extraction kit (Qiagen, UK) according to manufacturer's instructions. To ensure efficient lysis, tissue was ground in lysis buffer in a RNase-free 1.5 ml centrifuge tube using a sterile microbiological colony picker then passed through a Qiashredder column (Qiagen, UK) before lysate was purified. To prevent carry over of gDNA to qPCR, on-column digestion using 80 μl of DNase enzyme was added (DNase on column digestion kit, Sigma, UK). RNA was eluted in a 50 μl volume of sterile elution buffer and stored at −80° C. until use. For cDNA reverse transcription 8 μl of RNA was added as template in a 20 μl final volume in a 96-well plate using the iScript Advanced cDNA Synthesis Kit for RT-qPCR (Bio-Rad, UK) according to manufacturer's instructions. Low profile 96-well PCR plates and seals for qPCR reactions were obtained from Thermofisher. For qPCR 1 μl of cDNA from each test sample and relevant controls were amplified in a 96-well plate using SsoAdvanced Universal SYBR® Green Supermix and target pigmentation specific gene primers (pigment cell-specific pre-melanosomal protein (PMEL), Tyrosinase-related protein-1 (TYRP-1) and Tyrosinase (TYR)) in a 20 μl final reaction volume. Prevalidated primers, templates and gDNA controls were sourced from Bio-Rad, UK. Prevalidated template cDNA was included as a positive control for each gene tested. Ribosomal protein-20 (RPS20) was used as a housekeeping gene control. Samples were amplified using an Applied Biosystems StepOne Plus qPCR machine and associated software. Differences in fold gene expression between treatments and untreated controls were calculated from RPS20 reference gene normalised Ct values using the ΔΔCt method ($2^{-(\Delta\Delta Ct)}$). Final expression values were log 10 transformed prior to statistical analysis (unpaired t-test) using Prism software.

Results

The results of qPCR analysis are shown in bar charts in FIG. 13. Expression of the pigment cell-specific pre-melanosomal protein PMEL, the fibrils of which optimize sequestration and condensation of the melanin, was raised in all peptide treatments in formulation B when compared to untreated controls. Treatment with formulation B comprising 0.4% peptide 4 showed the greatest increase in expression which was significant when compared against formulation B treatment only (*p=0.015, t-test). No data was obtained for 1% peptide 1.

Tyrosinase related protein-1 (TYRP-1), which is involved in melanin synthesis, also showed a similar increase in expression levels following treatments with peptide in formulation B compared to untreated controls. Treatment with formulation B with 0.4% peptide 4 showed a moderately significant increase in expression when compared against formulation B only (**p=0.005, t-test).

Expression of the pigmentation gene Tyrosinase (TYR), which catalyses the production of melanin and other pigments from tyrosine by oxidation, showed a similar increase in expression following treatments with peptide in formulation B compared to untreated controls. Treatment with formulation B comprising 0.4% peptide 4 showed a significant increase in expression compared to formulation B only treated SEs (*p=0.027, t-test). No data was obtained for 1% peptide 1.

Conclusions

Treatment of SEs with Peptides 1 and 4 in formulation B displayed a trend for elevating expression of the pigmentation markers PMEL, TYRP-1 and Tyrosinase. Treatment with 0.4% peptide 4 in formulation B significantly showed the greatest increase in expression of all three markers tested.

Sequences

| SEQ ID NO | Sequence | Notes |
|---|---|---|
| 1 | $NAX_2M$ | $X_2$ is H or A |
| 2 | NAHM | Peptide 1 |
| 3 | AAHM | Peptide 3 |
| 4 | NAAM | Peptide 4 |
| 6 | VDTYDGDISVVYGLR | FOL-005 |
| 8 | CYIQNCPLG | Oxytocin |
| 9 | VDVPNGDISLAYGLR | FOL-004 |
| 10 | KPLAEIDSIELSYGIK | FOL-014 |
| 11 | GKYGFYTHVFRLKKWIQ KVIDQFGE | FOL-199 |
| 12 | LLGDFFRKSKEKIGKEFKRI VQRIKDFLRNLVPRTES | LL-37 |
| 13 | $X_1AX_2M$ | $X_1$ is N or A<br>$X_2$ is H or A |
| 14 | $KX_2LAX_5X_6X_7X_8IX_{10}LX_{12}$ YGIK | $X_2$ is C, P or G<br>$X_5$ is E or G<br>$X_6$ is C, D or I<br>$X_7$ is D, I, S or G<br>$X_8$ is S, D or G<br>$X_{10}$ is E or G<br>$X_{12}$ is S or T |
| 15 | $X_{10}LX_{12}YGIK$ | $X_{10}$ is E or G<br>$X_{12}$ is S or T |
| 16 | $VDVPZ_5GDISLAYZ_{13}LR$ | $Z_5$ is E or N<br>$Z_{13}$ is R or G |
| 17 | $VDTYDGZ_7Z_8SVVYGLR$ | $Z_7$ is D or G<br>$Z_8$ is I or G |
| 18 | $GDPNZ_5Z_6Z_7Z_8Z_9SVVYGLR$ | $Z_5$ is D or G<br>$Z_6$ is D or G<br>$Z_7$ is I or R<br>$Z_8$ is G or absent<br>$Z_9$ is D or absent |
| 19 | $KX_2LAX_5X_6X_7X_8IX_{10}L$ SYGIK | $X_2$ is C, Por G<br>$X_5$ is E or G<br>$X_6$ is C, I or absent<br>$X_7$ is D, G or absent<br>$X_8$ is S, G or absent<br>$X_{10}$ is E or G |
| 20 | $KX_2LAX_5IX_{10}LSYGIK$ | $X_2$ is C, Por G<br>$X_5$ is E or G<br>$X_{10}$ is E or G |
| 21 | $Z_7Z_8SZ_{10}Z_{11}YGLR$ | $Z_7$ is D or G<br>$Z_8$ is I or G<br>$Z_{10}$ is Vor L<br>$Z_{11}$ is V or A |
| 22 | $VDZ_3Z_4Z_5GZ_7Z_8SZ_{10}Z_{11}YGLR$ | $Z_3$ is T or V<br>$Z_4$ is Y or P<br>$Z_5$ is D or N<br>$Z_7$ is D or G<br>$Z_8$ is I or G<br>$Z_{10}$ is Vor L<br>$Z_{11}$ is V or A |

-continued

Sequences

| SEQ ID NO | Sequence | Notes |
|---|---|---|
| 23 | GDPNDGRGDSVVYGLR | |
| 24 | VDTYDGGISVVYGLR | |
| 25 | VDTYDGDGSVVYGLR | |
| 26 | VDVPEGDISLAYGLR | |
| 27 | LDGLVRAYDNISPVG | |
| 28 | GDPNGDISVVYGLR | |
| 29 | VDVPNGDISLAYRLR | |
| 30 | VDVPEGDISLAYRLR | |
| 31 | V(beta-D) TYDGDISVVYGLR | |
| 32 | VDTY(beta-D) GDISVVYGLR | |
| 33 | VDTYDG(beta-D) ISVVYGLR | |
| 34 | KCLAECDSIELSYGIK | |
| 35 | CLAEIDSC | |
| 36 | CFKPLAEIDSIECSYGIK | |
| 37 | KPLAEDISIELSYGIK | |
| 38 | KPLAEIGDIELSYGIK | |
| 39 | KPLAEGDIELSYGIK | |
| 40 | KPLAEIELSYGIK | |
| 41 | KPLAEIDSIELTYGIK | |
| 42 | KPLAEIDGIELSYGIK | |
| 43 | KPLAEIDGIELTYGIK | |
| 44 | KPLAEIGSIELSYGIK | |
| 45 | KGLAEIDSIELSYGIK | |
| 46 | KPLAGIDSIGLSYGIK | |
| 47 | KCLAEIDSCELSYGIK | |
| 48 | CFKPLAEIDSIEC | |
| 49 | LAEIDSIELSYGIK | |
| 50 | AEIDSIELSYGIK | |
| 51 | EIDSIELSYGIK | |
| 52 | IDSIELSYGIK | |
| 53 | DSIELSYGIK | |
| 54 | SIELSYGIK | |
| 55 | IELSYGIK | |
| 56 | KPLAEIDSIELSYGI | |
| 57 | KPLAEIDSIELSYG | |

-continued

| Sequences | | |
|---|---|---|
| SEQ ID NO | Sequence | Notes |
| 58 | KPLAEIDSIELSY | |
| 59 | KPLAEIDSIELS | |
| 60 | KPLAEIDSIEL | |
| 61 | KPLAEIDSIE | |
| 62 | VDTYDGDISVVYGLS | |
| 63 | VDTYDGDISVVYGL | FOL-025 |
| 64 | DTYDGDISVVYGLR | |
| 65 | TYDGDISVVYGLRS | |
| 66 | VDTYDGDISVVYG | FOL-024 |
| 67 | DTYDGDISVVYGL | |
| 68 | TYDGDISVVYGLR | |
| 69 | YDGDISVVYGLRS | |
| 70 | VDTYDGDISVVY | |
| 71 | DTYDGDISVVYG | |
| 72 | TYDGDISVVYGL | |
| 73 | YDGDISVVYGLR | |
| 74 | DGDISVVYGLRS | |
| 75 | VDTYDGDISVV | |
| 76 | DTYDGDISVVY | |
| 77 | TYDGDISVVYG | |
| 78 | YDGDISVVYGL | |
| 79 | DGDISVVYGLR | |
| 80 | GDISVVYGLRS | |
| 81 | VDTYDGDISV | |
| 82 | DTYDGDISVV | |
| 83 | TYDGDISVVY | |
| 84 | YDGDISVVYG | |
| 85 | DGDISVVYGL | |
| 86 | GDISVVYGLR | FOL-009h |
| 87 | DISVVYGLRS | |
| 88 | VDTYDGDIS | FOL-019h |
| 89 | DTYDGDISV | |
| 90 | TYDGDISVV | |
| 91 | YDGDISVVY | |
| 92 | DGDISVVYG | |
| 93 | GDISVVYGL | |
| 94 | DISVVYGLR | |
| 95 | ISVVYGLRS | |
| 96 | VDTYDGDI | |
| 97 | DTYDGDIS | |
| 98 | TYDGDISV | |
| 99 | YDGDISVV | |
| 100 | DGDISVVY | |
| 101 | GDISVVYG | |
| 102 | DISVVYGL | |
| 103 | ISVVYGLR | |
| 104 | VDTYDGD | |
| 105 | DTYDGDI | |
| 106 | TYDGDIS | |
| 107 | YDGDISV | |
| 108 | DGDISVV | |
| 109 | GDISVVY | |
| 110 | DISVVYG | |
| 111 | ISVVYGL | |
| 112 | DTYDGD | |
| 113 | TYDGDI | |
| 114 | YDGDIS | |
| 115 | DGDISV | |
| 116 | GDISVV | |
| 117 | DISVVY | |
| 118 | ISVVYG | |
| 119 | TYDGD | |
| 120 | YDGDI | |
| 121 | DGDIS | |
| 122 | GDISV | |
| 123 | DISVV | |
| 124 | ISVVY | |
| 125 | SVVYG | |
| 126 | VDTYDGRGDSVVYGLR | FOL-002 |
| 127 | DVPNGDISLAYGLRS | |
| 128 | VDVPNGDISLAYGL | FOL-016 |
| 129 | DVPNGDISLAYGLR | FOL-007 |
| 130 | VPNGDISLAYGLRS | |
| 131 | VDVPNGDISLAYG | FOL-017 |

-continued

| Sequences | | |
|---|---|---|
| SEQ ID NO | Sequence | Notes |
| 132 | DVPNGDISLAYGL | |
| 133 | VPNGDISLAYGLR | |
| 134 | PNGDISLAYGLRS | |
| 135 | VDVPNGDISLAY | |
| 136 | DVPNGDISLAYG | |
| 137 | VPNGDISLAYGL | |
| 138 | PNGDISLAYGLR | FOL-008 |
| 139 | NGDISLAYGLRS | |
| 140 | VDVPNGDISLA | FOL-018 |
| 141 | DVPNGDISLAY | |
| 142 | VPNGDISLAYG | |
| 143 | PNGDISLAYGL | |
| 144 | NGDISLAYGLR | |
| 145 | GDISLAYGLRS | |
| 146 | VDVPNGDISL | |
| 147 | DVPNGDISLA | |
| 148 | VPNGDISLAY | |
| 149 | PNGDISLAYG | |
| 150 | NGDISLAYGL | |
| 151 | GDISLAYGLR | FOL-009 |
| 152 | DISLAYGLRS | |
| 153 | VDVPNGDIS | FOL-019 |
| 154 | DVPNGDISL | |
| 155 | VPNGDISLA | |
| 156 | PNGDISLAY | |
| 157 | NGDISLAYG | |
| 158 | GDISLAYGL | |
| 159 | DISLAYGLR | |
| 160 | ISLAYGLRS | |
| 161 | VDVPNGDI | |
| 162 | DVPNGDIS | |
| 163 | VPNGDISL | |
| 164 | PNGDISLA | |
| 165 | NGDISLAY | |
| 166 | GDISLAYG | |
| 167 | DISLAYGL | |
| 168 | ISLAYGLR | |

-continued

| Sequences | | |
|---|---|---|
| SEQ ID NO | Sequence | Notes |
| 169 | VDVPNGD | |
| 170 | DVPNGDI | |
| 171 | VPNGDIS | |
| 172 | PNGDISL | |
| 173 | NGDISLA | |
| 174 | GDISLAY | |
| 175 | DISLAYG | |
| 176 | ISLAYGL | |
| 177 | DVPNGD | |
| 178 | VPNGDI | |
| 179 | PNGDIS | |
| 180 | NGDISL | |
| 181 | GDISLA | |
| 182 | DISLAY | |
| 183 | ISLAYG | |
| 184 | VPNGD | |
| 185 | PNGDI | |
| 186 | NGDIS | |
| 187 | GDISL | |
| 188 | DISLA | |
| 189 | ISLAY | |
| 190 | SLAYG | |
| 191 | VDVPNGRGDSLAYGLR | FOL-001 |
| 192 | GDPNDGRGDSVVYGLR | FOL-003 |
| 193 | KPLAEDISIELSYGIK | FOL-037 |
| 194 | $X_{10}LX_{12}YGIK$ | $X_{10}$ is E or G<br>$X_{12}$ is S or T |
| 195 | $Z_7Z_8SZ_{10}Z_{11}YGLR$ | $Z_7$ is D or G<br>$Z_8$ is I or G<br>$Z_{10}$ is Vor L<br>$Z_{11}$ is V or A |
| 196 | GKYGFYTHVFRLKKWI QKVIDQFGE | FOL-199 |

The invention claimed is:

1. A cosmetic method of darkening of skin or hair color, the method comprising administering to a subject in need thereof a peptide or peptide derivative comprising Asn-Ala-Xaa2-Met (SEQ ID NO: 1), wherein Xaa2 is His or Ala, and wherein the peptide or peptide derivative is no more than 8 amino acid residues in length.

2. The method according to claim 1, wherein the method non-therapeutically increases melanin pigmentation of skin or hair of the subject.

3. The method according to claim 1, wherein the peptide or peptide derivative comprises no more than 5 amino acid residues.

4. The method according to claim 1, wherein the peptide or peptide derivative comprises no more than 6 amino acid residues.

5. The method according to claim 1, wherein the peptide or peptide derivative comprises no more than 7 amino acid residues.

6. The method according to claim 1, wherein the peptide or peptide derivative comprises the amino acid sequence Asn-Ala-Ala-Met (SEQ ID NO: 4).

7. The method according to claim 1, wherein the peptide or peptide derivative consists of the amino acid sequence Asn-Ala-Ala-Met (SEQ ID NO: 4).

8. The method according to claim 1, wherein the peptide or peptide derivative comprises the amino acid sequence Asn-Ala-His-Met (SEQ ID NO: 2).

9. The method according to claim 1, wherein the peptide or peptide derivative consists of the amino acid sequence Asn-Ala-His-Met (SEQ ID NO: 2).

10. A method for treatment of a disease or disorder associated with hypopigmentation comprising administering to a subject in need thereof a peptide or peptide derivative comprising Asn-Ala-Xaa2-Met (SEQ ID NO: 1), wherein Xaa2 is His or Ala, and wherein the peptide or peptide derivative is no more than 8 amino acid residues in length.

11. The method according to claim 10, wherein the disease or disorder associated with hypopigmentation is selected from the group consisting of vitiligo, albinism, idiopathic guttate hypomelanosis, leprosy, leucism, phenylketonuria, *pityriasis* alba, Angelman syndrome, *tinea versicolor*, yaws, post-inflammatory hypopigmentation and pigmentation loss as a result of skin damage.

12. The method according to claim 10, wherein the peptide or peptide derivative comprises no more than 5 amino acid residues.

13. The method according to claim 10, wherein the peptide or peptide derivative comprises no more than 6 amino acid residues.

14. The method according to claim 10, wherein the peptide or peptide derivative comprises no more than 7 amino acid residues.

15. The method according to claim 10, wherein the peptide or peptide derivative comprises the amino acid sequence Asn-Ala-Ala-Met (SEQ ID NO: 4).

16. The method according to claim 10, wherein the peptide or peptide derivative consists of the amino acid sequence Asn-Ala-Ala-Met (SEQ ID NO: 4).

17. The method according to claim 10, wherein the peptide or peptide derivative comprises the amino acid sequence Asn-Ala-His-Met (SEQ ID NO: 2).

18. The method according to claim 10, wherein the peptide or peptide derivative consists of the amino acid sequence Asn-Ala-His-Met (SEQ ID NO: 2).

19. The method according to claim 1, wherein said method is darkening of skin color and wherein the amino acid sequence comprises Asn-Ala-Ala-Met (SEQ ID NO: 4).

20. The method according to claim 1, wherein the peptide or peptide derivative further comprises a modification, wherein said modification is a glycosylation, PEGylation, amidation, esterification, acylation, acetylation, and/or alkylation.

* * * * *